(12) United States Patent
Chen et al.

(10) Patent No.: US 11,365,206 B2
(45) Date of Patent: Jun. 21, 2022

(54) BCL-2 INHIBITORS

(71) Applicant: Newave Pharmaceutical Inc., Pleasanton, CA (US)

(72) Inventors: Yi Chen, Pleasanton, CA (US); Yan Lou, Pleasanton, CA (US)

(73) Assignee: Newave Pharmaceutical Inc., Pleasanton, CA (US)

( * ) Notice: Subject to any disclaimer, the term of this patent is extended or adjusted under 35 U.S.C. 154(b) by 52 days.

(21) Appl. No.: 16/795,720

(22) Filed: Feb. 20, 2020

(65) Prior Publication Data
US 2020/0197406 A1 Jun. 25, 2020

Related U.S. Application Data

(63) Continuation of application No. PCT/US2018/047444, filed on Aug. 22, 2018.

(60) Provisional application No. 62/615,007, filed on Jan. 9, 2018, provisional application No. 62/549,081, filed on Aug. 23, 2017.

(51) Int. Cl.
| | |
|---|---|
| A61P 35/04 | (2006.01) |
| A61P 35/00 | (2006.01) |
| A61P 35/02 | (2006.01) |
| A61P 37/00 | (2006.01) |
| C07D 498/14 | (2006.01) |
| C07D 513/14 | (2006.01) |
| A61K 45/06 | (2006.01) |
| A61K 31/542 | (2006.01) |
| A61K 31/5383 | (2006.01) |

(52) U.S. Cl.
CPC ........ C07D 498/14 (2013.01); A61K 31/5383 (2013.01); A61K 31/542 (2013.01); A61K 45/06 (2013.01); A61P 35/00 (2018.01); A61P 35/02 (2018.01); A61P 35/04 (2018.01); A61P 37/00 (2018.01); C07D 513/14 (2013.01)

(58) Field of Classification Search
CPC ......... A61P 35/00; A61P 35/02; A61P 35/04; A61P 37/00; A61K 45/06; A61K 31/542; A61K 31/5383; C07D 498/14; C07D 513/14
See application file for complete search history.

(56) References Cited

U.S. PATENT DOCUMENTS

| | | | |
|---|---|---|---|
| 7,642,260 B2 | 1/2010 | Bruncko et al. | |
| 7,767,684 B2 | 8/2010 | Bruncko et al. | |
| 7,973,161 B2 | 7/2011 | Bruncko et al. | |
| 8,084,607 B2 | 12/2011 | Bruncko et al. | |
| 8,173,811 B2 | 5/2012 | Bruncko et al. | |
| 8,354,404 B2 | 1/2013 | Bruncko et al. | |
| 8,546,399 B2 | 10/2013 | Bruncko et al. | |
| 8,557,983 B2 | 10/2013 | Doherty et al. | |
| 8,563,735 B2 | 10/2013 | Bruncko et al. | |
| 8,580,794 B2 | 11/2013 | Doherty et al. | |
| 8,586,754 B2 | 11/2013 | Bruncko et al. | |
| 8,614,318 B2 | 12/2013 | Bruncko et al. | |
| 8,686,136 B2 | 4/2014 | Bruncko et al. | |
| 8,952,157 B2 | 2/2015 | Ding et al. | |
| 9,006,247 B2 | 4/2015 | Tao et al. | |
| 9,029,404 B2 | 5/2015 | Doherty et al. | |
| 9,034,875 B2 | 5/2015 | Doherty et al. | |
| 9,045,420 B2 | 6/2015 | Doherty et al. | |
| 9,045,444 B2 | 6/2015 | Ding et al. | |
| 9,045,475 B2 | 6/2015 | Elmore et al. | |

(Continued)

FOREIGN PATENT DOCUMENTS

| | | |
|---|---|---|
| EP | 2376480 A2 | 10/2011 |
| WO | 2005/049593 A2 | 6/2005 |

(Continued)

OTHER PUBLICATIONS

AD-Medications, 2021, https://www.mayoclinic.org/diseases-conditions/alzheimers-disease/in-depth/alzheimers/art-20048103.*
MS-Medications, 2021, https://www.mayoclinic.org/diseases-conditions/multiple-sclerosis/diagnosis-treatment/drc-20350274.*
Cancer-Prevention, 2021, https://www.cancerresearchuk.org/about-cancer/causes-of-cancer/can-cancer-be-prevented-0.*
Cancer-Cure, 2021, https://www.webmd.com/cancer/guide/cure-for-cancer#:~:text=Continued-,Treatment,time%3A%20even%20years%20or%20decades.*
Chen et al., 2017, caplus an 2017:1256516.*

(Continued)

*Primary Examiner* — Sun Jae Yoo
(74) *Attorney, Agent, or Firm* — McCarter & English, LLP; Yu Lu; Zhongyu "Alex" Wang

(57) ABSTRACT

The disclosure includes compounds of Formula (A):

Formula (A)

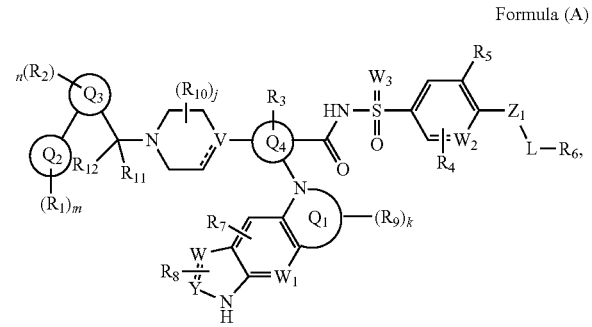

wherein $R_1$, $R_2$, $R_3$, $R_4$, $R_5$, $R_6$, $R_7$, $R_8$, $R_9$, $R_{10}$, $R_{11}$, and $R_{12}$, j, k, m, n, Y, W, $W_1$, $W_2$, $W_3$, V, L, $Z_1$, $Q_1$, $Q_2$, $Q_3$, and $Q_4$, are defined herein. Also disclosed is a method for treating a neoplastic disease, an autoimmune disease, or a neurodegenerative disease with these compounds.

30 Claims, No Drawings

(56) References Cited

U.S. PATENT DOCUMENTS

| | | |
|---|---|---|
| 9,045,920 B2 | 6/2015 | Minemura |
| 9,072,748 B2 | 7/2015 | Bruncko et al. |
| 9,073,855 B2 | 7/2015 | Doherty et al. |
| 9,125,913 B2 | 9/2015 | Bruncko et al. |
| 9,174,982 B2 | 11/2015 | Bruncko et al. |
| 9,303,025 B2 | 4/2016 | Bruncko et al. |
| 9,315,488 B2 | 4/2016 | Ding et al. |
| 9,403,822 B2 | 8/2016 | Tao et al. |
| 10,377,755 B2 | 8/2019 | Chen et al. |
| 2010/0152183 A1 | 6/2010 | Bruncko et al. |
| 2010/0298321 A1 | 11/2010 | Bruncko et al. |
| 2010/0298323 A1 | 11/2010 | Bruncko et al. |
| 2010/0305122 A1 | 12/2010 | Bruncko et al. |
| 2011/0124628 A1 | 5/2011 | Bruncko et al. |
| 2012/0108590 A1 | 5/2012 | Birtalan et al. |
| 2014/0057890 A1 | 2/2014 | Bruncko et al. |
| 2016/0304451 A1 | 10/2016 | Elmore et al. |
| 2017/0096424 A1 | 4/2017 | Tao et al. |
| 2017/0158666 A1 | 6/2017 | Bruncko et al. |
| 2018/0251426 A1 | 9/2018 | Bruncko et al. |
| 2020/0071329 A1 | 3/2020 | Chen et al. |
| 2020/0190109 A1 | 6/2020 | Chen et al. |
| 2021/0171523 A1 | 6/2021 | Chen et al. |

FOREIGN PATENT DOCUMENTS

| | | |
|---|---|---|
| WO | 2005/049594 A1 | 6/2005 |
| WO | 2009/036035 A1 | 3/2009 |
| WO | 2010/065824 A2 | 6/2010 |
| WO | 2010/065865 A2 | 6/2010 |
| WO | 2010/138588 A2 | 12/2010 |
| WO | 2011/068560 A1 | 6/2011 |
| WO | 2011/068561 A1 | 6/2011 |
| WO | 2011/149492 A1 | 12/2011 |
| WO | 2011/150016 A1 | 12/2011 |
| WO | 2012/058392 A1 | 5/2012 |
| WO | 2012/071336 A1 | 5/2012 |
| WO | 2012/121758 A1 | 9/2012 |
| WO | 2014/165044 A1 | 10/2014 |
| WO | 2017/132474 A1 | 8/2017 |
| WO | 2018/127130 A1 | 7/2018 |
| WO | 2018/192462 A1 | 10/2018 |
| WO | 2019/040550 A1 | 2/2019 |
| WO | 2019/040573 A1 | 2/2019 |
| WO | 2020/041405 A1 | 2/2020 |
| WO | 2020/041406 A1 | 2/2020 |

OTHER PUBLICATIONS

CNN.com./Health, FDA mulls drug to slow late-stage Alzheimer's. Retrieved online at: http://www.cnn/com/2003/Health/Conditions/09/24/alzheimers.drug.ap/index.html. 2 pages, Sep. 24, 2003.

Damaslo, Alzheimer's Disease and Related Dementias. Cecil Textbook of Medicine. 20th Edition, vol. 2. J. Claude Bennett (Ed.), W.B. Saunders Company, Philadelphia. pp. 1992-1996, (1996).

Golub et al., Molecular classification of cancer: class discovery and class prediction by gene expression monitoring Science. Oct. 15, 1999;286(5439):531-537.

Lala et al., Role of nitric oxide in tumor progression: lessons from experimental tumors. Cancer Metastasis Rev. 1998;17(1):91-106.

Layzer, Section Five—Degenerative Diseases of the Nervous System. Cecil Textbook of Medicine. 20th Edition, vol. 2. J. Claude Bennett (Ed.), W.B. Saunders Company, Philadelphia. pp. 2050-2057, (1996).

PubChem, SCHEMBL17897155, Compound Summary for CID 24729558. 14 pages. Retrieved online at: https://pubchem.ncbi.nlm.nih.gov/compound/24729558. Mar. 4, 2017.

Souers et al., ABT-199, a potent and selective BCL-2 inhibitor, achieves antitumor activity while sparing platelets. Nat Med. Feb. 2013;19(2):202-8.

International Search Report and Written Opinion for Application No. PCT/US2018/047444, dated Oct. 8, 2018, 9 pages.

International Search Report and Written Opinion for Application No. PCT/US2018/047411, dated Oct. 1, 2018, 8 pages.

International Search Report and Written Opinion for Application No. PCT/US2019/047404, dated Oct. 9, 2019, 10 pages.

International Search Report and Written Opinion for Application No. PCT/US2019/047403, dated Oct. 17, 2019, 12 pages.

U.S. Appl. No. 16/045,736, filed Jul. 26, 2018, U.S. Pat. No. 10,377,755, Issued.

U.S. Appl. No. 16/529,228, filed Aug. 1, 2019, 2020-0071329, Abandoned.

U.S. Appl. No. 16/879,270, filed May 20, 2020, Abandoned.

U.S. Appl. No. 17/035,865, filed Sep. 29, 2020, Abandoned.

U.S. Appl. No. 17/178,930, filed Feb. 18, 2021, 2021-0171523, Published.

U.S. Appl. No. 17/389,493, filed Jul. 30, 2021, Pending.

U.S. Appl. No. 17/416,682, filed Jun. 21, 2021, Pending.

U.S. Appl. No. 17/269,003, filed Feb. 17, 2021, Pending.

U.S. Appl. No. 17/269,004, filed Feb. 17, 2021, Pending.

U.S. Appl. No. 16/795,884, filed Feb. 20, 2020, 2020-0190109, Published.

International Search Report and Written Opinion for Application No. PCT/US2020/020010, dated Jun. 3, 2020, 10 pages.

International Search Report and Written Opinion for Application No. PCT/US2020/066650, dated Mar. 29, 2021, 18 pages.

International Search Report and Written Opinion for Application No. PCT/US2019/068685, dated Jun. 29, 2020, 19 pages.

\* cited by examiner

BCL-2 INHIBITORS

CROSS-REFERENCES TO RELATED APPLICATIONS

This application is a continuation of International Patent Application No.: PCT/US2018/047444, filed on Aug. 22, 2018, which claims the benefit of the filing date of U.S. Provisional Application No. 62/549,081, filed on Aug. 23, 2017; and U.S. Provisional Application No. 62/615,007, filed on Jan. 9, 2018. The entire contents of each of the aforementioned applications are incorporated herein by reference.

BACKGROUND OF THE INVENTION

Apoptosis, or programmed cell death, is a conserved and regulated process that is the primary mechanism for the removal of aged, damaged and unnecessary cells. The ability to block apoptotic signaling is a key hallmark of cancer and is thus important for oncogenesis, tumor maintenance and chemoresistance [Hanahan, D. & Weinberg, R. A. The hallmarks of cancer. Cell 100, 57-70 (2000)]. Dynamic binding interactions between prodeath (for example, BCL-2-associated X protein (BAX), BCL-2 antagonist/killer 1 (BAK), BCL-2 associated agonist of cell death (BAD), BCL-2-like 11 (BIM), NOXA and BCL-2 binding component 3 (PUMA)) and prosurvival (BCL-2, BCL-XL, BCL-2-like 2 (BCL-W), myeloid cell leukemia sequence 1 (MCL-1) and BCL-2-related protein A1 (BFL-1)) proteins in the BCL-2 family control commitment to programmed cell death. Altering the balance among these opposing factions provides one means by which cancer cells undermine normal apoptosis and gain a survival advantage [Youle, R. J. & Strasser, A. The BCL-2 protein family opposing activities that mediate cell death. Nat. Rev. Mol. Cell Biol. 9, 47-59 (2008)].

BCL-2, the first identified apoptotic regulator, was originally cloned from the breakpoint of a t(14;18) translocation present in human B cell lymphomas [Tsujimoto, Y., et al. Science 228, 1440-1443 (1985); Cleary, M. L., et al Cell 47, 19-28 (1986); Boise, L. H. et al. Cell 74, 597-608 (1993)]. This protein has since been shown to have a dominant role in the survival of multiple lymphoid malignancies [Vaux, D. L., et al pre-B cells. Nature 335, 440-442 (1988)]. Overexpression of Bcl-2 proteins correlates with resistance to chemotherapy, clinical outcome, disease progression, overall prognosis or a combination thereof in various cancers and disorders of the immune system. Involvement of Bcl-2 proteins in bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer, spleen cancer, and the like is described in PCT US 2004/36770, published as WO 2005/049593, and PCT US 2004/37911, published as WO 2005/024636. Involvement of Bcl-2 proteins in immune and autoimmune diseases is described in Current Allergy and Asthma Reports 2003, 3, 378-384; British Journal of Hematology 2000, 110(3), 584-90; Blood 2000, 95(4), 1283-92; and New England Journal of Medicine 2004, 351(14), 1409-1418. Involvement of Bcl-2 proteins in arthritis is disclosed in WO 2009/064938. Involvement of Bcl-2 proteins in bone marrow transplant rejection is disclosed in US 2008-0182845 A1. All incorporated herein by reference.

In the last decade, several Bcl-2 inhibitors such as ABT-737, ABT-263, and ABT-199 as shown below have been identified and entered human clinical trials for cancers treatment.

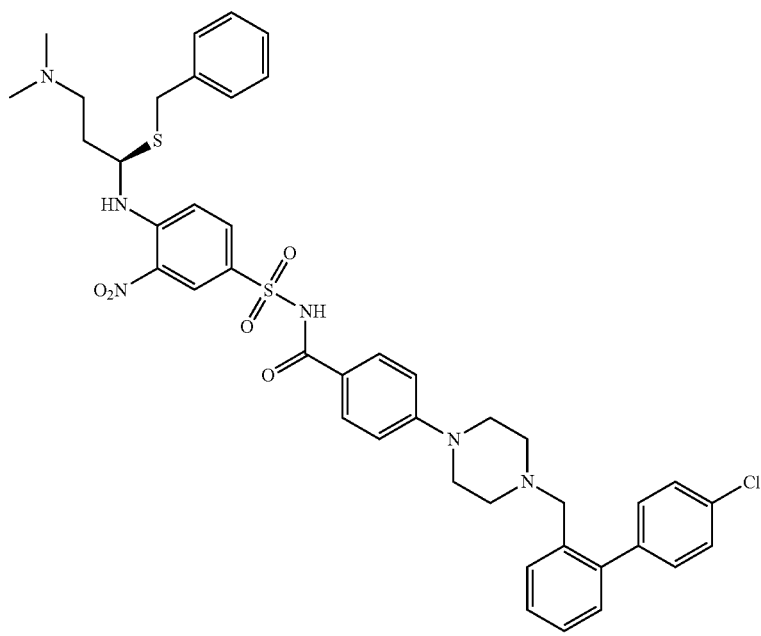

ABT-737

-continued

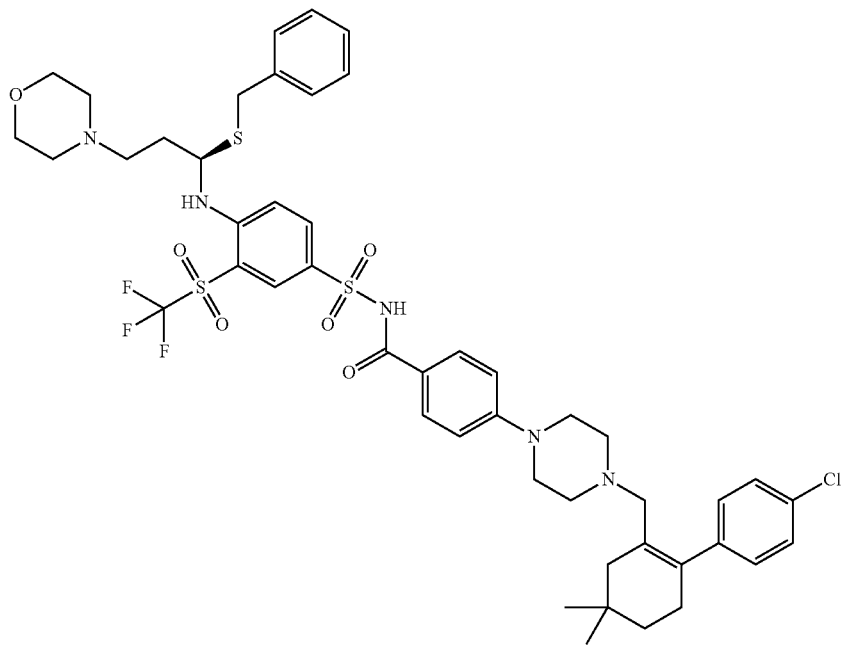

ABT-263

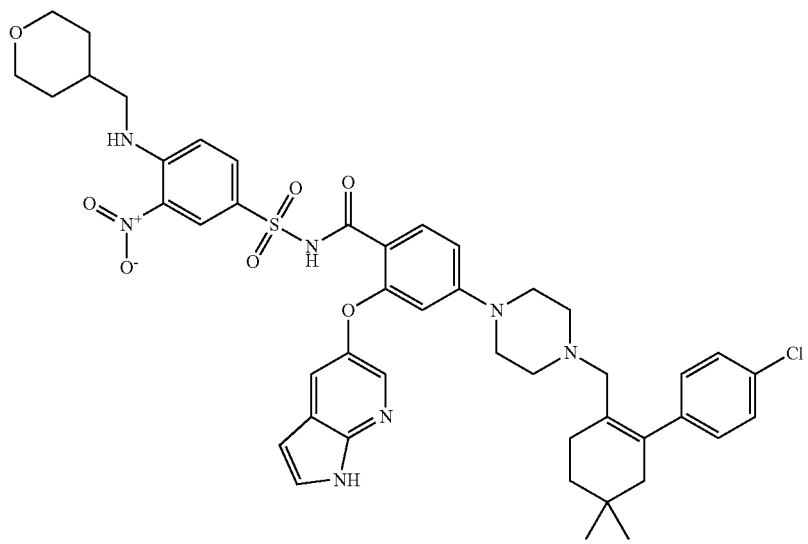

ABT-199

ABT-737 is discovered by nuclear magnetic resonance (NMR)-based screening, parallel synthesis and structure based fragment drug design [Tillman Oltersdorf, et al, Nature, Vol 435, 2005, p 677]. ABT-737 a small-molecule inhibitor of the anti-apoptotic proteins Bcl-2, Bcl-XL and Bcl-w, with an affinity two to three orders of magnitude more potent than previously reported compounds. Mechanistic studies reveal that ABT-737 does not directly initiate the apoptotic process, but enhances the effects of death signals, displaying synergistic cytotoxicity with chemotherapeutics and radiation. ABT-737 exhibits single-agent-mechanism-based killing of cells from lymphoma and small-cell lung carcinoma lines, as well as primary patient-derived cells, and in animal models, ABT-737 improves survival, causes regression of established tumors, and produces cures in a high percentage of the mice. Unfortunately, ABT-737 is not orally bioavailable, and its formulation for intravenous delivery is hampered by its low aqueous solubility.

After extensive MedChem effort, an orally bioavailable Bcl-2 inhibitor ABT-263 (Navitoclax) has been developed [Cheol-Min Park, et al J. Med. Chem. 2008, 51, 6902-6915]. ABT-263 is a potent inhibitor of Bcl-xL, Bcl-2 and Bcl-w with Ki of ≤0.5 nM, ≤1 nM and ≤1 nM. ABT-263 has an $IC_{50}$ of 110 nM against SCLC H146 cell line. When ABT-263 is administered at 100 mg/kg/day in the H345 xenograft model, significant antitumor efficacy is observed with 80% TGI and 20% of treated tumors indicating at least a 50% reduction in tumor volume. Oral administration of ABT-263 alone causes complete tumor regressions in xenograft models of small-cell lung cancer and acute lymphoblastic leukemia [Tse C, et al. Cancer Res. 2008, 68(9), 3421-3428]. In the clinical trial, however, the inhibition of BCL-XL by ABT-263 (navitoclax) induces a rapid, concentration-dependent decrease in the number of circulating platelets. This mechanism-based thrombocytopenia is the dose-limiting toxicity of single-agent navitoclax treatment in patients and limits the ability to drive drug concentrations into a highly efficacious range.

Thus, a BCL-2 selective (BCL-XL sparing) inhibitor would culminate in substantially reduced thrombocytopenia while maintaining efficacy in lymphoid malignancies. The resulting increase in the therapeutic window should allow for greater BCL-2 suppression and clinical efficacy in BCL-2-dependent tumor types. After extensive MedChem, ABT-199 (GDC-0199) has been successfully developed [Andrew J Souers, et al, Nature Medicine, Volume 19, 22, p 202, 2013]. ABT-199 is a Bcl-2-selective inhibitor with Ki of <0.01 nM, >4800-fold more selective versus Bcl-xL and Bcl-w, and no activity to Mcl-1. ABT-199 potently inhibits RS4;11 cells with $EC_{50}$ of 8 nM. In addition, ABT-199 induces a rapid apoptosis in RS4;11 cells with cytochrome c release, caspase activation, and the accumulation of sub-G0/G1 DNA. Quantitative immunoblotting reveals that sensitivity to ABT-199 correlated strongly with the expression of Bcl-2, including NHL, DLBCL, MCL, AML and ALL cell lines. ABT-199 also induces apoptosis in CLL with an average $EC_{50}$ of 3.0 nM. A single dose of 100 mg/kg of ABT-199 causes a maximal tumor growth inhibition of 95% and tumor growth delay of 152% in RS4;11 xenografts. ABT-199 also inhibits xenograft growth (DoHH2, Granta-519) as a single agent or in combination with Bendamustine and other agents. Human Phase I and II data showed that ABT-199 is highly efficacious for CLL who have 17p deletion, and was approved by FDA in 2016.

WO/2017/132474 discloses a novel class of BCL-2 inhibitors. However, there is still a strong need for continuing search in this field of art for more potent BCL-2 inhibitor.

SUMMARY OF THE INVENTION

In a first embodiment, this invention provides compounds of the Formula (A) or an N-oxide thereof, or a pharmaceutically acceptable salt, solvate, polymorph, tautomer, stereoisomer, an isotopic form, or a prodrug of said compound of Formula (A) or N-oxide thereof:

Formula (A)

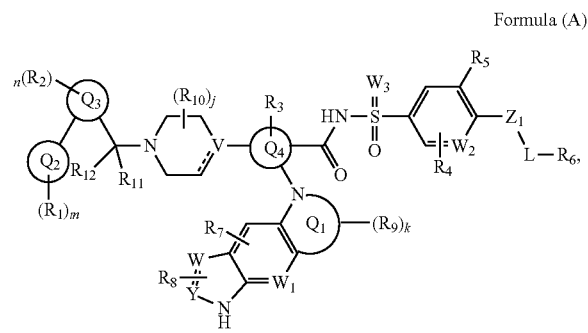

wherein $Q_1$ is a 6-membered heterocycloalkyl, 6-membered heterocycloalkenyl, or 6-membered heteroaryl;

$Q_2$ is an aryl, or heteroaryl;

$Q_3$ is a cycloalkyl, cycloalkenyl, heterocycloalkyl, heterocycloalkenyl, aryl, or heteroaryl;

$Q_4$ is

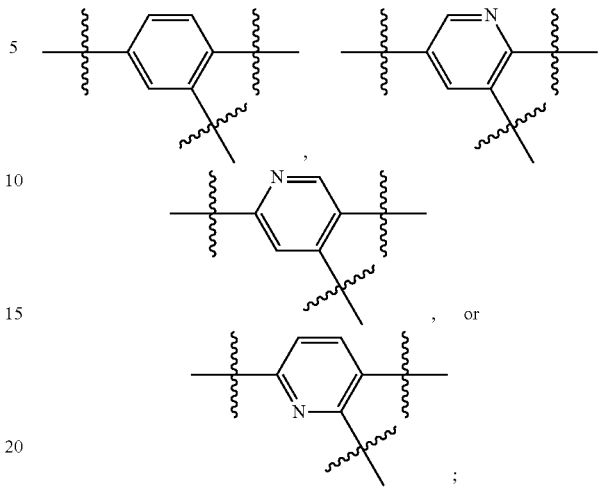

each of $R_1$, $R_2$, $R_3$, $R_4$, $R_5$, $R_6$, $R_7$, $R_8$, $R_9$, $R_{10}$, $R_{11}$, and $R_{12}$, independently, is H, D, alkyl, alkenyl, alkynyl, cycloalkyl, cycloalkenyl, heterocycloalkyl, heterocycloalkenyl, aryl, heteroaryl, halo, nitro, oxo, cyano, $OR_a$, $SR_a$, alkyl-$R_a$, $NH(CH_2)_pR_a$, $C(O)R_a$, $S(O)R_a$, $SO_2R_a$, $C(O)OR_a$, $OC(O)R_a$, $NR_bR_e$, $P(O)R_bR_c$, alkyl-$P(O)R_bR_c$, $C(O)N(R_b)R_c$, $N(R_b)C(O)R_c$, $S(O)(=N(R_a))R_b$, —N=S(O)$R_bR_c$, $SO_2N(R_b)R_c$, or $N(R_b)SO_2R_c$, in which said cycloalkyl, cycloalkenyl, heterocycloalkyl, heterocycloalkenyl, aryl, heteroaryl is optionally substituted with one or more $R_d$;

$R_a$, $R_b$, $R_c$ and $R_d$, independently, is H, D, alkyl, alkenyl, alkynyl, halo, cyano, amine, nitro, hydroxy, C(O)NHOH, C(O)OH, C(O)NH$_2$, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, heterocycloalkenyl, aryl, or heteroaryl, in which said alkyl, cycloalkyl, cycloalkenyl, heterocycloalkyl, heterocycloalkenyl, aryl, heteroaryl is optionally substituted with one or more $R_e$;

$R_e$ is H, D, alkyl, alkenyl, alkynyl, halo, cyano, amine, nitro, hydroxy, C(O)NHOH, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, heterocycloalkenyl, aryl, or heteroaryl;

$Z_1$ is a bond, $(CH_2)_p$, N(H), O, S, C(O), S(O$_2$), OC(O), C(O)O, OSO$_2$, S(O$_2$)O, C(O)S, SC(O), C(O)C(O), C(O)N(H), N(H)C(O), S(O$_2$)N(H), N(H)S(O$_2$), OC(O)O, OC(O)S, OC(O)N(H), N(H)C(O)O, N(H)C(O)S, N(H)C(O)N(H), $(CH_2)_pN(H)(CH_2)_q$, $(CH_2)_pN(H)C(O)(CH_2)_q$, $(CH_2)_pC(O)N(H)(CH_2)_q$, OC(O)N(H)(CH$_2$)$_{p+1}$N(H)(CH$_2$)$_q$, a bivalent alkenyl group, or a bivalent alkynyl group;

L is a bond, alkyl, alkenyl, alkynyl, cycloalkyl, cycloalkenyl, heterocycloalkyl, heterocycloalkenyl, aryl, or heteroaryl, in which said alkyl, cycloalkyl, cycloalkenyl, heterocycloalkyl, heterocycloalkenyl, aryl, or heteroaryl is optionally substituted with one or more $R_d$;

each of Y, W, and $W_2$, independently, is CH or N;

$W_1$ is N;

$W_3$ is O or N($R_a$);

V is N, C, or CH;

two of $R_9$ group, taken together with the atom to which they are attached, may optionally form a cycloalkyl or heterocycloalkyl, in which said cycloalkyl or heterocycloalkyl of $R_9$ is optionally substituted with one or more $R_d$;

two of $R_2$ group, taken together with the atom to which they are attached, may optionally form a cycloalkyl or heterocycloalkyl, in which said cycloalkyl or heterocycloalkyl of $R_2$ is optionally substituted with one or more $R_d$;

two of $R_{10}$ group, taken together with the atom to which they are attached, may optionally form a cycloalkyl or heterocycloalkyl, in which said cycloalkyl or heterocycloalkyl of $R_{10}$ is optionally substituted with one or more $R_d$;

$R_{11}$ and $R_{12}$ group, taken together with the atom to which they are attached, may optionally form a cycloalkyl or heterocycloalkyl, in which said cycloalkyl or heterocycloalkyl of $R_{11}$ or $R_{12}$ is optionally substituted with one or more $R_d$;

$R_{10}$ and $R_2$ group, taken together with the atom to which they are attached, may optionally form a cycloalkyl or heterocycloalkyl, in which said cycloalkyl or heterocycloalkyl of $R_{10}$ or $R_2$ is optionally substituted with one or more $R_d$;

$R_4$ and —$Z_1$-L-$R_6$ group, taken together with the atom to which they are attached, may optionally form a cycloalkyl, cycloalkenyl, heterocycloalkyl, heterocycloalkenyl, aryl, or heteroaryl, in which said cycloalkyl, cycloalkenyl, heterocycloalkyl, heterocycloalkenyl, aryl, or heteroaryl of $R_4$ is optionally substituted with one or more $R_d$;

$R_b$ and $R_c$ group, taken together with the atom to which they are attached, may optionally form a cycloalkyl, or heterocycloalkyl, in which said cycloalkyl or heterocycloalkyl of $R_b$ and $R_c$, is optionally substituted with one or more $R_c$;

two of $R_d$ group, taken together with the atom to which they are attached, may optionally form a cycloalkyl, or heterocycloalkyl, in which said cycloalkyl or heterocycloalkyl of $R_d$ is optionally substituted with one or more $R_e$;

two of $R_e$ group, taken together with the atom to which they are attached, may optionally form a cycloalkyl, or heterocycloalkyl;

each of j and k, independently, is 0, 1, 2, 3, 4, 5, 6, 7, or 8; and each of m, n, p, q, and r, independently, is 0, 1, 2, 3, or 4;

optionally, provided that when

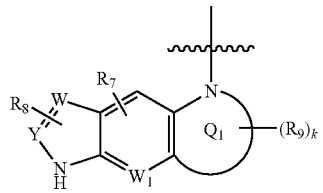

is

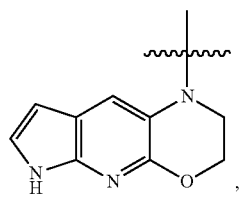

then —$Z_1$-L-$R_6$ is not

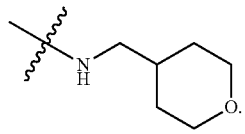

In a second embodiment, the invention provides a compound represented by Formula (B), wherein $Z_2$ is —O—, —$CH_2$—, —C(O)—, —N($R_a$)—, —S—, —S(O)—, —S($O_2$)—, —S(O)(=N($R_a$))—, or —P(O)($R_a$)—; and A is —C($R_2R_2$)—, or —O—:

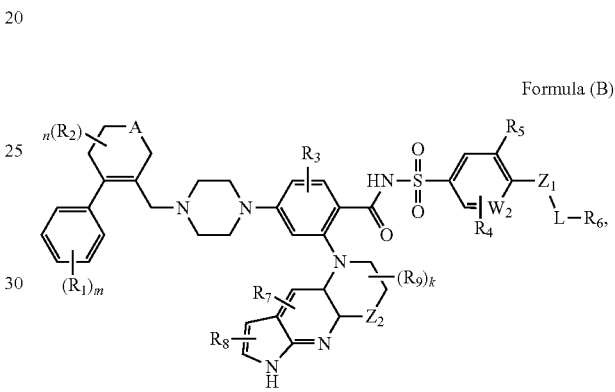

Formula (B)

or an N-oxide thereof, or a pharmaceutically acceptable salt, solvate, polymorph, tautomer, stereoisomer, an isotopic form, or a prodrug of said compound of Formula (B) or N-oxide thereof, wherein $Z_2$ is —O—, —$CH_2$—, —C(O)—, —N($R_a$)—, —S—, —S(O)—, —S($O_2$)—, —S(O)(=N($R_a$))—, —P(O)($R_a$)—; wherein $R_a$ of $Z_2$, independently, is H, D, $C_1$-$C_6$alkyl, $C_2$-$C_6$alkenyl, $C_1$-$C_6$alkylcarbonyl, $C_1$-$C_6$alkoxycarbonyl, $C_3$-$C_6$cycloalkyl, 5-8 membered monocyclic heterocycloalkyl, $C_6$-$C_{14}$aryl, or 5-8 membered monocyclicheteroaryl, in which said $C_1$-$C_6$alkyl, $C_3$-$C_6$cycloalkyl, 5-8 membered monocyclic heterocycloalkyl, $C_6$-$C_{14}$aryl, 5-8 membered monocyclic heteroaryl is optionally substituted with one or more Re, and A is —($CR_2R_2$)$_r$— or —O—; wherein r is 0, 1, 2, or 3;

each $R_2$ independently is H, —($C_1$-$C_4$)alkoxy, —($C_1$-$C_4$)alkyl optionally substituted with —($C_1$-$C_4$)alkoxy, or two of $R_2$ groups, taken together with the same carbon atom to which they are attached, form —($C_3$-$C_6$)cycloalkyl or 4-6 membered heterocyclic ring, wherein the —($C_3$-$C_6$)cycloalkyl or 4-6 membered heterocyclic ring is optionally substituted with —($C_1$-$C_4$)alkyl, —($C_1$-$C_4$)haloalkyl or oxetanyl; and the remaining variables are as defined in the first embodiment.

In a third embodiment, the invention provides a compound represented by Formula (C):

Formula (C)

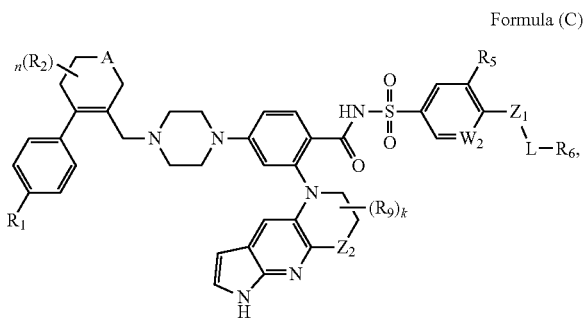

or an N-oxide thereof, or a pharmaceutically acceptable salt, solvate, polymorph, tautomer, stereoisomer, an isotopic form, or a prodrug of said compound of Formula (C) or N-oxide thereof, wherein $R_1$ is H, D, halo or —$(C_1$-$C_4)$alkyl, and the remaining variables are as defined in the first and/or second embodiments.

In a fourth embodiment, the invention provides a compound represented by Formula (D):

Formula (D)

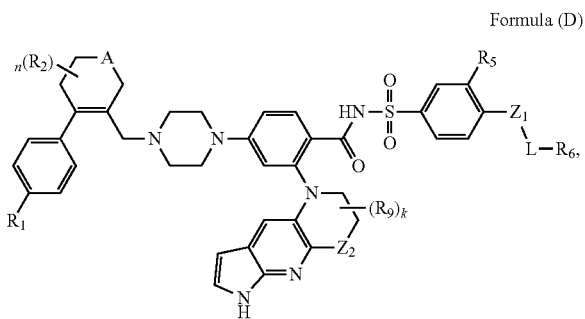

or an N-oxide thereof, or a pharmaceutically acceptable salt, solvate, polymorph, tautomer, stereoisomer, an isotopic form, or a prodrug of said compound of Formula (D) or N-oxide thereof, wherein $R_5$ independently, is nitro, halo, or —$SO_2R_a$, wherein $R_a$ of $R_5$ is —$(C_1$-$C_4)$alkyl or —$(C_1$-$C_4)$haloalkyl;

$Z_1$ is absent, NH, N(H)(CH$_2$)$_q$, O, S, or —$(C_1$-$C_4)$alkylene, wherein q is 1, 2, or 3;

L is absent or —$(C_1$-$C_4)$alkylene optionally substituted with —$(C_3$-$C_6)$cycloalkyl; and $R_6$ is H, D, —N(CH$_3$)—$(C_1$-$C_4)$alkylene-P(O)((C$_1$-C$_4$)alkoxy)$_2$, —P(O)(N(CH$_3$)$_2$)(OEt), —P(O)(O—$(C_1$-$C_4)$alkylene-O—CO—$(C_1$-$C_4)$alkyl)$_2$, —$(C_3$-$C_6)$cycloalkyl, phenyl, 5-7 membered heterocyclyl, 8-10 membered bicyclic ring, wherein the —$(C_3$-$C_6)$cycloalkyl, phenyl, 5-7 membered heterocyclyl, or 7-10 membered bicyclic ring is optionally substituted with halo, —OH, —CN, —COOH, —NH$_2$, —N(CH$_3$)$_2$, —$(C_1$-$C_4)$alkyl, —$(C_1$-$C_4)$alkoxy, cyclopropyl, 4-6 membered heterocyclyl, —CH$_2$P(O)(OH)$_2$, —CH$_2$P(O)((C$_1$-$C_4$)alkoxy)$_2$, —P(O)((C$_1$-$C_4$)alkyl)$_2$, or —N=S(O)((C$_1$-$C_4$)alkyl)$_2$, and the remaining variables are as defined in the first, second, and/or third embodiments.

In a fifth embodiment, the invention provides a compound according to Structural Formula A, B, C, or D, or an N-oxide thereof, or a pharmaceutically acceptable salt, solvate, polymorph, tautomer, stereoisomer, an isotopic form, or a prodrug of said compound of Formula A, B, C, or D, or N-oxide thereof, wherein $R_9$ independently, is D, halo, —OH, CN, —NH$_2$, =O, —$(C_1$-$C_4)$alkyl, —$(C_1$-$C_4)$alkoxy, —$(C_1$-$C_4)$ haloalkyl, —$(C_1$-$C_4)$hydroxyalkyl, —$(C_3$-$C_6)$cycloalkyl, or 1,3-dithiolanyl; and k is 0, 1, 2, 3, or 4; and the remaining variables are as defined in the first, second, third, and/or fourth embodiments.

In a sixth embodiment, the invention provides a compound according to Structural Formula A, B, C, or D, or an N-oxide thereof, or a pharmaceutically acceptable salt, solvate, polymorph, tautomer, stereoisomer, an isotopic form, or a prodrug of said compound of Formula A, B, C, or D, or N-oxide thereof, wherein A is —CH$_2$— or —O—; and the remaining variables are as defined in the first, second, third, fourth, and/or fifth embodiments.

In a seventh embodiment, the invention provides a compound according to Structural Formula A, B, C, or D, or an N-oxide thereof, or a pharmaceutically acceptable salt, solvate, polymorph, tautomer, stereoisomer, an isotopic form, or a prodrug of said compound of Formula A, B, C, or D or N-oxide thereof, wherein each $R_2$ independently is CH$_3$; and n is 0 or 2; and the remaining variables are as defined in the first, second, third, fourth, fifth and/or sixth embodiments.

In an eighth embodiment, the invention provides a compound according to Structural Formula A, B, C, or D, or an N-oxide thereof, or a pharmaceutically acceptable salt, solvate, polymorph, tautomer, stereoisomer, an isotopic form, or a prodrug of said compound of Formula A, B, C, or D, or N-oxide thereof, wherein $Z_2$ is —O—; and the remaining variables are as defined in the first, second, third, fourth, fifth, sixth and/or seventh embodiments.

In a ninth embodiment, the invention provides a compound according to Structural Formula A, B, C, or D, or an N-oxide thereof, or a pharmaceutically acceptable salt, solvate, polymorph, tautomer, stereoisomer, an isotopic form, or a prodrug of said compound of Formula A, B, C, or D, or N-oxide thereof, wherein $R_1$ is halo, such as Cl; and the remaining variables are as defined in the first, second, third, fourth, fifth, sixth, seventh, and/or eighth embodiments.

In a tenth embodiment, the invention provides a compound according to Structural Formula A, B, C, or D, or an N-oxide thereof, or a pharmaceutically acceptable salt, solvate, polymorph, tautomer, stereoisomer, an isotopic form, or a prodrug of said compound of Formula A, B, C, or D or N-oxide thereof, wherein $R_5$ is nitro; and the remaining variables are as defined in the first, second, third, fourth, fifth, sixth, seventh, eighth, and/or ninth embodiments.

In an eleventh embodiment, the invention provides a compound according to Structural Formula A, B, C, or D, or an N-oxide thereof, or a pharmaceutically acceptable salt, solvate, polymorph, tautomer, stereoisomer, an isotopic form, or a prodrug of said compound of Formula A, B, C, or D or N-oxide thereof, wherein $Z_1$ is absent, NH or O; and the remaining variables are as defined in the first, second, third, fourth, fifth, sixth, seventh, eighth, ninth, and/or tenth embodiments.

In a twelfth embodiment, the invention provides a compound according to Structural Formula A, B, C, or D, or an N-oxide thereof, or a pharmaceutically acceptable salt, solvate, polymorph, tautomer, stereoisomer, an isotopic form, or a prodrug of said compound of Formula A, B, C, or D or N-oxide thereof, wherein $Z_2$ is —O—, —CH$_2$—, —C(O)—, —NH—, —N-(oxetanyl)-, —S—, —S(O)—, —S(O$_2$)—, —S(O)(=NH)—, —S(O)(=NCH$_3$)—, or —P(O)(CH$_3$)—; and the remaining variables are as defined in the first, second, third, fourth, fifth, sixth, seventh, eighth, ninth, tenth, and/or eleventh embodiments.

In a thirteenth embodiment, the invention provides a compound according to Structural Formula A, B, C, or D, or an N-oxide thereof, or a pharmaceutically acceptable salt, solvate, polymorph, tautomer, stereoisomer, an isotopic form, or a prodrug of said compound of Formula A, B, C, or D or N-oxide thereof, wherein $R_6$ is H, D, —($C_3$-$C_6$)cycloalkyl, phenyl, tetrahydro-2H-pyranyl, or 1,4-dioxanyl, wherein the —($C_3$-$C_6$)cycloalkyl, phenyl, tetrahydro-2H-pyranyl or 1,4-dioxanyl is optionally substituted with 1 or 2 groups selected from halogen, —OH, =O, —($C_1$-$C_4$)alkyl, or —($C_1$-$C_4$)alkoxy; and the remaining variables are as defined in the first, second, third, fourth, fifth, sixth, seventh, eighth, ninth, tenth, eleventh, and/or twelfth embodiments.

In a fourteenth embodiment, the invention provides a compound according to Structural Formula A, B, C, or D, or an N-oxide thereof, or a pharmaceutically acceptable salt, solvate, polymorph, tautomer, stereoisomer, an isotopic form, or a prodrug of said compound of Formula A, B, C, or D or N-oxide thereof, wherein $R_6$ is tetrahydro-2H-pyranyl or 1,4-dioxanyl, wherein the tetrahydro-2H-pyranyl or 1,4-dioxanyl is optionally substituted with 1 or 2 halogen; and the remaining variables are as defined in the first, second, third, fourth, fifth, sixth, seventh, eighth, ninth, tenth, eleventh, twelfth, and/or thirteenth embodiments.

For example, in a compound according to Structural Formula A, B, C, or D, or an N-oxide thereof, or a pharmaceutically acceptable salt, solvate, polymorph, tautomer, stereoisomer, an isotopic form, or a prodrug of said compound of Formula A, B, C, or D or N-oxide thereof, $Z_1$ is —NH—, L is —$CH_2$—, $R_6$ is tetrahydro-2H-pyranyl or 1,4-dioxanyl optionally substituted with 1 or 2 groups of halogen, and, preferably A is —$CH_2$— or —O—, $R_1$ is Cl, $R_5$ is nitro, $Z_2$ is —O—, each $R_2$ independently is —$CH_3$ and n is 0 or 2, and $R_9$ is methyl (and k is 1) or halo (and k is 2, such as di-fluoro).

A modified compound of any one of such compounds including a modification having an improved (e.g., enhanced, greater) pharmaceutical solubility, stability, bioavailability, and/or therapeutic index as compared to the unmodified compound is also contemplated. Exemplary modifications include (but are not limited to) applicable prodrug derivatives, and deuterium-enriched compounds.

Also within the scope of this invention is a pharmaceutical composition containing one or more of the compounds (such as any one of those in Formulae (A)-(D), or a pharmaceutically acceptable salt, solvate, polymorph, tautomer, stereoisomer, an isotopic form, or a prodrug thereof or an N-oxide thereof), modifications, and/or salts thereof described herein, and a pharmaceutically acceptable diluent or carrier, for use in treating a neoplastic disease, therapeutic uses thereof, and use of the compounds for the manufacture of a medicament for treating the disease/disorder.

This invention also relates to a method of treating a neoplastic disease or an autoimmune disease by administering to a subject in need thereof an effective amount of one or more compounds of the invention (such as any one of those in Formulae (A)-(D), or a pharmaceutically acceptable salt, solvate, polymorph, tautomer, stereoisomer, an isotopic form, or a prodrug thereof or an N-oxide thereof), modifications, and/or salts thereof described herein, or a pharmaceutical composition comprising the compound(s) of the invention.

In certain embodiments, the neoplastic disease, autoimmune disease, or neorodegenerative disease is characterized by abnormal (e.g., enhanced or increased) Bcl-2 activity. For example, the neoplastic disease can be a hematological malignancy or cancer including solid tumor; the autoimmune disease can be type I diabetes; and the neorodegenerative disease can be schizophrenia.

In certain embodiments, the neoplastic disease is myeloma, multiple myeloma, lymphoma, follicular lymphoma (FL), non-Hodgkin's lymphoma, leukemia, acute leukemia, acute lymphoblastic leukemia (ALL) (such as BCL-2-dependent ALL and pediatric ALL), chronic lymphoblastic leukemia (CLL) (such as relapsed/refractory CLL, del(17p) CLL), chronic myeloid leukemia (CML) (such as blast-crisis CML), mantle cell lymphoma (MCL), diffuse large B-cell lymphoma, lung cancer such as small cell lung cancer (SCLC), melanoma, breast cancer, or prostate cancer, including drug-resistant cancer thereof.

In certain embodiments, the method further comprises administering one or more further treatment(s) effective to treat the neoplastic disease, such as surgery, radiation therapy, a chemotherapeutic agent (such as bendamustine, NL-101 (7-(5-(bis(2-chloroethyl)amino)-1-methyl-1H-benzoldlimidazol-2-yl)-N-hydroxyheptanamide), cisplatin, carboplatin, etoposide, topotecan), a target therapy (e.g., an anti-CD20 antibody such as rituximab, a Bruton's tyrosine kinase inhibitor such as ibrutinib and acalabrutinib (ACP-196), a PI3K6 inhibitor such as idelalisib); an antibody-drug conjugate or ADC (such as anti-CD30 ADC brentuximab vedotin), an immunotherapy (such as an anti-PD-1 antibody including pembrolizumab and nivolumab, or an anti-PD-L1 antibody including atezolizumab, durvalumab, and avelumab), or a CAR-T therapy (such as tisagenlecleucel, axicabtagene ciloleucel).

Also provided herein is the use of one or more compounds of the invention, or a pharmaceutically acceptable salt thereof, or a pharmaceutical composition comprising one or more compounds of the invention, for the preparation of a medicament for the treatment of the above-referenced diseases or conditions.

In another embodiment, provided herein the compounds of the invention, or a pharmaceutically acceptable salt thereof, or a pharmaceutical composition comprising one or more of the disclosed compounds are for use in treating the above-referenced diseases or conditions.

The details of one or more embodiments of the invention are set forth in the description below. Other features, objects, and advantages of the invention will be apparent from the description and from the claims. It should be understood that all embodiments/features of the invention (compounds, pharmaceutical compositions, methods of make/use, etc) described herein, including any specific features described in the examples and original claims, can combine with one another unless not applicable or explicitly disclaimed.

DETAILED DESCRIPTION OF THE INVENTION

Exemplary compounds described herein include, but are not limited to, the following:

4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl-2,2,3,3-d4)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3-methyl-2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,3-dimethyl-2,3-dihydropyrrolo[3',2':5,6]pyrido[2,3-b][1,4]oxazin-1(6H)- yl)-N-((3-nitro-4-(((tetrahydro-2H-pyran-4-yl)methyl) amino)phenyl)sulfonyl)benzamide, (R)-4-(4-((4'-chloro-5,5-dimethyl-3,4,5,6-tetrahydro-[1,1'-biphenyl]-2-yl)methyl)piperazin-1-yl)-2-(2-methyl-2,3-dihydropyrrolo[3',2':5,6]pyrido[2,3-b][1,4]oxazin-1(6H)-yl)-N-((3-nitro-4-(((tetrahydro-2H-pyran-4-yl)methyl) amino)phenyl)sulfonyl)benzamide, (S)-4-(4-((4'-chloro-5,5-dimethyl-3,4,5,6-tetrahydro-[1,1'-biphenyl]-2-yl)methyl)piperazin-1-yl)-2-(3-methyl-2,3-dihydropyrrolo[3',2':5,6]pyrido[2,3-b][1,4]oxazin-1(6H)-yl)-N-((3-nitro-4-(((tetrahydro-2H-pyran-4-yl)methyl) amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]thiazin-1(6H)-yl)-N-((3-nitro-4-(((tetrahydro-2H-pyran-4-yl)methyl)amino) phenyl)sulfonyl)benzamide, (R)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(3-(trifluoromethyl)-2,3-dihydropyrrolo[3',2':5,6]pyrido[2,3-b][1,4]oxazin-1(6H)-yl)benzamide, (R)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(3-(trifluoromethyl)-2,3-dihydropyrrolo[3',2':5,6]pyrido[2,3-b][1,4]thiazin-1(6H)-yl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl) sulfonyl)-2-(2-methyl-2,3-dihydropyrrolo[3',2':5,6] pyrido[2,3-b][1,4]oxazin-1(6H)-yl)benzamide, (S)-4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl) sulfonyl)-2-(3-methyl-2,3-dihydropyrrolo[3',2':5,6] pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-2-(2,2-dimethyl-2,3-dihydropyrrolo[3',2':5,6]pyrido[2,3-b][1,4]oxazin-1(6H)-yl)-N-((4-(((4-fluorotetrahydro-2H-pyran-4-yl)methyl) amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl) sulfonyl)-2-(2'H-spiro[cyclopropane-1,3'-pyrrolo[3',2':5, 6]pyrido[2,3-b][1,4]oxazin]-1'(6'H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl) sulfonyl)-2-(2,3,4,6-tetrahydro-1H-pyrrolo[2,3-b][1,5] naphthyridin-1-yl)benzamide, 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl) sulfonyl)-2-(2-oxo-2,3,4,6-tetrahydro-1H-pyrrolo[2,3-b] [1,5]naphthyridin-1-yl)benzamide, 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl) sulfonyl)-2-(3-oxo-2,3-dihydropyrrolo[3',2':5,6]pyrido[2, 3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl) sulfonyl)-2-(4-oxo-2,3,4,6-tetrahydro-1H-pyrrolo[2,3-b] [1,5]naphthyridin-1-yl)benzamide, 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl) sulfonyl)-2-(2,3,4,6-tetrahydro-1H-pyrrolo[3',2':5,6] pyrido[2,3-b]pyrazin-1-yl)benzamide, 4-(4-((4'-chloro-5,5-dimethyl-3,4,5,6-tetrahydro-[1,1'-biphenyl]-2-yl)methyl)piperazin-1-yl)-2-(4,4-dioxido-2,3-dihydropyrrolo[3',2':5,6]pyrido[2,3-b][1,4]thiazin-1(6H)-yl)-N-((4-(((4-fluorotetrahydro-2H-pyran-4-yl)methyl) amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl) sulfonyl)-2-(4-(methylimino)-4-oxido-2,3,4,6-tetrahydro-1H-4$\lambda$,4-pyrrolo[3',2':5,6]pyrido[2,3-b][1,4] thiazin-1-yl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((tetrahydro-2H-pyran-3-yl)methyl)amino) phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-((2-morpholinoethyl)amino)-3-nitrophenyl)sulfonyl) benzamide, (R)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((4-methylmorpholin-2-yl)methyl)amino)-3-nitrophenyl)sulfonyl)benzamide, (R)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((4-(oxetan-3-yl)morpholin-2-yl)methyl)amino) phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((4-hydroxycyclohexyl)methyl)amino)-3-nitrophenyl) sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((((1r,4r)-4-methoxycyclohexyl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((((1s,4s)-4-hydroxy-4-methylcyclohexyl)methyl) amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((((1s,4s)-4-ethyl-4-hydroxycyclohexyl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-((1-(tetrahydro-2H-pyran-4-yl)piperidin-4-yl) amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((1s,4s)-4-morpholinocyclohexyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((4-((4-(cyclopropylamino)cyclohexyl)amino)-3-nitrophenyl)sulfonyl)-2-(2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((4,4-difluorocyclohexyl)methyl)amino)-3-nitrophenyl)sulfonyl)-2-(2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-((tetrahydro-2H-pyran-4-yl)methoxy)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-((tetrahydro-2H-pyran-3-yl)methoxy)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(2-morpholinoethoxy)-3-nitrophenyl)sulfonyl)benzamide, (S)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-((4-methylmorpholin-2-yl)methoxy)-3-nitrophenyl)sulfonyl)benzamide, (S)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-((4-(oxetan-3-yl)morpholin-2-yl)methoxy)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-((4-hydroxycyclohexyl)methoxy)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((1r,4s)-4-methoxycyclohexyl)methoxy)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((1s,4s)-4-hydroxy-4-methylcyclohexyl)methoxy)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((1s,4s)-4-ethyl-4-hydroxycyclohexyl)methoxy)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-((1-(tetrahydro-2H-pyran-4-yl)piperidin-4-yl)oxy)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((1s,4s)-4-morpholinocyclohexyl)oxy)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((4-((4-(cyclopropylamino)cyclohexyl)oxy)-3-nitrophenyl)sulfonyl)-2-(2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-N-((4-((4,4-difluorocyclohexyl)methoxy)-3-nitrophenyl)sulfonyl)-2-(2,3-dihydropyrrolo[3',2':5,6]pyrido[2,3-b][1,4]oxazin-1(6H)-yl)benzamide, 4-(4-((2-(4-chlorophenyl)cyclopent-1-en-1-yl)methyl)piperazin-1-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, 4-(4-((2-(4-chlorophenyl)cyclohept-1-en-1-yl)methyl)piperazin-1-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, 4-(4-((4-(4-chlorophenyl)-6,6-dimethyl-5,6-dihydro-2H-pyran-3-yl)methyl)piperazin-1-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, 4-(4-((4'-chloro-4-(methoxymethyl)-4-methyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-5-fluoro-N-((4-(((4-fluorotetrahydro-2H-pyran-4-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((6-(((4-fluorotetrahydro-2H-pyran-4-yl)methyl)amino)-5-nitropyridin-3-yl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-((trifluoromethyl)sulfonyl)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(6,7-dihydroimidazo[4',5':5,6]pyrido[2,3-b][1,4]oxazin-8(3H)-yl)-N-((3-nitro-4-(((tetrahydro-2H-pyran-4-yl)methyl)amino)phenyl)sulfonyl)benzamide, 4-(4-((9-(4-chlorophenyl)-3-methyl-3-azaspiro[5.5]undec-8-en-8-yl)methyl)piperazin-1-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, 4-(4-((9-(4-chlorophenyl)-3-(1,3-difluoropropan-2-yl)-3-azaspiro[5.5]undec-8-en-8-yl)methyl)piperazin-1-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, 4-(4-((4'-chloro-5,5-difluoro-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((4- fluorotetrahydro-2H-pyran-4-yl)methyl)amino)-3-nitrophenyl)sulfonyl)benzamide, 4-(4-((5-(4-chlorophenyl)spiro[2.5]oct-5-en-6-yl)methyl)piperazin-1-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, 4-(4-((7-(4-chlorophenyl)spiro[3.5]non-6-en-6-yl)methyl)piperazin-1-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, 4-(4-((4'-chloro-3'-fluoro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, 4-(4-((4'-chloro-3',5,5-trimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, 2-(2,3-dihydropyrrolo[3',2':5,6]pyrido[2,3-b][1,4]oxazin-1(6H)-yl)-4-(4-((4,4-dimethyl-2-(pyridin-3-yl)cyclohex-1-en-1-yl)methyl)piperazin-1-yl)-N-((3-nitro-4-(((tetrahydro-2H-pyran-4-yl)methyl)amino)phenyl)sulfonyl)benzamide, 4-(4-((2-(1H-indol-5-yl)-4,4-dimethylcyclohex-1-en-1-yl)methyl)piperazin-1-yl)-2-(2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, (R)—N-((4-(((1,4-dioxan-2-yl)methyl)amino)-3-fluoro-5-nitrophenyl)sulfonyl)-4-(4-((6-(4-chlorophenyl)spiro[3.5]non-6-en-7-yl)methyl)piperazin-1-yl)-2-(2,3-dihydropyrrolo[3',2':5,6]pyrido[2,3-b][1,4]oxazin-1(6H)-yl)benzamide, (R)—N-((4-(((1,4-dioxan-2-yl)methyl)amino)-3-nitrophenyl)sulfonyl)-4-(4-((6-(4-chlorophenyl)spiro[3.5]non-6-en-7-yl)methyl)piperazin-1-yl)-2-(2,3-dihydropyrrolo[3',2':5,6]pyrido[2,3-b][1,4]oxazin-1(6H)-yl)benzamide, (R)—N-((4-(((1,4-dioxan-2-yl)methyl)amino)-3-nitrophenyl)sulfonyl)-4-(4-((6-(4-chlorophenyl)-2-oxaspiro[3.5]non-6-en-7-yl)methyl)piperazin-1-yl)-2-(2,3-dihydropyrrolo[3',2':5,6]pyrido[2,3-b][1,4]oxazin-1(6H)-yl)benzamide, (R)—N-((4-(((1,4-dioxan-2-yl)methyl)amino)-3-fluoro-5-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzamide, 4-(4-((6-(4-chlorophenyl)-2-oxaspiro[3.5]non-6-en-7-yl)methyl)piperazin-1-yl)-2-(2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, 4-(4-((6-(4-chlorophenyl)-2-oxaspiro[3.5]non-6-en-7-yl)methyl)piperazin-1-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, (S)—N-((4-(((1,4-dioxan-2-yl)methyl)amino)-3-nitrophenyl)sulfonyl)-4-(4-((6-(4-chlorophenyl)spiro[3.5]non-6-en-7-yl)methyl)piperazin-1-yl)-2-(2,3-dihydropyrrolo[3',2':5,6]pyrido[2,3-b][1,4]oxazin-1(6H)-yl)-6-fluorobenzamide, (S)—N-((4-(((1,4-dioxan-2-yl)methyl)amino)-3-nitrophenyl)sulfonyl)-4-(4-((6-(4-chlorophenyl)spiro[3.5]non-6-en-7-yl)methyl)piperazin-1-yl)-2-(2,3-dihydropyrrolo[3',2':5,6]pyrido[2,3-b][1,4]oxazin-1(6H)-yl)-5-fluorobenzamide, 4-(4-((4'-chloro-5,5-bis(methyl-d3)-3,4,5,6-tetrahydro-[1,1'-biphenyl]-2-yl)methyl)-2-methylpiperazin-1-yl-2,3,3,5,5,6,6-d7)-2-(2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, diethyl ((2-(((4-(N-(4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzoyl)sulfamoyl)-2-nitrophenyl)amino)methyl)morpholino)methyl)phosphonate, diethyl (((3-((4-(N-(4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzoyl)sulfamoyl)-2-nitrophenyl)amino)propyl)(methyl)amino)methyl)phosphonate, 2-(((24(4-(N-(4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzoyl)sulfamoyl)-2-nitrophenyl)amino)ethyl)((pivaloyloxy)methoxy)phosphoryl)oxy)ethyl pivalate, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((1-methyl-1-oxidophosphinan-4-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((1-hydroxy-1-oxidophosphinan-4-yl)methyl)amino)-3-nitrophenyl)sulfonyl)benzamide, ((4-(((4-(N-(4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzoyl)sulfamoyl)-2-nitrophenyl)amino)methyl)-1-oxidophosphinan-1-yl)oxy)methyl pivalate, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((2-methyl-2-oxido-1,3,2-oxazaphosphinan-5-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-((2-(2-methyl-2-oxido-1,3,2-oxazaphosphinan-3-yl)ethyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((1-(dimethylphosphoryl)piperidin-4-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-(dimethylphosphoryl)-4-(((tetrahydro-2H-pyran-4-yl)methyl)amino)phenyl)sulfonyl)benzamide, N-((4-(((1,4-dioxaspiro[4.5]decan-8-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzamide, N-((4-(((2-oxaspiro[3.5]nonan-7-yl)methyl)amino)-3-nitrophenyl)sulfonyl)-4-(4-((4'-chloro-5,5-dimethyl-3,4,5,6- tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-((2-(hexahydrofuro[3,4-c]pyridin-5(3H)-yl)ethyl)amino)-3-nitrophenyl)sulfonyl)benzamide, (R)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-((2-(3-oxooctahydro-7H-imidazo[1,5-d][1,4]diazepin-7-yl)ethyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-((2-(3-oxooctahydro-5H-pyrrolo[3,4-c]pyridin-5-yl)ethyl)amino)phenyl)sulfonyl)benzamide, N-((4-((2-(2-oxa-5-azabicyclo[2.2.2]octan-5-yl)ethyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((3-hydroxy-3-methylbicyclo[3.1.1]heptan-6-yl)methyl)amino)-3-nitrophenyl)sulfonyl)benzamide, N-(4-((2-(2-oxa-5-azabicyclo[2.2.1]heptan-5-yl)ethyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzamide, 2-((3R)-8-(2-((4-(N-(4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzoyl)sulfamoyl)-2-nitrophenyl)amino)ethyl)-6,6-difluoro-8-azabicyclo[3.2.1]octan-3-yl)acetic acid, 4-(4-((4'-chloro-5,5-dimethyl-3,4,5,6-tetrahydro-[1,1'-biphenyl]-2-yl)methyl)piperazin-1-yl)-N-((4-((2-(6,6-difluoro-8-azabicyclo[3.2.1]octan-8-yl)ethyl)amino)-3-nitrophenyl)sulfonyl)-2-(2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-((2-(tetrahydro-2H-pyran-4-yl)-2-azaspiro[3.3]heptan-6-yl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((tetrahydro-2H-thiopyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((1-imino-1-oxidohexahydro-1l6-thiopyran-4-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-((4-(methylsulfonyemorpholin-2-yl)methyl)amino)-3-nitrophenyl)sulfonyl)benzamide, N-((4-(((4-aminotetrahydro-2H-pyran-4-yl)methyl)amino)-3-nitrophenyl)sulfonyl)-4-(4-((4'-chloro-5,5-dimethyl-3, 4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-((1-(tetrahydro-2H-pyran-4-yl)cyclopropyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((4-((2-(5,6-dihydroimidazo[1,2-a]pyrazin-7(8H)-yl)ethyl)amino)-3-nitrophenyl)sulfonyl)-2-(2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((5,6,7,8-tetrahydroimidazo[1,2-a]pyridin-6-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((4-(((3-(difluoromethoxy)benzyl)amino)-3-nitrophenyl)sulfonyl)-2-(2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((3,4,5-trihydroxytetrahydrofuran-2-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((3,4,5,6-tetrahydroxytetrahydro-2H-pyran-2-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((4,5-dihydroxy-6,6-dimethyltetrahydro-2H-pyran-2-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((2,3,5-trihydroxy-6-(hydroxymethyl)tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((2,3,4,5,6-pentahydroxycyclohexyl)methyl)amino)phenyl)sulfonyl)benzamide (R)—N-((4-(((1,4-dioxan-2-yl)methyl)amino)-3-nitrophenyl)sulfonyl)-4-(1-((4'-chloro-5,5-dimethyl-3,4,5,6-tetrahydro-[1,1'-biphenyl]-2-yl)methyl)-1,2,3,6-tetrahydropyridin-4-yl)-2-(2,3-dihydropyrrolo[3',2':5,6]pyrido[2,3-b][1,4]oxazin-1(6H)-yl)benzamide, 4-(1-((6-(4-chlorophenyl)spiro[3.5]non-6-en-7-yl)methyl)-1,2,3,6-tetrahydropyridin-4-yl)-2-(2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, (R)—N-((4-(((1,4-dioxan-2-yl)methyl)amino)-3-nitrophenyl)sulfonyl)-4-(1-((4'-chloro-5,5-dimethyl-3,4,5,6-tetrahydro-[1,1'-biphenyl]-2-yl)methyl)piperidin-4-yl)-2-(2,3-dihydropyrrolo[3',2':5,6]pyrido[2,3-b][1,4]oxazin-1(6H)-yl)benzamide, (S)—N-((4-(((1,4-dioxan-2-yl)methyl)amino)-3-nitrophenyl)sulfonyl)-5-(4-((6-(4-chlorophenyl)spiro[3.5]non-6- en-7-yl)methyl)piperazin-1-yl)-3-(2,3-dihydropyrrolo[3',2':5,6]pyrido[2,3-b][1,4]oxazin-1(6H)-yl)picolinamide, (S)—N-((4-(((1,4-dioxan-2-yl)methyl)amino)-3-nitrophenyl)sulfonyl)-6-(4-(((6-(4-chlorophenyl)spiro[3.5]non-6-en-7-yl)methyl)piperazin-1-yl)-2-(2,3-dihydropyrrolo[3',2':5,6]pyrido[2,3-b][1,4]oxazin-1(6H)-yl)nicotinamide, 4-(4-((4'-chloro-5,5-dimethyl-3,4,5,6-tetrahydro-[1,1'-biphenyl]-2-yl)methyl)piperazin-1-yl)-2-(2-methyl-2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,2-dimethyl-2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3-(hydroxymethyl)-2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, (S)-4-(4-((4'-chloro-5,5-dimethyl-3,4,5,6-tetrahydro-[1,1'-biphenyl]-2-yl)methyl)piperazin-1-yl)-2-(2-methyl-2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, (R)-4-(4-((4'-chloro-5,5-dimethyl-3,4,5,6-tetrahydro-[1,1'-biphenyl]-2-yl)methyl)piperazin-1-yl)-2-(3-methyl-2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(4,4-dioxido-2,3-dihydropyrrolo[3',2':5,6]pyrido[2,3-b][1,4]thiazin-1(6H)-yl)-N-((3-nitro-4-(((tetrahydro-2H-pyran-4-yl)methyl)amino)phenyl)sulfonyl)benzamide, (S)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(3-(trifluoromethyl)-2,3-dihydropyrrolo[3',2':5,6]pyrido[2,3-b][1,4]oxazin-1(6H)-yl)benzamide, (S)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(3-(trifluoromethyl)-2,3-dihydropyrrolo[3',2':5,6]pyrido[2,3-b][1,4]thiazin-1(6H)-yl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl-2,2,3,3-d4)-N-((4-(((4-fluorotetrahydro-2H-pyran-4-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(3-methyl-2,3-dihydropyrrolo[3',2':5,6]pyrido[2,3-b][1,4]oxazin-1(6H)-yl)benzamide, (R)-4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(3-methyl-2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-2-(3,3-dimethyl-2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(3'H-spiro[cyclopropane-1,2'-pyrrolo[3',2':5,6]pyrido[2,3-b][1,4]oxazin]-1'(6'H)-yl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]thiazin-1(6H)-yl)-N-((4-(((4-fluorotetrahydro-2H-pyran-4-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(2-oxo-2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(3-oxo-2,3,4,6-tetrahydro-1H-pyrrolo[3',2':5,6]pyrido[2,3-b]pyrazin-1-yl)benzamide, 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(4-oxo-4,6-dihydro-1H-pyrrolo[2,3-b][1,5]naphthyridin-1-yl)benzamide, 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(4-methyl-2,3,4,6-tetrahydro-1H-pyrrolo[3',2':5,6]pyrido[2,3-b]pyrazin-1-yl)benzamide, 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(4-imino-4-oxido-2,3,4,6-tetrahydro-1H-4λ,4-pyrrolo[3',2':5,6]pyrido[2,3-b][1,4]thiazin-1-yl)benzamide, 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(4-methyl-4-oxido-2,3,6-trihydropyrrolo[3',2':5,6]pyrido[3,2-b][1,4]azaphosphinin-1-yl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((3-fluorotetrahydro-2H-pyran-3-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-((3-morpholinopropyl)amino)-3-nitrophenyl)sulfonyl)benzamide, (S)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((4-methylmorpholin-2-yl)methyl)amino)-3-nitrophenyl)sulfonyl)benzamide, (S)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((4-(oxetan-3-yl)morpholin-2-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((4-hydroxy-4-methylcyclohexyl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(4(1s,4s)-4-methoxycyclohexyl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(4(1r,4r)-4-hydroxy-4-methylcyclohexyl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(4(1r,4r)-4-ethyl-4-hydroxycyclohexyl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-((1-(oxetan-3-yl)piperidin-4-yl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((1r,4r)-4-morpholinocyclohexyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-((4-(methyl(oxetan-3-yl)amino)cyclohexyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((1,4,4-trifluorocyclohexyl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-((4-fluorotetrahydro-2H-pyran-4-yl)methoxy)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-((3-fluorotetrahydro-2H-pyran-3-yl)methoxy)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(3-morpholinopropoxy)-3-nitrophenyl)sulfonyl)benzamide, (R)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-((4-methylmorpholin-2-yl)methoxy)-3-nitrophenyl)sulfonyl)benzamide, (R)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-((4-(oxetan-3-yl)morpholin-2-yl)methoxy)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-((4-hydroxy-4-methylcyclohexyl)methoxy)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((1s,4s)-4-methoxycyclohexyl)methoxy)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((1r,4r)-4-hydroxy-4-methylcyclohexyl)methoxy)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((1r,4r)-4-ethyl-4-hydroxycyclohexyl)methoxy)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-((1-(oxetan-3-yl)piperidin-4-yl)oxy)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((1r,4r)-4-morpholinocyclohexyl)oxy)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-((4-(methyl(oxetan-3-yl)amino)cyclohexyl)oxy)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-((1,4,4-trifluorocyclohexyl)methoxy)phenyl)sulfonyl)benzamide, 4-(4-((4-(4-chlorophenyl)-5,6-dihydro-2H-pyran-3-yl)methyl)piperazin-1-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, (Z)-4-(4-((2-(4-chlorophenyl)cyclooct-1-en-1-yl)methyl)piperazin-1-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, 4-(4-((4'-chloro-4-methoxy-4-methyl-3,4,5,6-tetrahydro-[1,1'-biphenyl]-2-yl)methyl)piperazin-1-yl)-2-(2,3-dihydropyrrolo[3',2':5,6]pyrido[2,3-b][,4]oxazin-1(6H)-yl)-N-((4-(((4-fluorotetrahydro-2H-pyran-4-yl)methyl)amino)-3-nitrophenyl)sulfonyl)benzamide, 4-(5-((4'-chloro-5,5-dimethyl-3,4,5,6-tetrahydro-[1,1'-biphenyl]-2-yl)methyl)-2,5-diazabicyclo[2.2.2]octan-2-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-(4-(((4-fluorotetrahydro-2H-pyran-4-yl)methyl)amino)-3-nitrophenylsulfonimidoyl)benzamide, 4-(4-((4'-chloro-5,5-dimethyl-3,4,5,6-tetrahydro-[1,1'-biphenyl]-2-yl)methyl)piperazin-1-yl)-N-((5-chloro-6-((tetrahydro-2H-pyran-4-yl)methoxy)pyridin-3-yl)sulfonyl)-2-(2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-

(((4-fluorotetrahydro-2H-pyran-4-yl)methyl)amino)-3-(S-(trifluoromethyl)sulfonimidoyl)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydro-[1,4]oxazino[3,2-f]indol-1(6H)-yl)-N-((3-nitro-4-(((tetrahydro-2H-pyran-4-yl)methyl)amino)phenyl)sulfonyl)benzamide, 4-(4-((9-(4-chlorophenyl)-3-isopropyl-3-azaspiro[5.5]undec-8-en-8-yl)methyl)piperazin-1-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, 4-(4-((9-(4-chlorophenyl)-3-(oxetan-3-yl)-3-azaspiro[5.5]undec-8-en-8-yl)methyl)piperazin-1-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, 4-(4-((4'-chloro-5,5-bis(fluoromethyl)-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, 4-(4-(1-(4'-chloro-5,5-dimethyl-3,4,5,6-tetrahydro-[1,1'-biphenyl]-2-yl)cyclopropyl)piperazin-1-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, 4-(4-((6-(4-chlorophenyl)spiro[2.5]oct-5-en-5-yl)methyl)piperazin-1-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, 4-(4-((4'-chloro-2'-fluoro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, 4-(4-((4'-chloro-2',5,5-trimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, 2-(2,3-dihydropyrrolo[3',2':5,6]pyrido[2,3-b][1,4]oxazin-1(6H)-yl)-4-(4-((4,4-dimethyl-2-(pyridin-2-yl)cyclohex-1-en-1-yl)methyl)piperazin-1-yl)-N-((3-nitro-4-(((tetrahydro-2H-pyran-4-yl)methyl)amino)phenyl)sulfonyl)benzamide, 2-(2,3-dihydropyrrolo[3',2':5,6]pyrido[2,3-b][1,4]oxazin-1(6H)-yl)-4-(4-((4,4-dimethyl-2-(1H-pyrrolo[2,3-b]pyridin-5-yl)cyclohex-1-en-1-yl)methyl)piperazin-1-yl)-N-((3-nitro-4-(((tetrahydro-2H-pyran-4-yl)methyl)amino)phenyl)sulfonyl)benzamide, (S)—N-((4-(((1,4-dioxan-2-yl)methyl)amino)-3-fluoro-5-nitrophenyl)sulfonyl)-4-(4-((6-(4-chlorophenyl)spiro[3.5]non-6-en-7-yl)methyl)piperazin-1-yl)-2-(2,3-dihydropyrrolo[3',2':5,6]pyrido[2,3-b][1,4]oxazin-1(6H)-yl)benzamide, (S)—N-((4-(((1,4-dioxan-2-yl)methyl)amino)-3-nitrophenyl)sulfonyl)-4-(4-((6-(4-chlorophenyl)spiro[3.5]non-6-en-7-yl)methyl)piperazin-1-yl)-2-(2,3-dihydropyrrolo[3',2':5,6]pyrido[2,3-b][1,4]oxazin-1(6H)-yl)benzamide, (S)—N-((4-(((1,4-dioxan-2-yl)methyl)amino)-3-nitrophenyl)sulfonyl)-4-(4-((6-(4-chlorophenyl)-2-oxaspiro[3.5]non-6-en-7-yl)methyl)piperazin-1-yl)-2-(2,3-dihydropyrrolo[3',2':5,6]pyrido[2,3-b][1,4]oxazin-1(6H)-yl)benzamide, (S)—N-((4-(((1,4-dioxan-2-yl)methyl)amino)-3-fluoro-5-nitrophenyl)sulfonyl)-4-(4-44'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzamide, 4-(4-((6-(4-chlorophenyl)spiro[3.5]non-6-en-7-yl)methyl)piperazin-1-yl)-2-(2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, 4-(4-((6-(4-chlorophenyl)spiro[3.5]non-6-en-7-yl)methyl)piperazin-1-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, (S)—N-((4-(((1,4-dioxan-2-yl)methyl)amino)-3-nitrophenyl)sulfonyl)-4-(4-((6-(4-chlorophenyl)spiro[3.5]non-6-en-7-yl)methyl)piperazin-1-yl)-2-(2,3-dihydropyrrolo[3',2':5,6]pyrido[2,3-b][1,4]oxazin-1(6H)-yl)-3-fluorobenzamide, (S)—N-((4-(((1,4-dioxan-2-yl)methyl)amino)-3-fluoro-5-nitrophenyl)sulfonyl)-4-(4-((6-(4-chlorophenyl)spiro[3.5]non-6-en-7-yl)methyl)piperazin-1-yl)-2-(2,3-dihydropyrrolo[3',2':5,6]pyrido[2,3-b][1,4]oxazin-1(6H)-yl)-6-fluorobenzamide, 4-(4-((4'-chloro-5,5-bis(methyl-d3)-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl-2,2,3,3-d4)-N-((3-nitro-4-(((tetrahydro-2H-pyran-4-yl)methyl)amino)phenyl)sulfonyl)benzamide, ((2-(((4-(N-(4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzoyl)sulfamoyl)-2-nitrophenyl)amino)methyl)morpholino)methyl)phosphonic acid, diethyl (2-((2-((4-(N-(4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzoyl)sulfamoyl)-2-nitrophenyl)amino)ethyl)(methyl)amino)ethyl)phosphonate, ethyl P-(2-((4-(N-(4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzoyl)sulfamoyl)-2-nitrophenyl)amino)ethyl)-N,N-dimethylphosphonamidate, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((1-(dimethylamino)-1-oxidophosphinan-4-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((1-ethoxy-1-oxidophosphinan-4-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((1-isopropoxy-1-oxidophosphinan-4-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((1,2,3-trimethyl-2-oxido-1,3,2-diazaphosphinan-5-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-((2-(2-methyl-2-oxido-1,3,2-diazaphosphinan-1-yl)ethyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((4-(dimethylphosphoryl)morpholin-2-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(dimethylphosphoryl)-3-nitrophenyl)sulfonyl)benzamide, N-((4-(((1,4-dithiaspiro[4.5]decan-8-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzamide, N-((4-((2-(6-azaspiro[2.5]octan-6-yl)ethyl)amino)-3-nitrophenyl)sulfonyl)-4-(4-44'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-N-((4-((2-(2,2-difluoro-7-azaspiro[3.5]nonan-7-yl)ethyl)amino)-3-nitrophenyl)sulfonyl)-2-(2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-((2-(2-(oxetan-3-yl)octahydro-5H-pyrrolo[3,4-c]pyridin-5-yl)ethyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-((2-(1-oxooctahydro-5H-pyrrolo[3,4-c]pyridin-5-yl)ethyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-((3-hydroxybicyclo[3.1.1]heptan-6-yl)methyl)amino)-3-nitrophenyl)sulfonyl)benzamide, N-((4-(((3-amino-3-methylbicyclo[3.1.1]heptan-6-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-((2-(5-(oxetan-3-yl)-2,5-diazabicyclo[2.2.1]heptan-2-yl)ethyl)amino)phenyl)sulfonyl)benzamide, 2-((3S)-8-(2-((4-(N-(4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzoyl)sulfamoyl)-2-nitrophenyl)amino)ethyl)-6,6-difluoro-8-azabicyclo[3.2.1]octan-3-yl)acetic acid, 4-(4-((4'-chloro-5,5-dimethyl-3,4,5,6-tetrahydro-[1,1'-biphenyl]-2-yl)methyl)piperazin-1-yl)-N-((4-((2-(6,6-difluoro-8-azabicyclo[3.2.1]octan-8-yl)ethyl)amino)-3-nitrophenyl)sulfonyl)-2-(2,3-dihydropyrrolo[3',2':5,6]pyrido[2,3-b][1,4]oxazin-1(6H)-yl)benzamide, N-((4-((7-oxaspiro[3.5]nonan-2-yl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((1,1-dioxidotetrahydro-2H-thiopyran-4-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((1-(isopropylimino)-1-oxidohexahydro-1l6-thiopyran-4-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((4-(S-methylsulfonimidoyl)morpholin-2-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((4-(((4-cyanotetrahydro-2H-pyran-4-yl)methyl)amino)-3-nitrophenyl)sulfonyl)-2-(2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-((2-(tetrahydro-2H-pyran-4-yl)propan-2-yl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((4-((2-(5,6-dihydro-[1,2,4]triazolo[1,5-a]pyrazin-7(8H)-yl)ethyl)amino)-3-nitrophenyl)sulfonyl)-2-(2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((1-(thiazol-2-yl)piperidin-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((4-((4-(difluoromethoxy)benzyl)amino)-3-nitrophenyl)sulfonyl)-2-(2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((3,5-dihydroxytetrahydrofuran-2-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((3,4,5-trihydroxy-6,6-dimethyltetrahydro-2H-pyran-2-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((2,3,5-trihydroxytetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((3,4,5-trihydroxy-6-(methylthio)tetrahydro-2H-pyran-2-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((3,4,5-trihydroxy-6-(((4,5,6-trihydroxy-2-

(hydroxymethyl)tetrahydro-2H-pyran-3-yl)methoxy)
methyl)tetrahydro-2H-pyran-2-yl)methyl)amino)phenyl)
sulfonyl)benzamide,
N-((4-(((1,4-dioxan-2-yl)methyl)amino)-3-nitrophenyl)
sulfonyl)-4-(1-((6-(4-chlorophenyl)-2-oxaspiro[3.5]non-
6-en-7-yl)methyl)-1,2,3,6-tetrahydropyridin-4-yl)-2-(2,3-
dihydropyrrolo[3',2':5,6]pyrido[2,3-b][1,4]oxazin-1(6H)-
yl)benzamide,
4-(1-((6-(4-chlorophenyl)-2-oxaspiro[3.5]non-6-en-7-yl)
methyl)-1,2,3,6-tetrahydropyridin-4-yl)-2-(2,3-dihydro-
pyrrolo[3',2':5,6]pyrido[2,3-b][1,4]oxazin-1(6H)-yl)-N-
((3-nitro-4-(((tetrahydro-2H-pyran-4-yl)methyl)amino)
phenyl)sulfonyl)benzamide,
(R)-4-(1-((4'-chloro-5,5-dimethyl-3,4,5,6-tetrahydro-[1,1'-
biphenyl]-2-yl)methyl)piperidin-4-yl)-2-(2,3-dihydropyr-
rolo[3',2':5,6]pyrido[2,3-b][1,4]oxazin-1(6H)-yl)-N-((3-
nitro-4-(((tetrahydro-2H-pyran-3-yl)methyl)amino)
phenyl)sulfonyl)benzamide,
(S)-6-(4-((6-(4-chlorophenyl)-2-oxaspiro[3.5]non-6-en-7-
yl)methyl)piperazin-1-yl)-4-(2,3-dihydropyrrolo[3',2':5,
6]pyrido[2,3-b][1,4]oxazin-1(6H)-yl)-N-((3-nitro-4-
(((tetrahydro-2H-pyran-3-yl)methyl)amino)phenyl)
sulfonyl)nicotinamide,
(S)—N-((4-(((1,4-dioxan-2-yl)methyl)amino)-3-nitrophe-
nyl)sulfonyl)-6-(4-((4'-chloro-5,5-dimethyl-3,4,5,6-tetra-
hydro-[1,1'-biphenyl]-2-yl)methyl)piperazin-1-yl)-2-(2,
3-dihydropyrrolo[3',2':5,6]pyrido[2,3-b][1,4]oxazin-1
(6H)-yl)nicotinamide,
N-((4-((((R)-1,4-dioxan-2-yl)methyl)amino)-3-nitrophenyl)
sulfonyl)-4-(4-((4'-chloro-5,5-dimethyl-3,4,5,6-tetra-
hydro-[1,1'-biphenyl]-2-yl)methyl)piperazin-1-yl)-24(S)-
3-methyl-2,3-dihydropyrrolo[3',2':5,6]pyrido[2,3-b][1,4]
oxazin-1(6H)-yl)benzamide,
4-(4-((4'-chloro-5,5-dimethyl-3,4,5,6-tetrahydro-[1,1'-bi-
phenyl]-2-yl)methyl)piperazin-1-yl)-N-((4-((((S)-2-
fluoro-1,4-dioxan-2-yl)methyl)amino)-3-nitrophenyl)
sulfonyl)-2-((S)-3-methyl-2,3-dihydropyrrolo[3',2':5,6]
pyrido[2,3-b][1,4]oxazin-1(6H)-yl)benzamide,
(R)—N-((4-(((1,4-dioxan-2-yl)methyl)amino)-3-nitrophe-
nyl)sulfonyl)-4-(4-((4'-chloro-5,5-dimethyl-3,4,5,6-tetra-
hydro-[1,1'-biphenyl]-2-yl)methyl)piperazin-1-yl)-2-(2,
3-dihydropyrrolo[3',2':5,6]pyrido[2,3-b][1,4]oxazin-1
(6H)-yl)benzamide,
(S)-4-(4-((4'-chloro-5,5-dimethyl-3,4,5,6-tetrahydro-[1,1'-
biphenyl]-2-yl)methyl)piperazin-1-yl)-2-(2,3-dihydropy-
rrolo[3',2':5,6]pyrido[2,3-b][1,4]oxazin-1(6H)-yl)-N-((4-
(((2-fluoro-1,4-dioxan-2-yl)methyl)amino)-3-
nitrophenyl)sulfonyl)benzamide,
(R)—N-((4-(((1,4-dioxan-2-yl)methyl)amino)-3-nitrophe-
nyl)sulfonyl)-4-(4-((4'-chloro-5,5-dimethyl-3,4,5,6-tetra-
hydro-[1,1'-biphenyl]-2-yl)methyl)piperazin-1-yl)-2-(3,
3-difluoro-2,3-dihydropyrrolo[3',2':5,6]pyrido[2,3-b][1,
4]oxazin-1(6H)-yl)benzamide,
(S)-4-(4-((4'-chloro-5,5-dimethyl-3,4,5,6-tetrahydro-[1,1'-
biphenyl]-2-yl)methyl)piperazin-1-yl)-2-(3,3-difluoro-2,
3-dihydropyrrolo[3',2':5,6]pyrido[2,3-b][1,4]oxazin-1
(6H)-yl)-N-((4-(((2-fluoro-1,4-dioxan-2-yl)methyl)
amino)-3-nitrophenyl)sulfonyl)benzamide,
4-(4-((4'-chloro-5,5-dimethyl-3,4,5,6-tetrahydro-[1,1'-bi-
phenyl]-2-yl)methyl)piperazin-1-yl)-2-(3,3-difluoro-2,3-
dihydropyrrolo[3',2':5,6]pyrido[2,3-b][1,4]oxazin-1(6H)-
yl)-N-((3-nitro-4-(((tetrahydro-2H-pyran-4-yl)methyl)
amino)phenyl)sulfonyl)benzamide,
N-((4-((((S)-1,4-dioxan-2-yl)methyl)amino)-3-nitrophenyl)
sulfonyl)-4-(4-((4'-chloro-5,5-dimethyl-3,4,5,6-tetra-
hydro-[1,1'-biphenyl]-2-yl)methyl)piperazin-1-yl)-2-
((S)-3-methyl-2,3-dihydropyrrolo[3',2':5,6]pyrido[2,3-b]
[1,4]oxazin-1(6H)-yl)benzamide,
4-(4-((4'-chloro-5,5-dimethyl-3,4,5,6-tetrahydro-[1,1'-bi-
phenyl]-2-yl)methyl)piperazin-1-yl)-N-((4-4((R)-2-
fluoro-1,4-dioxan-2-yl)methyl)amino)-3-nitrophenyl)
sulfonyl)-2-((S)-3-methyl-2,3-dihydropyrrolo[3',2':5,6]
pyrido[2,3-b][1,4]oxazin-1(6H)-yl)benzamide,
(S)—N-((4-(((1,4-dioxan-2-yl)methyl)amino)-3-nitrophe-
nyl)sulfonyl)-4-(4-((4'-chloro-5,5-dimethyl-3,4,5,6-tetra-
hydro-[1,1'-biphenyl]-2-yl)methyl)piperazin-1-yl)-2-(2,
3-dihydropyrrolo[3',2':5,6]pyrido[2,3-b][1,4]oxazin-1
(6H)-yl)benzamide,
(R)-4-(4-((4'-chloro-5,5-dimethyl-3,4,5,6-tetrahydro-[1,1'-
biphenyl]-2-yl)methyl)piperazin-1-yl)-2-(2,3-dihydropyr-
rolo[3',2':5,6]pyrido[2,3-b][1,4]oxazin-1(6H)-yl)-N-((4-
(((2-fluoro-1,4-dioxan-2-yl)methyl)amino)-3-
nitrophenyl)sulfonyl)benzamide,
(S)—N-((4-(((1,4-dioxan-2-yl)methyl)amino)-3-nitrophe-
nyl)sulfonyl)-4-(4-((4'-chloro-5,5-dimethyl-3,4,5,6-tetra-
hydro-[1,1'-biphenyl]-2-yl)methyl)piperazin-1-yl)-2-(3,
3-difluoro-2,3-dihydropyrrolo[3',2':5,6]pyrido[2,3-b][1,
4]oxazin-1(6H)-yl)benzamide,
(R)-4-(4-((4'-chloro-5,5-dimethyl-3,4,5,6-tetrahydro-[1,1'-
biphenyl]-2-yl)methyl)piperazin-1-yl)-2-(3,3-difluoro-2,
3-dihydropyrrolo[3',2':5,6]pyrido[2,3-b][1,4]oxazin-1
(6H)-yl)-N-((4-4(2-fluoro-1,4-dioxan-2-yl)methyl)
amino)-3-nitrophenyl)sulfonyl)benzamide,
4-(4-((4'-chloro-5,5-dimethyl-3,4,5,6-tetrahydro-[1,1'-bi-
phenyl]-2-yl)methyl)piperazin-1-yl)-2-(3,3-difluoro-2,3-
dihydropyrrolo[3',2':5,6]pyrido[2,3-b][1,4]oxazin-1(6H)-
yl)-N-((4-(((4-fluorotetrahydro-2H-pyran-4-yl)methyl)
amino)-3-nitrophenyl)sulfonyl)benzamide,
4-(4-((4'-chloro-5,5-dimethyl-3,4,5,6-tetrahydro-[1,1'-bi-
phenyl]-2-yl)methyl)piperazin-1-yl)-2-(2,3-dihydropyr-
rolo[3',2':5,6]pyrido[2,3-b][1,4]oxazin-1(6H)-yl)-N-((4-
(((4-((dimethyl(oxo)-l6-sulfaneylidene)amino)
cyclohexyl)methyl)amino)-3-nitrophenyl)sulfonyl)
benzamide,
4-(4-((4'-chloro-5,5-dimethyl-3,4,5,6-tetrahydro-[1,1'-bi-
phenyl]-2-yl)methyl)piperazin-1-yl)-2-(2,3-dihydropyr-
rolo[3',2':5,6]pyrido[2,3-b][1,4]oxazin-1(6H)-yl)-N-((4-
((2-(4-((dimethyl(oxo)-l6-sulfaneylidene)amino)
piperidin-1-yl)ethyl)amino)-3-nitrophenyl)sulfonyl)
benzamide,
4-(4-((4'-chloro-5,5-dimethyl-3,4,5,6-tetrahydro-[1,1'-bi-
phenyl]-2-yl)methyl)piperazin-1-yl)-2-(2,3-dihydropyr-
rolo[3',2':5,6]pyrido[2,3-b][1,4]oxazin-1(6H)-yl)-N-((3-
nitro-4-(((4-((1-oxidotetrahydro-1l6-thiophen-1-ylidene)
amino)cyclohexyl)methyl)amino)phenyl)sulfonyl)
benzamide, or
(S)-4-(4-((4'-chloro-5,5-dimethyl-3,4,5,6-tetrahydro-[1,1'-
biphenyl]-2-yl)methyl)piperazin-1-yl)-2-(2,3-dihydropy-
rrolo[3',2':5,6]pyrido[2,3-b][1,4]oxazin-1(6H)-yl)-N-((4-
((1-(4-((dimethyl(oxo)-l6-sulfaneylidene)amino)
piperidin-1-yl)propan-2-yl)amino)-3-nitrophenyl)
sulfonyl)benzamide.

Compounds of the invention may contain one or more asymmetric carbon atoms. Accordingly, the compounds may exist as diastereomers, enantiomers or mixtures thereof. The syntheses of the compounds may employ racemates, diastereomers or enantiomers as starting materials or as intermediates. Diastereomeric compounds may be separated by chromatographic or crystallization methods. Similarly, enantiomeric mixtures may be separated using the same techniques or others known in the art. Each of the asymmetric carbon atoms may be in the R or S configuration, and both of these configurations are within the scope of the invention.

Compounds having one or more chiral centers can exist in various stereoisomeric forms. Stereoisomers are compounds that differ only in their spatial arrangement. Stereoisomers include all diastereomeric, enantiomeric, and epimeric forms as well as racemates and mixtures thereof.

The term "geometric isomer" refers to cyclic compounds having at least two substituents, wherein the two substituents are both on the same side of the ring (cis) or wherein the substituents are each on opposite sides of the ring (trans). When a disclosed compound is named or depicted by structure without indicating stereochemistry, it is understood that the name or the structure encompasses one or more of the possible stereoisomers, or geometric isomers, or a mixture of the encompassed stereoisomers or geometric isomers.

When a geometric isomer is depicted by name or structure, it is to be understood that the named or depicted isomer exists to a greater degree than another isomer, that is that the geometric isomeric purity of the named or depicted geometric isomer is greater than 50%, such as at least 60%, 70%, 80%, 90%, 99%, or 99.9% pure by weight. Geometric isomeric purity is determined by dividing the weight of the named or depicted geometric isomer in the mixture by the total weight of all of the geomeric isomers in the mixture.

Racemic mixture means 50% of one enantiomer and 50% of is corresponding enantiomer. When a compound with one chiral center is named or depicted without indicating the stereochemistry of the chiral center, it is understood that the name or structure encompasses both possible enantiomeric forms (e.g., both enantiomerically-pure, enantiomerically-enriched or racemic) of the compound. When a compound with two or more chiral centers is named or depicted without indicating the stereochemistry of the chiral centers, it is understood that the name or structure encompasses all possible diasteriomeric forms (e.g., diastereomerically pure, diastereomerically enriched and equimolar mixtures of one or more diastereomers (e.g., racemic mixtures) of the compound.

Enantiomeric and diastereomeric mixtures can be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and diastereomers also can be obtained from diastereomerically- or enantiomerically-pure intermediates, reagents, and catalysts by well-known asymmetric synthetic methods.

When a compound is designated by a name or structure that indicates a single enantiomer, unless indicated otherwise, the compound is at least 60%, 70%, 80%, 90%, 99% or 99.9% optically pure (also referred to as "enantiomerically pure"). Optical purity is the weight in the mixture of the named or depicted enantiomer divided by the total weight in the mixture of both enantiomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers is included. It is to be further understood that the stereoisomeric purity of the named or depicted stereoisomers at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

A modified compound of any one of such compounds including a modification having an improved (e.g., enhanced, greater) pharmaceutical solubility, stability, bioavailability and/or therapeutic index as compared to the unmodified compound is also contemplated. The examples of modifications include but not limited to the prodrug derivatives, and the deuterium-enriched compounds. For example:

Prodrug derivatives: prodrugs, upon administration to a subject, will converted in vivo into active compounds of the present invention [*Nature Reviews of Drug Discovery*, 2008, Volume 7, p 255]. It is noted that in many instances, the prodrugs themselves also fall within the scope of the range of compounds according to the present invention. The prodrugs of the compounds of the present invention can be prepared by starndard organic reaction, for example, by reacting with a carbamylating agent (e.g., 1,1-acyloxyalkylcarbonochloridate, para-nitrophenyl carbonate, or the like) or an acylating agent. Further examples of methods and strategies of making prodrugs are described in *Bioorganic and Medicinal Chemistry Letters,* 1994, Vol. 4, p. 1985.

Deuterium-enriched compounds: deuterium (D or $^2$H) is a stable, non-radioactive isotope of hydrogen and has an atomic weight of 2.0144. Hydrogen naturally occurs as a mixture of the isotopes $^1$H (hydrogen or protium), D ($^2$H or deuterium), and T ($^3$H or tritium). The natural abundance of deuterium is 0.015%. One of ordinary skill in the art recognizes that in all chemical compounds with a H atom, the H atom actually represents a mixture of H and D, with about 0.015% being D. Thus, compounds with a level of deuterium that has been enriched to be greater than its natural abundance of 0.015%, should be considered unnatural and, as a result, novel over their nonenriched counterparts.

It should be recognized that the compounds of the present invention may be present and optionally administered in the form of salts, and solvates. The invention encompasses any pharmaceutically acceptable salts and solvates of any one of the above-described compounds and modifications thereof. For example, it is within the scope of the present invention to convert the compounds of the present invention into and use them in the form of their pharmaceutically acceptable salts derived from various organic and inorganic acids and bases in accordance with procedures well known in the art.

When the compounds of the present invention possess a free base form, the compounds can be prepared as a pharmaceutically acceptable acid addition salt by reacting the free base form of the compound with a pharmaceutically acceptable inorganic or organic acid, e.g., hydrohalides such as hydrochloride, hydrobromide, hydroiodide; other mineral acids such as sulfate, nitrate, phosphate, etc.; and alkyl and monoarylsulfonates such as ethanesulfonate, toluenesulfonate and benzenesulfonate; and other organic acids and their corresponding salts such as acetate, tartrate, maleate, succinate, citrate, benzoate, salicylate and ascorbate. Further acid addition salts of the present invention include, but are not limited to: adipate, alginate, arginate, aspartate, bisulfate, bisulfite, bromide, butyrate, camphorate, camphorsulfonate, caprylate, chloride, chlorobenzoate, cyclopentanepropionate, digluconate, dihydrogenphosphate, dinitrobenzoate, dodecylsulfate, fumarate, galacterate (from mucic acid), galacturonate, glucoheptaoate, gluconate, glutamate, glycerophosphate, hemisuccinate, hemisulfate, heptanoate, hexanoate, hippurate, 2-hydroxyethanesulfonate, iodide, isethionate, iso-butyrate, lactate, lactobionate, malonate, mandelate, metaphosphate, methanesulfonate, methylbenzoate, monohydrogenphosphate, 2-naphthalenesulfonate, nicotinate, oxalate, oleate, pamoate, pectinate, persulfate, phenylacetate, 3-phenylpropionate, phosphonate and phthalate. It should be recognized that the free base forms will typically differ from their respective salt forms somewhat in physical properties such as solubility in polar solvents, but otherwise the salts are equivalent to their respective free base forms for the purposes of the present invention.

When the compounds of the present invention possess a free acid form, a pharmaceutically acceptable base addition salt can be prepared by reacting the free acid form of the compound with a pharmaceutically acceptable inorganic or organic base. Examples of such bases are alkali metal hydroxides including potassium, sodium and lithium hydroxides; alkaline earth metal hydroxides such as barium and calcium hydroxides; alkali metal alkoxides, e.g., potassium ethanolate and sodium propanolate; and various organic bases such as ammonium hydroxide, piperidine, diethanolamine and N-methylglutamine. Also included are the aluminum salts of the compounds of the present invention. Further base salts of the present invention include, but are not limited to: copper, ferric, ferrous, lithium, magnesium, manganic, manganous, potassium, sodium and zinc salts. Organic base salts include, but are not limited to, salts of primary, secondary and tertiary amines, substituted amines including naturally occurring substituted amines, cyclic amines and basic ion exchange resins, e.g., arginine, betaine, caffeine, chloroprocaine, choline, N,N'-dibenzylethylenediamine (benzathine), dicyclohexylamine, diethanolamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)-methylamine (tromethamine) It should be recognized that the free acid forms will typically differ from their respective salt forms somewhat in physical properties such as solubility in polar solvents, but otherwise the salts are equivalent to their respective free acid forms for the purposes of the present invention.

In one aspect, a pharmaceutically acceptable salt is a hydrochloride salt, hydrobromide salt, methanesulfonate, toluenesulfonate, acetate, fumarate, sulfate, bisulfate, succinate, citrate, phosphate, maleate, nitrate, tartrate, benzoate, biocarbonate, carbonate, sodium hydroxide salt, calcium hydroxide salt, potassium hydroxide salt, tromethamine salt, or mixtures thereof.

Compounds of the present invention that comprise tertiary nitrogen-containing groups may be quaternized with such agents as $(C_{1-4})$ alkyl halides, e.g., methyl, ethyl, iso-propyl and tert-butyl chlorides, bromides and iodides; di-$(C_{1-4})$ alkyl sulfates, e.g., dimethyl, diethyl and diamyl sulfates; alkyl halides, e.g., decyl, dodecyl, lauryl, myristyl and stearyl chlorides, bromides and iodides; and aryl $(C_{1-4})$ alkyl halides, e.g., benzyl chloride and phenethyl bromide. Such salts permit the preparation of both water- and oil-soluble compounds of the invention.

Amine oxides, also known as amine-N-oxide and N-oxide, of anti-cancer agents with tertiary nitrogen atoms have been developed as prodrugs [Mol Cancer Therapy. 2004 March; 3(3):233-44]. Compounds of the present invention that comprise tertiary nitrogen atoms may be oxidized by such agents as hydrogen peroxide ($H_2O_2$), Caro's acid or peracids like meta-Chloroperoxybenzoic acid (mCPBA) to from amine oxide.

The compounds disclosed therein are bcl-2 inhibitors. The pharmaceutical composition of the present invention comprises one or more bcl-2 inhibitors, or a pharmaceutically acceptable salt thereof, and a pharmaceutically acceptable carrier or diluent.

"Pharmaceutically acceptable carrier" and "pharmaceutically acceptable diluent" refer to a substance that aids the formulation and/or administration of an active agent to and/or absorption by a subject and can be included in the compositions of the present disclosure without causing a significant adverse toxicological effect on the subject. Non-limiting examples of pharmaceutically acceptable carriers and/or diluents include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with or interfere with the activity of the compounds provided herein. One of ordinary skill in the art will recognize that other pharmaceutical excipients are suitable for use with disclosed compounds.

The pharmaceutical compositions of the present invention optionally include one or more pharmaceutically acceptable carriers and/or diluents therefor, such as lactose, starch, cellulose and dextrose. Other excipients, such as flavoring agents; sweeteners; and preservatives, such as methyl, ethyl, propyl and butyl parabens, can also be included. More complete listings of suitable excipients can be found in the Handbook of Pharmaceutical Excipients ($5^{th}$ Ed., Pharmaceutical Press (2005)). A person skilled in the art would know how to prepare formulations suitable for various types of administration routes. Conventional procedures and ingredients for the selection and preparation of suitable formulations are described, for example, in Remington's Pharmaceutical Sciences (2003-20th edition) and in The United States Pharmacopeia: The National Formulary (USP 24 NF19) published in 1999. The carriers, diluents and/or excipients are "acceptable" in the sense of being compatible with the other ingredients of the pharmaceutical composition and not deleterious to the recipient thereof.

The pharmaceutical compositions of the present invention may further comprise other conventional pharmaceutically inactive agents. Any inert excipient that is commonly used as a carrier or diluent may be used in compositions of the present invention, such as sugars, polyalcohols, soluble polymers, salts and lipids. Sugars and polyalcohols which may be employed include, without limitation, lactose, sucrose, mannitol, and sorbitol. Illustrative of the soluble polymers which may be employed are polyoxyethylene, poloxamers, polyvinylpyrrolidone, and dextran. Useful salts include, without limitation, sodium chloride, magnesium chloride, and calcium chloride. Lipids which may be employed include, without limitation, fatty acids, glycerol fatty acid esters, glycolipids, and phospholipids.

In addition, the pharmaceutical compositions of the present invention may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCL, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol, cyclodextrins), a glidant (e.g., colloidal silicon dioxide), anti-oxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate, methyl cellulose, hydroxyethyl cellulose, carboxymethylcellulose sodium), polymer coatings (e.g., poloxamers or poloxamines), coating and film forming agents (e.g., ethyl cellulose, acrylates, polymethacrylates) and/or adjuvants.

In one embodiment, the pharmaceutical compositions are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Additionally, the invention encompasses pharmaceutical compositions comprising any solid or liquid physical form of the compound of the invention. For example, the compounds can be in a crystalline form, in amorphous form, and have any particle size. The particles may be micronized, or may be agglomerated, particulate granules, powders, oils, oily suspensions or any other form of solid or liquid physical form.

When compounds according to the present invention exhibit insufficient solubility, methods for solubilizing the compounds may be used. Such methods are known to those of skill in this art, and include, but are not limited to, pH adjustment and salt formation, using co-solvents, such as ethanol, propylene glycol, polyethylene glycol (PEG) 300, PEG 400, DMA (10-30%), DMSO (10-20%), NMP (10-20%), using surfactants, such as polysorbate 80, polysorbate 20 (1-10%), cremophor EL, Cremophor RH40, Cremophor RH60 (5-10%), Pluronic F68/Poloxamer 188 (20-50%), Solutol HS15 (20-50%), Vitamin E TPGS, and d-α-tocopheryl PEG 1000 succinate (20-50%), using complexation such as HPβCD and SBEβCD (10-40%), and using advanced approaches such as micelle, addition of a polymer, nanoparticle suspensions, and liposome formation.

A wide variety of administration methods may be used in conjunction with the compounds of the present invention. Compounds of the present invention may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds according to the invention may also be administered or coadministered in slow release dosage forms. Compounds may be in gaseous, liquid, semi-liquid or solid form, formulated in a manner suitable for the route of administration to be used. For oral administration, suitable solid oral formulations include tablets, capsules, pills, granules, pellets, sachets and effervescent, powders, and the like. Suitable liquid oral formulations include solutions, suspensions, dispersions, emulsions, oils and the like. For parenteral administration, reconstitution of a lyophilized powder is typically used.

As used herein, "acyl" means a carbonyl containing substituent represented by the formula —C(O)—R in which R is H, alkyl, a carbocycle, a heterocycle, carbocycle-substituted alkyl or heterocycle-substituted alkyl wherein the alkyl, alkoxy, carbocycle and heterocycle are as defined herein. Acyl groups include alkanoyl (e.g. acetyl), aroyl (e.g. benzoyl), and heteroaroyl.

"Aliphatic" means a moiety characterized by a straight or branched chain arrangement of constituent carbon atoms and may be saturated or partially unsaturated with one or more double or triple bonds.

The term "alkyl" refers to a straight or branched hydrocarbon containing 1-20 carbon atoms (e.g., $C_1$-$C_{10}$, $C_1$-$C_6$). Examples of alkyl include, but are not limited to, methyl, methylene, ethyl, ethylene, n-propyl, i-propyl, n-butyl, i-butyl, and t-butyl. Preferably, the alkyl group has one to ten carbon atoms. More preferably, the alkyl group has one to four carbon atoms.

The term "alkenyl" refers to a straight or branched hydrocarbon containing 2-20 carbon atoms (e.g., $C_2$-$C_{10}$, $C_2$-$C_6$) and one or more double bonds. Examples of alkenyl include, but are not limited to, ethenyl, propenyl, and allyl. Preferably, the alkylene group has two to ten carbon atoms. More preferably, the alkylene group has two to four carbon atoms.

The term "alkynyl" refers to a straight or branched hydrocarbon containing 2-20 carbon atoms (e.g., $C_2$-$C_{10}$, $C_2$-$C_6$) and one or more triple bonds. Examples of alkynyl include, but are not limited to, ethynyl, 1-propynyl, 1- and 2-butynyl, and 1-methyl-2-butynyl. Preferably, the alkynyl group has two to ten carbon atoms. More preferably, the alkynyl group has two to four carbon atoms.

The term "alkylamino" refers to an —N(R)-alkyl in which R can be H, alkyl, alkenyl, alkynyl, cycloalkyl, cycloalkenyl, heterocycloalkyl, heterocycloalkenyl, aryl, or heteroaryl.

"Alkoxy" means an oxygen moiety having a further alkyl substituent.

"Alkoxycarbonyl" means an alkoxy group attached to a carbonyl group.

"Oxoalkyl" means an alkyl, further substituted with a carbonyl group. The carbonyl group may be an aldehyde, ketone, ester, amide, acid or acid chloride.

The term "cycloalkyl" refers to a saturated hydrocarbon ring system having 3 to 30 carbon atoms (e.g., $C_3$-$C_{12}$, $C_3$-$C_8$, $C_3$-$C_6$). Examples of cycloalkyl include, but are not limited to, cyclopropyl, cyclobutyl, cyclopentyl, cyclohexyl, cycloheptyl, and cyclooctyl. The term "cycloalkenyl" refers to a non-aromatic hydrocarbon ring system having 3 to 30 carbons (e.g., $C_3$-$C_{12}$) and one or more double bonds. Examples include cyclopentenyl, cyclohexenyl, and cycloheptenyl.

The term "heterocycloalkyl" refers to a saturated or unsaturated nonaromatic 5-8 membered monocyclic, 8-12 membered bicyclic, or 11-14 membered tricyclic ring system having 1 to 4 heteroatoms (such as O, N, S, B, P, Si, or Se), which may be the same or different. Examples of heterocycloalkyl groups include, but are not limited to, piperazinyl, pyrrolidinyl, dioxanyl, morpholinyl, and tetrahydrofuranyl.

The term "heterocycloalkenyl" refers to a nonaromatic 5-8 membered monocyclic, 8-12 membered bicyclic, or 11-14 membered tricyclic ring system having one or more heteroatoms (such as O, N, S, P, B, Si, or Se) and one or more double bonds.

The term "aryl" refers to a 6-carbon monocyclic, 10-carbon bicyclic, 14-carbon tricyclic aromatic ring system. Examples of aryl groups include, but are not limited to, phenyl, naphthyl, and anthracenyl.

The term "heteroaryl" refers to an aromatic 5-8 membered monocyclic, 8-12 membered bicyclic, or 11-14 membered tricyclic ring system having one or more heteroatoms (such as O, N, S, P, or Se). Examples of heteroaryl groups include pyridyl, furyl, imidazolyl, benzimidazolyl, pyrimidinyl, thienyl, quinolinyl, indolyl, and thiazolyl.

Alkyl, alkenyl, alkynyl, cycloalkyl, heterocycloalkyl, cycloalkenyl, heterocycloalkenyl, alkylamino, aryl, and heteroaryl mentioned above include both substituted and unsubstituted moieties. Possible substituents on alkylamino, cycloalkyl, heterocycloalkyl, cycloalkenyl, heterocycloalkenyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, arylamino, hydroxy, halo, oxo (O=), thioxo (S=), thio, silyl, $C_1$-$C_{10}$ alkylthio, arylthio, $C_1$-$C_{10}$ alkylsulfonyl, arylsulfonyl, acylamino, aminoacyl, aminothioacyl, amidino, mercapto, amido, thioureido, thiocyanato, sulfonamido, guanidine, ureido, cyano, nitro, acyl, thioacyl, acyloxy, carbamido, carbamyl, carboxyl, and carboxylic ester. On the other hand, possible substituents on alkyl, alkenyl, or alkynyl include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

"Amino" means a nitrogen moiety having two further substituents where each substituent has a hydrogen or carbon atom alpha bonded to the nitrogen. Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Aromatic" means a moiety wherein the constituent atoms make up an unsaturated ring system, all atoms in the ring system are sp2 hybridized and the total number of pi electrons is equal to 4n+2. An aromatic ring may be such that the ring atoms are only carbon atoms or may include carbon and non-carbon atoms (see Heteroaryl).

"Carbamoyl" means the radical —OC(O)NR$_a$R$_b$ where R$_a$ and R$_b$ are each independently two further substituents where a hydrogen or carbon atom is alpha to the nitrogen. It is noted that carbamoyl moieties may include protected derivatives thereof. Examples of suitable protecting groups for carbamoyl moieties include acetyl, tert-butoxycarbonyl, benzyloxycarbonyl, and the like. It is noted that both the unprotected and protected derivatives fall within the scope of the invention.

"Carbonyl" means the radical —C(O)—. It is noted that the carbonyl radical may be further substituted with a variety of substituents to form different carbonyl groups including acids, acid halides, amides, esters, and ketones.

"Carboxy" means the radical —C(O)O—. It is noted that compounds of the invention containing carboxy moieties may include protected derivatives thereof, i.e., where the oxygen is substituted with a protecting group. Suitable protecting groups for carboxy moieties include benzyl, tert-butyl, and the like.

"Cyano" means the radical —CN.

"Formyl" means the radical —CH=O.

"Formimino" means the radical —HC=NH.

"Halo" means fluoro, chloro, bromo or iodo.

"Halo-substituted alkyl", as an isolated group or part of a larger group, means "alkyl" substituted by one or more "halo" atoms, as such terms are defined in this Application. Halo-substituted alkyl includes haloalkyl, dihaloalkyl, trihaloalkyl, perhaloalkyl and the like.

"Hydroxy" means the radical —OH.

"Imine derivative" means a derivative comprising the moiety —C(=NR)—, wherein R comprises a hydrogen or carbon atom alpha to the nitrogen.

"Isomers" mean any compound having identical molecular formulae but differing in the nature or sequence of bonding of their atoms or in the arrangement of their atoms in space. Isomers that differ in the arrangement of their atoms in space are termed "stereoisomers." Stereoisomers that are not mirror images of one another are termed "diastereomers" and stereoisomers that are nonsuperimposable mirror images are termed "enantiomers" or sometimes "optical isomers." A carbon atom bonded to four nonidentical substituents is termed a "chiral center." A compound with one chiral center has two enantiomeric forms of opposite chirality. A mixture of the two enantiomeric forms is termed a "racemic mixture."

"Nitro" means the radical —NO$_2$.

"Protected derivatives" means derivatives of compounds in which a reactive site are blocked with protecting groups. Protected derivatives are useful in the preparation of pharmaceuticals or in themselves may be active as inhibitors. A comprehensive list of suitable protecting groups can be found in T. W. Greene, Protecting Groups in Organic Synthesis, 3rd edition, Wiley & Sons, 1999.

The term "substituted" means that an atom or group of atoms has replaced hydrogen as the substituent attached to another group. For aryl and heteroaryl groups, the term "substituted" refers to any level of substitution, namely mono-, di-, tri-, tetra-, or penta-substitution, where such substitution is permitted. The substituents are independently selected, and substitution may be at any chemically accessible position. The term "unsubstituted" means that a given moiety may consist of only hydrogen substituents through available valencies (unsubstituted).

If a functional group is described as being "optionally substituted," the function group may be either (1) not substituted, or (2) substituted. If a carbon of a functional group is described as being optionally substituted with one or more of a list of substituents, one or more of the hydrogen atoms on the carbon (to the extent there are any) may separately and/or together be replaced with an independently selected optional substituent.

"Sulfide" means —S—R wherein R is H, alkyl, carbocycle, heterocycle, carbocycloalkyl or heterocycloalkyl. Particular sulfide groups are mercapto, alkylsulfide, for example methylsulfide (—S-Me); arylsulfide, e.g., phenylsulfide; aralkylsulfide, e.g., benzylsulfide.

"Sulfinyl" means the radical —S(O)—. It is noted that the sulfinyl radical may be further substituted with a variety of substituents to form different sulfinyl groups including sulfinic acids, sulfinamides, sulfinyl esters, and sulfoxides.

"Sulfonyl" means the radical —S(O)(O)—. It is noted that the sulfonyl radical may be further substituted with a variety of substituents to form different sulfonyl groups including sulfonic acids, sulfonamides, sulfonate esters, and sulfones.

"Thiocarbonyl" means the radical —C(S)—. It is noted that the thiocarbonyl radical may be further substituted with a variety of substituents to form different thiocarbonyl groups including thioacids, thioamides, thioesters, and thioketones.

"Animal" includes humans, non-human mammals (e.g., non-human primates, rodents, mice, rats, hamsters, dogs, cats, rabbits, cattle, horses, sheep, goats, swine, deer, and the like) and non-mammals (e.g., birds, and the like).

"Bioavailability" as used herein is the fraction or percentage of an administered dose of a drug or pharmaceutical composition that reaches the systemic circulation intact. In general, when a medication is administered intravenously, its bioavailability is 100%. However, when a medication is administered via other routes (e.g., orally), its bioavailability decreases (e.g., due to incomplete absorption and first-pass metabolism). Methods to improve the bioavailability include prodrug approach, salt synthesis, particle size reduction, complexation, change in physical form, solid dispersions, spray drying, and hot-melt extrusion.

"Disease" specifically includes any unhealthy condition of an animal or part thereof and includes an unhealthy condition that may be caused by, or incident to, medical or veterinary therapy applied to that animal, i.e., the "side effects" of such therapy.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means organic or inorganic salts of compounds of the present invention which are pharmaceutically acceptable, as defined above, and which possess the desired pharmacological activity. Such salts include acid addition salts formed with inorganic acids, or with organic acids. Pharmaceutically acceptable salts also include base addition salts which may be formed when acidic protons present are capable of reacting with inorganic or organic bases. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate," ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

"Pharmacophore," as defined by The International Union of Pure and Applied Chemistry, is an ensemble of steric and electronic features that is necessary to ensure the optimal supramolecular interactions with a specific biological target and to trigger (or block) its biological response. For example, Camptothecin is the pharmacophore of the well known drug topotecan and irinotecan. Mechlorethamine is the pharmacophore of a list of widely used nitrogen mustard drugs like Melphalan, Cyclophosphamide, Bendamustine, and so on.

"Prodrug" means a compound that is convertible in vivo metabolically into an active pharmaceutical according to the present invention. For example, an inhibitor comprising a hydroxyl group may be administered as an ester that is converted by hydrolysis in vivo to the hydroxyl compound.

"Stability" in general refers to the length of time a drug retains its properties without loss of potency. Sometimes this is referred to as shelf life. Factors affecting drug stability include, among other things, the chemical structure of the drug, impurity in the formulation, pH, moisture content, as well as environmental factors such as temperature, oxidization, light, and relative humidity. Stability can be improved by providing suitable chemical and/or crystal modifications (e.g., surface modifications that can change hydration kinetics; different crystals that can have different properties), excipients (e.g., anything other than the active substance in the dosage form), packaging conditions, storage conditions, etc.

"Therapeutically effective amount" of a composition described herein is meant an amount of the composition which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the composition described above may range from about 0.1 mg/kg to about 500 mg/kg, preferably from about 0.2 to about 50 mg/kg. Effective doses will also vary depending on route of administration, as well as the possibility of co-usage with other agents. It will be understood, however, that the total daily usage of the compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

As used herein, the term "treating" refers to administering a compound to a subject that has a neoplastic or immune disorder, or has a symptom of or a predisposition toward it, with the purpose to cure, heal, alleviate, relieve, alter, remedy, ameliorate, improve, or affect the disorder, the symptoms of or the predisposition toward the disorder.

The term "an effective amount" refers to the amount of the active agent that is required to confer the intended therapeutic effect in the subject. Effective amounts may vary, as recognized by those skilled in the art, depending on route of administration, excipient usage, and the possibility of co-usage with other agents.

A "subject" refers to a human and a non-human animal. Examples of a non-human animal include all vertebrates, e.g., mammals, such as non-human primates (particularly higher primates), non-human mammal, dog, rodent (e.g., mouse or rat), guinea pig, cat, and non-mammals, such as birds, amphibians, reptiles, etc. In a preferred embodiment, the subject is a human. In another embodiment, the subject is an experimental animal or animal suitable as a disease model.

"Combination therapy" includes the administration of the subject compounds of the present invention in further combination with other biologically active ingredients (such as, but not limited to, a second and different antineoplastic agent) and non-drug therapies (such as, but not limited to, surgery or radiation treatment). For instance, the compounds of the invention can be used in combination with other pharmaceutically active compounds, or non-drug therapies, preferably compounds that are able to enhance the effect of the compounds of the invention. The compounds of the invention can be administered simultaneously (as a single preparation or separate preparation) or sequentially to the other therapies. In general, a combination therapy envisions administration of two or more drugs/treatments during a single cycle or course of therapy.

In one embodiment, the compounds of the invention are administered in combination with one or more of traditional chemotherapeutic agents. The traditional chemotherapeutic agents encompass a wide range of therapeutic treatments in the field of oncology. These agents are administered at various stages of the disease for the purposes of shrinking tumors, destroying remaining cancer cells left over after surgery, inducing remission, maintaining remission and/or alleviating symptoms relating to the cancer or its treatment. Examples of such agents include, but are not limited to, alkylating agents such as Nitrogen Mustards (e.g., Bendamustine, Cyclophosphamide, Melphalan, Chlorambucil, Isofosfamide), Nitrosureas (e.g., Carmustine, Lomustine and Streptozocin), ethylenimines (e.g., thiotepa, hexamethylmelanine), Alkylsulfonates (e.g., Busulfan), Hydrazines and Triazines (e.g., Altretamine, Procarbazine, Dacarbazine and Temozolomide), and platinum based agents (e.g., Carboplatin, Cisplatin, and Oxaliplatin); plant alkaloids such as Podophyllotoxins (e.g., Etoposide and Tenisopide), Taxanes (e.g., Paclitaxel and Docetaxel), Vinca alkaloids (e.g., Vincristine, Vinblastine and Vinorelbine); anti-tumor antibiotics such as Chromomycins (e.g., Dactinomycin and Plicamycin), Anthracyclines (e.g., Doxorubicin, Daunorubicin, Epirubicin, Mitoxantrone, and Idarubicin), and miscellaneous antibiotics such as Mitomycin and Bleomycin; anti-metabolites such as folic acid antagonists (e.g., Methotrexate), pyrimidine antagonists (e.g., 5-Fluorouracil, Foxuridine, Cytarabine, Capecitabine, and Gemcitabine), purine antagonists (e.g., 6-Mercaptopurine and 6-Thioguanine) and adenosine deaminase inhibitors (e.g., Cladribine, Fludarabine, Nelarabine and Pentostatin); topoisomerase inhibitors such as topoisomerase I inhibitors (Topotecan, Irinotecan), topoisomerase II inhibitors (e.g., Amsacrine, Etoposide, Etoposide phosphate, Teniposide), and miscellaneous antineoplastics such as ribonucleotide reductase inhibitors (Hydroxyurea), adrenocortical steroid inhibitor (Mitotane), anti-microtubule agents (Estramustine), and retinoids (Bexarotene, Isotretinoin, Tretinoin (ATRA).

In one aspect of the invention, the compounds may be administered in combination with one or more targeted anti-cancer agents that modulate protein kinases involved in various disease states. Examples of such kinases may include, but are not limited ABL1, ABL2/ARG, ACK1, AKT1, AKT2, AKT3, ALK, ALK1/ACVRL1, ALK2/ACVR1, ALK4/ACVR1B, ALK5/TGFBR1, ALK6/BMPR1B, AMPK(A1/B1/G1), AMPK(A1/B1/G2), AMPK(A1/B1/G3), AMPK(A1/B2/G1), AMPK(A2/B1/G1), AMPK(A2/B2/G1), AMPK(A2/B2/G2), ARAF, ARK5/NUAK1, ASK1/MAP3K5, ATM, Aurora A, Aurora B, Aurora C, AXL, BLK, BMPR2, BMX/ETK, BRAF, BRK, BRSK1, BRSK2, BTK, CAMK1a, CAMK1b, CAMK1d, CAMK1g, CAMKIIa, CAMKIIb, CAMKIId, CAMKIIg, CAMK4, CAMKK1, CAMKK2, CDC7-DBF4, CDK1-cyclin A, CDK1-cyclin B, CDK1-cyclin E, CDK2-cyclin A, CDK2-cyclin A1, CDK2-cyclin E, CDK3-cyclin E, CDK4-cyclin D1, CDK4-cyclin D3, CDK5-p25, CDK5-p35, CDK6-cyclin D1, CDK6-cyclin D3, CDK7-cyclin H, CDK9-cyclin K, CDK9-cyclin T1, CHK1, CHK2, CK1a1, CK1d, CK1epsilon, CK1g1, CK1g2, CK1g3, CK2a, CK2a2, c-KIT, CLK1, CLK2, CLK3, CLK4, c-MER, c-MET, COT1/MAP3K8, CSK, c-SRC, CSF1R, CTK/MATK, DAPK1, DAPK2, DCAMKL1, DCAMKL2, DDR1, DDR2, DLK/MAP3K12, DMPK, DMPK2/CDC42BPG, DNA-PK, DRAK1/STK17A, DYRK1/DYRK1A, DYRK1B, DYRK2, DYRK3, DYRK4, EEF2K, EGFR, EIF2AK1, EIF2AK2, EIF2AK3, EIF2AK4/GCN2, EPHA1, EPHA2, EPHA3, EPHA4, EPHA5, EPHA6, EPHA7, EPHA8, EPHB1, EPHB2, EPHB3, EPHB4, ERBB2/HER2, ERBB4/HER4, ERK1/MAPK3, ERK2/MAPK1, ERK5/MAPK7, FAK/PTK2, FER, FES/FPS, FGFR1, FGFR2, FGFR3, FGFR4, FGR, FLT1/VEGFR1, FLT3, FLT4/VEGFR3, FMS, FRK/PTK5, FYN, GCK/MAP4K2, GRK1, GRK2, GRK3, GRK4, GRK5, GRK6, GRK7, GSK3a, GSK3b, Haspin, HCK, HGK/MAP4K4, HIPK1, HIPK2, HIPK3, HIPK4, HPK1/MAP4K1, IGF1R, IKKa/CHUK, IKKb/IKBKB, IKKe/IKBKE, IR, IRAK1, IRAK4, IRR/INSRR, ITK, JAK1, JAK2, JAK3, JNK1, JNK2, JNK3, KDR/VEGFR2, KHS/MAP4K5, LATS1, LATS2, LCK, LCK2/ICK, LKB1, LIMK1, LOK/STK10, LRRK2, LYN, LYNB, MAPKAPK2, MAPKAPK3, MAPKAPK5/PRAK, MARK1, MARK2/PAR-1Ba, MARK3, MARK4, MEK1, MEK2, MEKK1, MEKK2, MEKK3, MELK, MINK/MINK1, MKK4, MKK6, MLCK/MYLK, MLCK2/MYLK2, MLK1/MAP3K9, MLK2/MAP3K10, MLK3/MAP3K11, MNK1, MNK2, MRCKa/, CDC42BPA, MRCKb/, CDC42BPB, MSK1/RPS6KA5, MSK2/RPS6KA4, MSSK1/STK23, MST1/STK4, MST2/STK3, MST3/STK24, MST4, mTOR/FRAP1, MUSK, MYLK3, MYO3b, NEK1, NEK2, NEK3, NEK4, NEK6, NEK7, NEK9, NEK11, NIK/MAP3K14, NLK, OSR1/OXSR1, P38a/MAPK14, P38b/MAPK11, P38d/MAPK13, P38g/MAPK12, P70S6K/RPS6KB1, p70S6Kb/, RPS6KB2, PAK1, PAK2, PAK3, PAK4, PAK5, PAK6, PASK, PBK/TOPK, PDGFRa, PDGFRb, PDK1/PDPK1, PDK1/PDHK1, PDK2/PDHK2, PDK3/PDHK3, PDK4/PDHK4, PHKg1, PHKg2, PI3Ka, (p110a/p85a), PI3Kb, (p110b/p85a), PI3Kd, (p110d/p85a), PI3Kg(p120g), PIM1, PIM2, PIM3, PKA, PKAcb, PKAcg, PKCa, PKCb1, PKCb2, PKCd, PKCepsilon, PKCeta, PKCg, PKCiota, PKCmu/PRKD1, PKCnu/PRKD3, PKCtheta, PKCzeta, PKD2/PRKD2, PKG1a, PKG1b, PKG2/PRKG2, PKN1/PRK1, PKN2/PRK2, PKN3/PRK3, PLK1, PLK2, PLK3, PLK4/SAK, PRKX, PYK2, RAF1, RET, RIPK2, RIPK3, RIPKS, ROCK1, ROCK2, RON/MST1R, ROS/ROS1, RSK1, RSK2, RSK3, RSK4, SGK1, SGK2, SGK3/SGKL, SIK1, SIK2, SLK/STK2, SNARK/NUAK2, SRMS, SSTK/

TSSK6, STK16, STK22D/TSSK1, STK25/YSK1, STK32b/YANK2, STK32c/YANK3, STK33, STK38/NDR1, STK38L/NDR2, STK39/STLK3, SRPK1, SRPK2, SYK, TAK1, TAOK1, TAOK2/TAO1, TAOK3/JIK, TBK1, TEC, TESK1, TGFBR2, TIE2/TEK, TLK1, TLK2, TNIK, TNK1, TRKA, TRKB, TRKC, TRPM7/CHAK1, TSSK2, TSSK3/STK22C, TTBK1, TTBK2, TTK, TXK, TYK1/LTK, TYK2, TYRO3/SKY, ULK1, ULK2, ULK3, VRK1, VRK2, WEE1, WNK1, WNK2, WNK3, YES/YES1, ZAK/MLTK, ZAP70, ZIPK/DAPK3, KINASE, MUTANTS, ABL1(E255K), ABL1(F317I), ABL1(G250E), ABL1(H396P), ABL1 (M351T), ABL1(Q252H), ABL1(T315I), ABL1(Y253F), ALK (C1156Y), ALK(L1196M), ALK (F1174L), ALK (R1275Q), BRAF(V599E), BTK(E41K), CHK2(I157T), c-Kit(A829P), c-KIT(D816H), c-KIT(D816V), c-Kit (D820E), c-Kit(N822K), C-Kit (T670I), c-Kit(V559D), c-Kit(V559D/V654A), c-Kit(V559D/T670I), C-Kit (V560G), c-KIT(V654A), C-MET(D1228H), C-MET (D1228N), C-MET(F1200I), c-MET(M1250T), C-MET (Y1230A), C-MET(Y1230C), C-MET(Y1230D), C-MET (Y1230H), c-Src(T341M), EGFR(G719C), EGFR(G719S), EGFR(L858R), EGFR(L861Q), EGFR(T790M), EGFR, (L858R,T790M), EGFR(d746-750/T790M), EGFR(d746-750), EGFR(d747-749/A750P), EGFR(d747-752/P753S), EGFR(d752-759), FGFR1(V561M), FGFR2(N549H), FGFR3(G697C), FGFR3(K650E), FGPR3(K650M), FGFR4(N535K), FGPR4(V550E), FGFR4(V550L), FLT3 (D835Y), FLT3(ITD), JAK2 (V617F), LRRK2 (G2019S), LRRK2 (I2020T), LRRK2 (R1441C), p38a(T106M), PDG-FRa(D842V), PDGFRa(T674I), PDGFRa(V561D), RET (E762Q), RET(G691S), RET(M918T), RET(R749T), RET (R813Q), RET(V804L), RET(V804M), RET(Y791F), TIF2 (R849W), TIF2(Y897S), and TIF2(Y1108F).

In another aspect of the invention, the subject compounds may be administered in combination with one or more targeted anti-cancer agents that modulate non-kinase biological targets, pathway, or processes. Such targets pathways, or processes include but not limited to heat shock proteins (e.g. HSP90), poly-ADP (adenosine diphosphate)-ribose polymerase (PARP), hypoxia-inducible factors(HIF), proteasome, Wnt/Hedgehog/Notch signaling proteins, TNF-alpha, matrix metalloproteinase, farnesyl transferase, apoptosis pathway (e.g. Bcl-xL, Bcl-2, Bcl-w), histone deacetylases (HDAC), histone acetyltransferases (HAT), and methyltransferase (e.g. histone lysine methyltransferases, histone arginine methyltransferase, DNA methyltransferase, etc), and other immunotherapies(e.g. anti-PD1, anti-PDL1, anti-CTLA4, CAR-T, IDO, A2A antagonist etc).

In another aspect of the invention, the compounds of the invention are administered in combination with one or more of other anti-cancer agents that include, but are not limited to, gene therapy, RNAi cancer therapy, chemoprotective agents (e.g., amfostine, mesna, and dexrazoxane), antibody conjugate(e.g. brentuximab vedotin, ibritumomab tioxetan), cancer immunotherapy such as Interleukin-2, cancer vaccines(e.g., sipuleucel-T) or monoclonal antibodies (e.g., Bevacizumab, Alemtuzumab, Rituximab, Trastuzumab, etc).

In another aspect of the invention, the subject compounds are administered in combination with radiation therapy or surgeries. Radiation is commonly delivered internally (implantation of radioactive material near cancer site) or externally from a machine that employs photon (x-ray or gamma-ray) or particle radiation. Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

In certain embodiments, the compounds of the invention are administered in combination with one or more of radiation therapy, surgery, or anti-cancer agents that include, but are not limited to, DNA damaging agents, anti-metabolites, topoisomerase inhibitors, anti-microtubule agents, kinase inhibitors, epigenetic agents, HSP90 inhibitors, PARP inhibitors, and antibodies targeting VEGF, HER2, EGFR, CD50, CD20, CD30, CD33, etc.

In certain embodiments, the compounds of the invention are administered in combination with one or more of abarelix, abiraterone acetate, aldesleukin, alemtuzumab, altretamine, anastrozole, asparaginase, bendamustine, bevacizumab, bexarotene, bicalutamide, bleomycin, bortezombi, brentuximab vedotin, busulfan, capecitabine, carboplatin, carmustine, cetuximab, chlorambucil, cisplatin, cladribine, clofarabine, clomifene, crizotinib, cyclophosphamide, dasatinib, daunorubicin liposomal, decitabine, degarelix, denileukin diftitox, denileukin diftitox, denosumab, docetaxel, doxorubicin, doxorubicin liposomal, epirubicin, eribulin mesylate, erlotinib, estramustine, etoposide phosphate, everolimus, exemestane, fludarabine, fluorouracil, fotemustine, fulvestrant, gefitinib, gemcitabine, gemtuzumab ozogamicin, goserelin acetate, histrelin acetate, hydroxyurea, ibritumomab tiuxetan, idarubicin, ifosfamide, imatinib mesylate, interferon alfa 2a, ipilimumab, ixabepilone, lapatinib ditosylate, lenalidomide, letrozole, leucovorin, leuprolide acetate, levamisole, lomustine, mechlorethamine, melphalan, methotrexate, mitomycin C, mitoxantrone, nelarabine, nilotinib, oxaliplatin, paclitaxel, paclitaxel protein-bound particle, pamidronate, panitumumab, pegaspargase, peginterferon alfa-2b, pemetrexed disodium, pentostatin, raloxifene, rituximab, sorafenib, streptozocin, sunitinib maleate, tamoxifen, temsirolimus, teniposide, thalidomide, toremifene, tositumomab, trastuzumab, tretinoin, uramustine, vandetanib, vemurafenib, vinorelbine, zoledronate, pembrolizumab, nivolumab, atezolizumab, durvalumab, avelumab, as tisagenlecleucel, axicabtagene ciloleucel, radiation therapy, or surgery.

The invention further provides methods for the prevention or treatment of a neoplastic disease or autoimmune disease. In one embodiment, the invention relates to a method of treating a neoplastic disease or autoimmune disease, in a subject in need of treatment comprising administering to said subject a therapeutically effective amount of a compound of the invention. In one embodiment, the invention further provides for the use of a compound of the invention in the manufacture of a medicament for halting or decreasing a neoplastic disease or autoimmune disease.

In certain embodiments, the neoplastic disease is a lung cancer, head and neck cancer, central nervous system cancer, prostate cancer, testicular cancer, colorectal cancer, pancreatic cancer, liver cancer, stomach cancer, biliary tract cancer, esophageal cancer, gastrointestinal stromal tumor, breast cancer, cervical cancer, ovarian cancer, uterine cancer, leukemia, lymphomas, multiple myeloma, melanoma, basal cell carcinoma, squamous cell carcinoma, bladder cancer, renal cancer, sarcoma, mesothelioma, thymoma, myelodysplastic syndrome, or myeloproliferative disease.

The autoimmune diseases that can be affected using compounds and compositions according to the invention include, but are not limited to allergy, Alzheimer's disease, acute disseminated encephalomyelitis, Addison's disease, ankylosing spondylitis, antiphospholipid antibody syndrome, asthma, atherosclerosis, autoimmune hemolytic anemia, autoimmune hemolytic and thrombocytopenic states, autoimmune hepatitis, autoimmune inner ear disease, bullous pemphigoid, coeliac disease, chagas disease, chronic obstructive pulmonary disease, chronic Idiopathic thrombocytopenic purpura (ITP), churg-strauss syndrome, Crohn's disease, dermatomyositis, diabetes mellitus type 1, endometriosis, Goodpasture's syndrome (and associated glomerulonephritis and pulmonary hemorrhage), graves' disease, guillain-barre syndrome, hashimoto's disease, hidradenitis suppurativa, idiopathic thrombocytopenic purpura, interstitial cystitis, irritable bowel syndrome, lupus erythematosus, morphea, multiple sclerosis, myasthenia gravis, narcolepsy, neuromyotonia, Parkinson's disease, pemphigus vulgaris, pernicious anaemia, polymyositis, primary biliary cirrhosis, psoriasis, psoriatic arthritis, rheumatoid arthritis, schizophrenia, septic shock, scleroderma, Sjogren's disease, systemic lupus erythematosus (and associated glomerulonephritis), temporal arteritis, tissue graft rejection and hyperacute rejection of transplanted organs, vasculitis (ANCA-associated and other vasculitides), vitiligo, and wegener's granulomatosis.

It should be understood that the invention is not limited to the particular embodiments shown and described herein, but that various changes and modifications may be made without departing from the spirit and scope of the invention as defined by the claims.

The compounds according to the present invention may be synthesized according to a variety of schemes. Necessary starting materials may be obtained by standard procedures of organic chemistry. The compounds and processes of the present invention will be better understood in connection with the following representative synthetic schemes and examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

A typical approach to synthesize of the intermediate

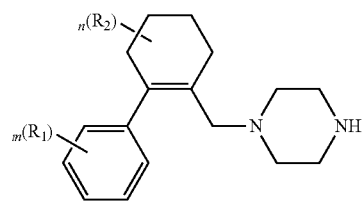

is described in Scheme 1 below: $R_1$, $R_2$, m, and n, in general Scheme 1 are the same as those described in the Summary section above.

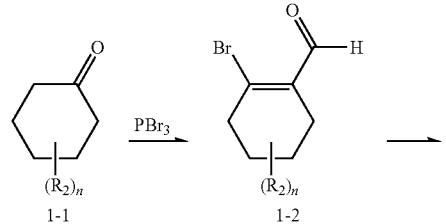

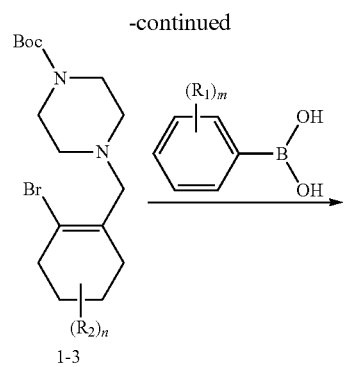

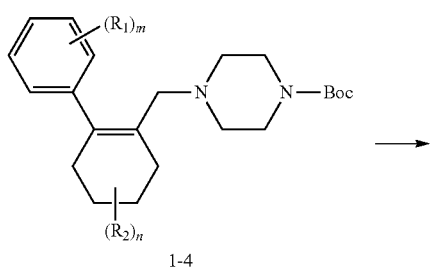

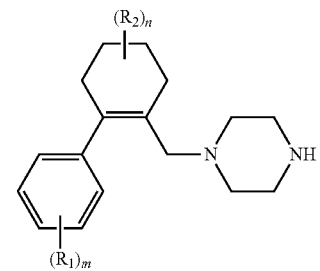

In Scheme 1, the appropriate ketone starting material 1-1 can react with tribromophosphine to form the aldehyde intermediate 1-2, which can couple with Boc-protected piperazine to form the intermediate 1-3. After that, 1-3 will couple with appropriate phenylboronic acid via a Suzuki reaction to form intermediate 1-4, followed by a de-boc process to yield key intermediate 1-5.

A typical approach to synthesize of the intermediate

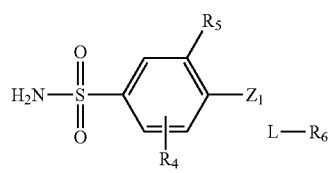

in which $R_5$ is $NO_2$ is described in Scheme 2 below. $R_4$, $R_5$, L, and $R_6$, in general Scheme 2 are the same as those described in the Summary section above.

Scheme 2

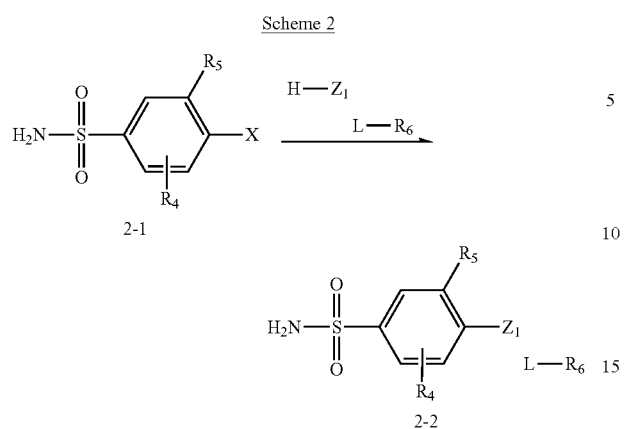

In Scheme 2, the starting material 2-1 reacts with appropriate alcohol or amine will yield 2-2.

A typical approach to synthesize of

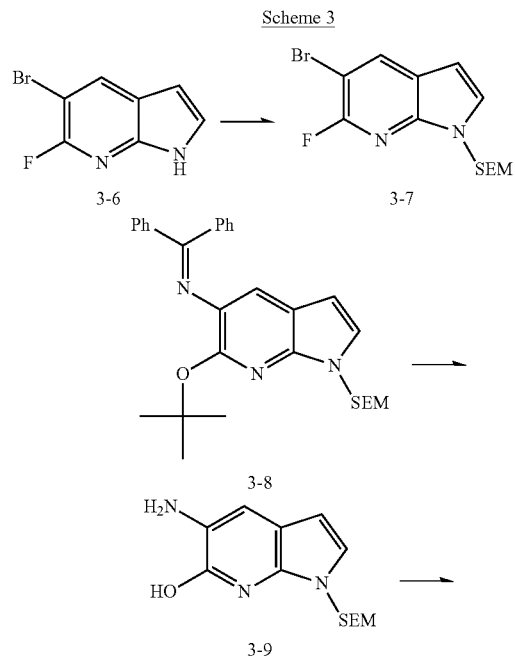

is described in Scheme 3 below. In Scheme 3, the intermediate 3-6 is commercially available. Protection of free NH of 3-6 yields 3-7, which is converted to 3-8 via Buckwald coupling and nucleophilic aromatic substitution. Double deprotection gives 3-9, which is O-alkylated to afford ester 3-10 and subsequently undergoes ring closure to form 3-11. Reduction of 3-11 produces intermediate 3-12.

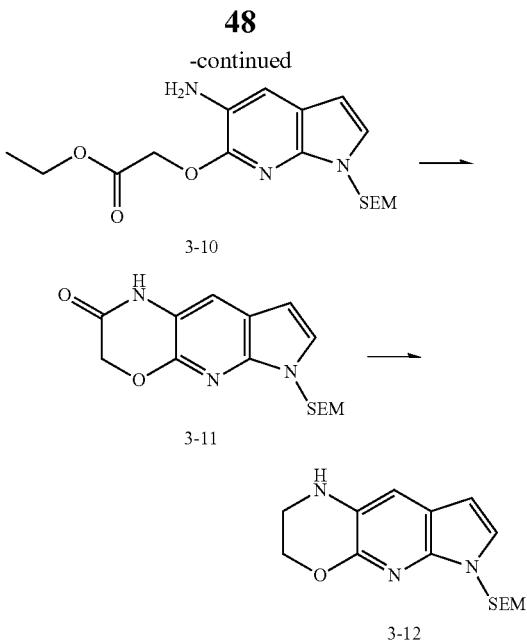

A typical approach to synthesize of

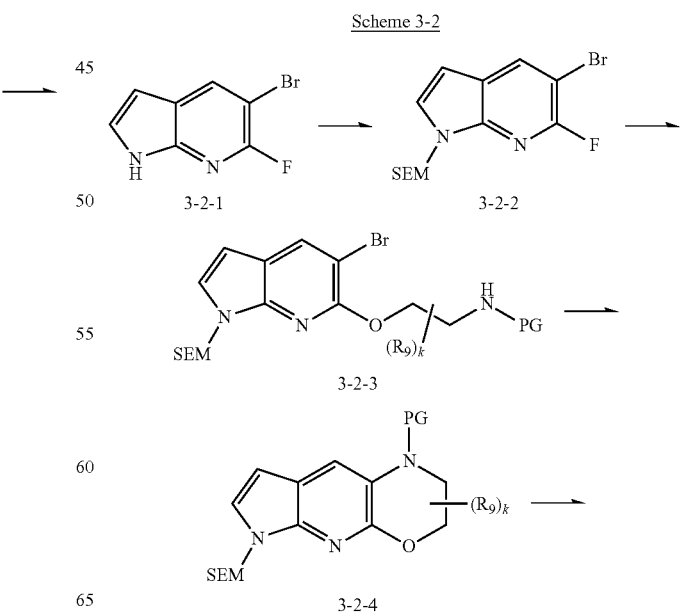

in which $R_9$ and k are the same as those described in the Summary section above is described in Scheme 3-2 (Method A), 3-3 (Method B), 3-4 (Method C) below.

Method A

-continued

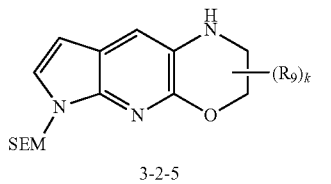
3-2-5

In Scheme 3-2, the protection of free NH of commercially available starting material 3-2-1 yields 3-2-2, which is converted to 3-2-3 via nucleophilic aromatic substitution (PG=Boc, Ts). 3-2-3 undergoes ring closure via Buchwald coupling to give 3-2-4, which is deprotected to afford intermediate 3-2-5.

Method B

Scheme 3-3

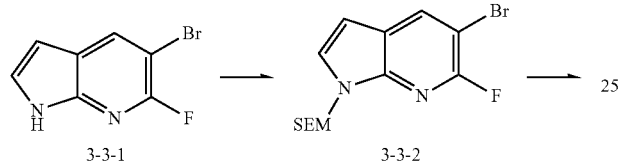

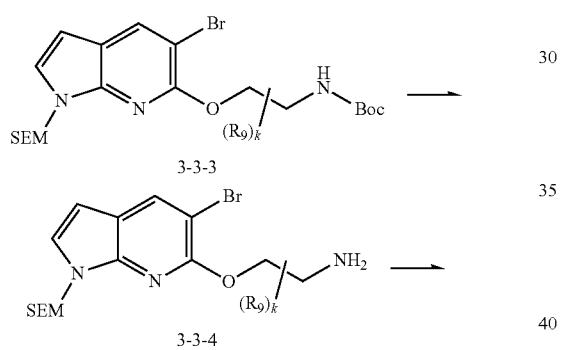

In Scheme 3-3, the protection of free NH of commercially available starting material 3-3-1 yields 3-3-2, which is converted to 3-3-3 via nucleophilic aromatic substitution. Deprotection affords 3-3-4 and subsequently, Buchwald ring closure to produce intermediate 3-3-5.

Method C

Scheme 3-4

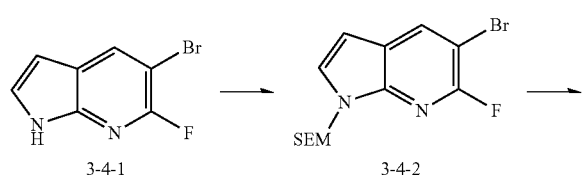

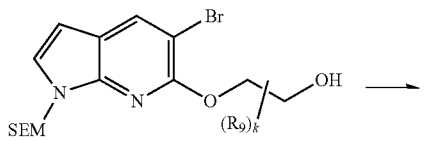
3-4-3

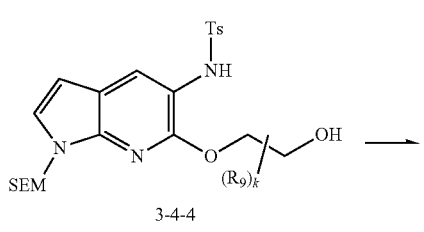
3-4-4

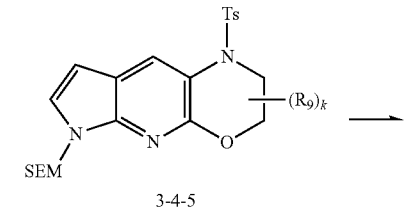
3-4-5

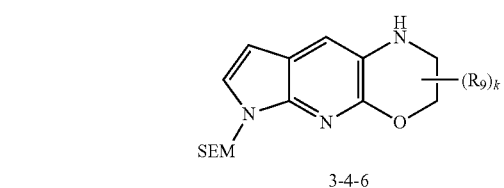
3-4-6

In Scheme 3-4, the protection of free NH of commercially available starting material 3-4-1 yields 3-4-2, which is converted to 3-4-4 via nucleophilic aromatic substitution and followed by Buchwald or Ullmann coupling. Mitsunobu reaction of 3-4-4 gives 3-4-5 which is deprotected to produce intermediate 3-4-6.

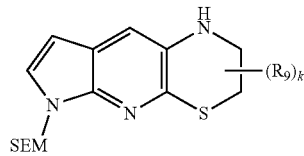

A typical approach to synthesize of in which $R_9$ and k are the same as those described in the Summary section above is described in Scheme 3-5 (Method A), below.

Method A

Scheme 3-5

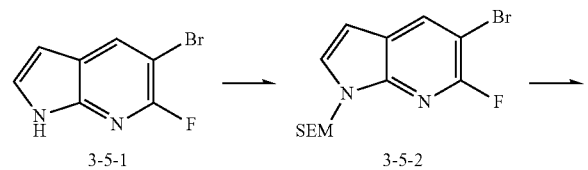

-continued

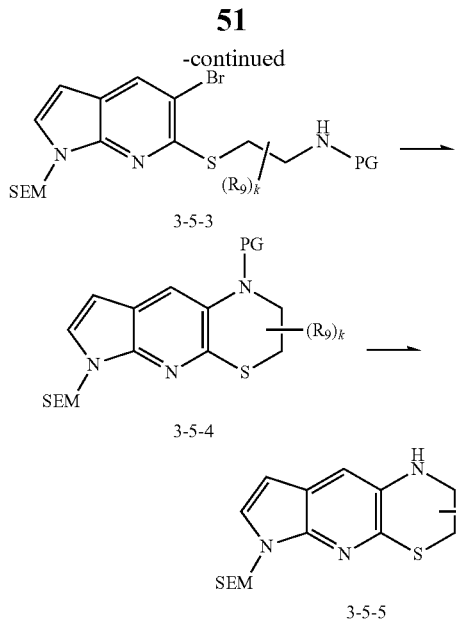

3-5-3

3-5-4

3-5-5

In Scheme 3-5, the protection of free NH of commercially available starting material 3-5-1 yields 3-5-2, which is converted to 3-5-3 via nucleophilic aromatic substitution (PG=Boc, Ts). 3-5-3 undergoes ring closure via Buchwald coupling to give 3-5-4, which is deprotected to afford intermediate 3-5-5.

A typical approach to synthesize of

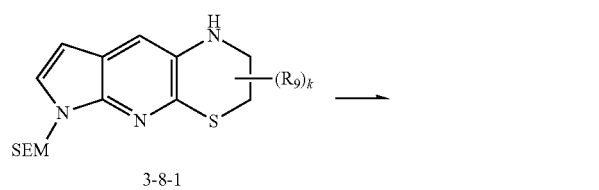

in which $R_9$ and k are the same as those described in the Summary section above is described in Scheme 3-8 below.

Scheme 3-8

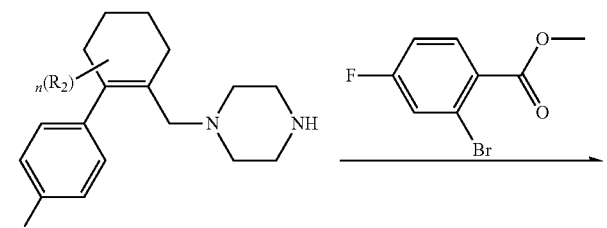

3-8-1

-continued

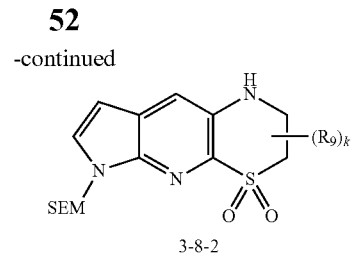

3-8-2

In Scheme 3-8, the thioether N-oxidation of 3-8-1 (which is synthesized from Scheme 3-5, 3-6, 3-7) reacts with m-CPBA to form 3-8-2.

The intermediates of

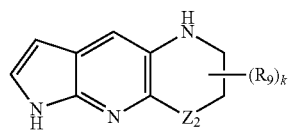

in which and k are the same as those described in the Summary section above can be made by routes similar to Scheme 3, Scheme 3-2 (Method A), 3-3 (Method B), 3-4 (Method C), Scheme 3-5, and Scheme 3-8.

Other intermediates of

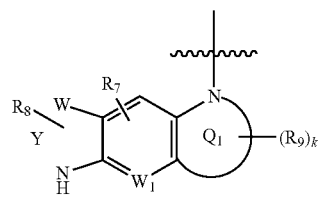

in which Q is a 6 membered ring, $R_7$, $R_8$, $R_9$, Y, W, $W_1$, and k are the same as those described in the Summary section above can be made by routes similar to Scheme 3, Scheme 3-2 (Method A), 3-3 (Method B), 3-4 (Method C), Scheme 3-5, and Scheme 3-8.

A typical approach to synthesize of Formula (D) compounds in which $Z_2$ is O is described in Scheme I:

1-5

-continued
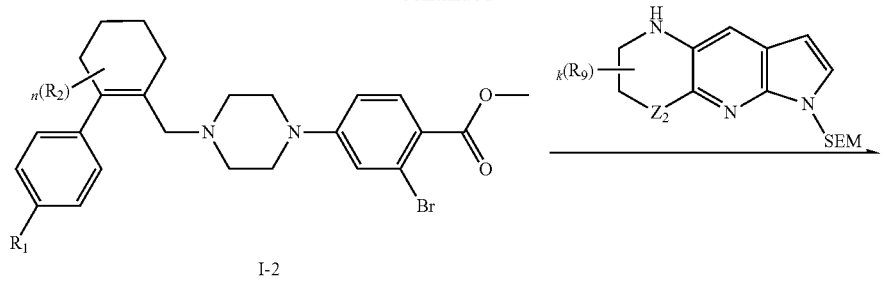
I-2
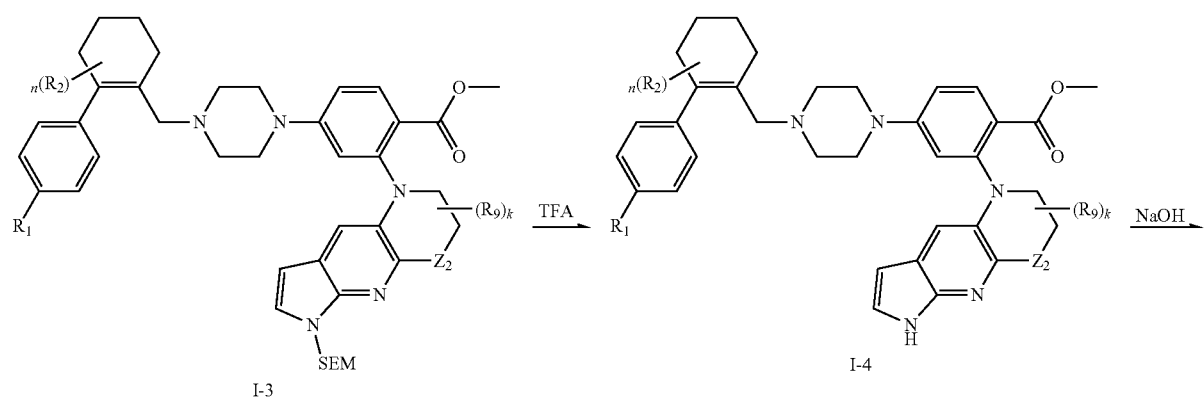
I-3 → (TFA) → I-4 → (NaOH)
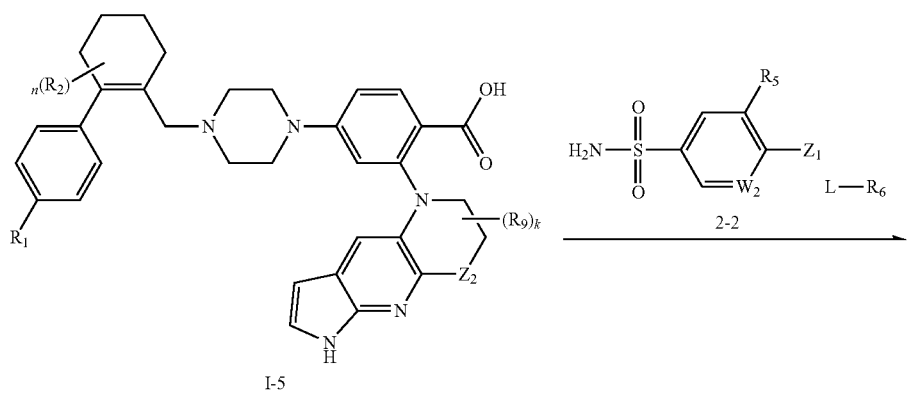
I-5
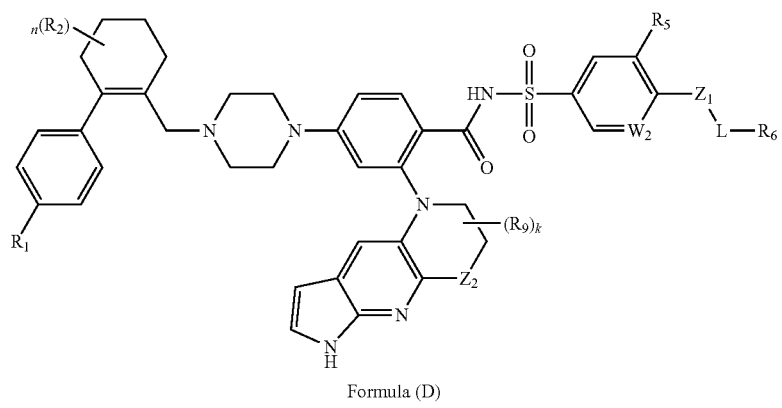
Formula (D)

In Scheme I, the intermediate 1-5 undergoes nucleophilic aromatic substitution with selected p-fluoro-2-bromo-benzoate to give 1-2. Buckwald coupling of 1-2 with appropriate amine intermediate yields 1-3. 1-3 is deprotected sequentially with TFA to remove SEM group and NaOH to remove ester group, producing free carboxylic acid intermediate I-5. Coupling of I-5 with 2-2 affords final product with Formula (D).

The compound of Formula (D) with different Z can be prepared by the method similar to the General Scheme I by using appropriate staring materials and intermediates.

The compound of Formula (C), (B), and (A) can be prepared by the method similar to the General Scheme I by using appropriate staring materials and intermediates.

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Where NMR data are presented, $^1$H spectra were obtained on XL400 (400 MHz) and are reported as ppm down field from Me$_4$Si with number of protons, multiplicities, and coupling constants in Hertz indicated parenthetically. Where HPLC data are presented, analyses were performed using an Agilent 1100 system. Where LC/MS data are presented, analyses were performed using an Applied Biosystems API-100 mass spectrometer and Shimadzu SCL-10A LC column:

Example 1-1: Preparation of 1-((4'-chloro-5,5-dimethyl-3,4,5,6-tetrahydro-[1,1'-biphenyl]-2-yl)methyl) piperazine Synthesis of 2-bromo-4,4-dimethylcyclohex-1-enecarbaldehyde 2: A solution of anhydrous chloroform (57 ml) and anhydrous N,N-dimethylformamide (9 mL) was cooled to 3° C. (internal temperature) under nitrogen before phosphorus tribromide (10 mL, 0.1 mol) was introduced dropwise at a rate so that the reaction was maintained at 3° C. After the addition was complete the reaction was allowed to warm slowly to 10° C. and then the temperature was raised to 70° C. where it was maintained for 30 min. The reaction was cooled to rt and 3,3-dimethylcyclohexanone 1 (5 g, 0.04 mol) was added slowly over 20 min. After the addition was complete the reaction was warmed to 70° C. and it was stirred for 1.5 h. The mixture was then cooled to 0° C. and a solution of 4M sodium acetate (53 ml) was added slowly. The pH of the resulting solution was adjusted to 7 using a solution of 5M NaOH and the mixture was then extracted with heptanes (100 mL×3). The combined organic fractions were dried (Na$_2$SO$_4$), filtered and concentrated under reduced pressure to give 2-bromo-4,4-dimethylcyclohex-1-enecarbaldehyde 2 (4 g, 49%) as a yellow oil.

Synthesis of 2-(4-chlorophenyl)-4,4-dimethylcyclohex-1-enecarbaldehyde 3: To a degassed solution of 2-bromo-4,4-dimethylcyclohex-1-enecarbaldehyde 2 (5 g, 0.023 mol) and 4-chlorophenyl boronic acid (3.6 g, 0.023 mol) in 1,4-dioxane (50 mL) at rt was added a solution of 2M Na$_2$CO$_3$ (20.4 ml). Nitrogen was bubbled through the mixture for 2 min and then PdCl$_2$(dppf) (0.5 g) was added. The reaction flask was heated to 120° C. where it was maintained for 3 h. After this time the suspension was cooled to rt and filtered through Celite. The collected solids were washed with additional dichloromethane and the combined filtrate and washings were concentrated under reduced pressure. Purification by column chromatography on silica with PE:EA=20:1 gave 2-(4-chlorophenyl)-4,4-dimethylcyclohex-1-enecarbaldehyde 3 (3 g, 53%) as a white solid. MS: 249[M+H]$^+$ Synthesis of (2-(4-chlorophenyl)-4,4-dimethylcyclohex-1-enyl)methanol 4: A solution of 2-(4-chlorophenyl)-4,4-dimethylcyclohex-1-enecarbaldehyde 3 (20 g, 80.6 mmol) in MeOH (100 mL) was cooled to 0° C., NaBH$_4$ (3.1g, 80.6 mmol) was added portionwise to the reaction at a rate so that the reaction was maintained at 0-5° C. After added, the mixture was stirred for 1 h at 0° C. Water was added slowly to the mixture and extracted with EA (200 mL×3), the organic layer was washed with brine and dried Na$_2$SO$_4$, filtered and concentrated under reduced pressure to give (2-(4-chlorophenyl)-4,4-dimethylcyclohex-1-enyl)methanol 4 (15 g, 75%) as a white solid. MS: 233[M+H—H$_2$O]$^+$ Synthesis of 1-(2-(bromomethyl)-5,5-dimethylcyclohex-1-enyl)-4-chlorobenzene 5: A solution of (2-(4-chlorophenyl)-4,4-dimethylcyclohex-1-enyl)methanol 4 (15 g, 0.060 mol) and in Et$_2$O (300 ml) was cooled to 0° C. before phosphorus tribromide (7.5 mL) was added dropwise to the mixture, after added, the reaction mixture was stirred for 1 h at 0° C. for 90 minutes. The reaction mixture was added H$_2$O before being extracted with EA. The organic layer was washed with a saturated NaHCO$_3$ solution and brine and dried Na$_2$SO$_4$, filtered and concentrated under reduced pressure to give 1-(2-(bromomethyl)-5,5-dimethylcyclohex-1-enyl)-4-chlorobenzene 5 (18 g, 96%) as a colorless oil.

Synthesis of tert-butyl 4-((2-(4-chlorophenyl)-4,4-dimethylcyclohex-1-enyl)methyl)piperazine-1-carboxylate—To a solution of 1-bromo-2-(bromomethyl)-5,5-dimethylcyclohex-1-ene 5 (21 g, 0.067 mol) and tert-butyl piperazine-1-carboxylate (12.4 g, 0.067 mol) in dichloromethane (200 ml) at rt was added TEA (12.2 g, 0.12 mol). The reaction was stirred for 2 h. The reaction mixture was concentrated under reduced pressure to give the crude product. Purification by column chromatography on silica with PE:EA=20:1 provided tert-butyl 4-((2-(4-chlorophenyl)-4,4-dimethylcyclohex-1-enyl)methyl)piperazine-1-carboxylate 6 (21 g, 75%).

Synthesis of 1-((2-(4-chlorophenyl)-4,4-dimethylcyclohex-1-enyl)methyl)piperazine hydrogen chloride: To a solution of tert-butyl 4-((2-(4-chlorophenyl)-4,4-dimethylcyclohex-1-enyl)methyl)piperazine-1-carboxylate 6 (30 g, 0.072 mol) in MeOH (20 ml) was added conc. HCl (50 mL). The reaction was stirred for 24 hours and then concentrated under reduced pressure. A saturated solution of Na$_2$CO$_3$ was added to adjust the pH to 8-9 and the mixture was extracted with dichloromethane (×2). The combined extracts were washed with brine, dried (Na$_2$SO$_4$), filtered and concentrated under reduced pressure. The oil product was treated with MeOH/HCl(g) (3M, 500 mL) and stirred for 1 hour, then concentrated under reduced pressure to get the product 14(2-(4-chlorophenyl)-4,4-dimethylcyclohex-1-enyl) methyl)piperazine hydrogen chloride IM-14-1 (23 g, 83%). MS: 319[M+H]$^+$. $^1$H NMR (400 MHz, DMSO) δ 11.51 (s, 1H), 9.60 (s, 1H), 9.18 (s, 1H), 7.45 (d, J=8.2 Hz, 2H), 7.15 (d, J=8.0 Hz, 2H), 3.43 (s, 8H), 2.84 (s, 2H), 2.39 (s, 2H), 2.03 (s, 2H), 1.45 (t, J=6.0 Hz, 2H), 0.96 (s, 6H).

Example 1-2: Preparation of 3-nitro-4-(((tetrahydro-2H-pyran-4-yl)methyl)amino)benzenesulfonamide To a 500 mL three-neck RB flask equipped with a mechanical stirrer were charged the 4-chloro-3-nitrobenzenesulfonamide (23.7 g, 100 mmol), DIPEA (12.9 g, 100 mmol), (tetrahydro-2H-pyran-4-yl)methanamine (11.5 g, 100 mmol) and acetonitrile (200 mL). The reaction mixture was adjusted to an internal temperature of 80° C. and agitated for no less than 12 hours. The product solution was cooled down to 40° C. and agitated for no less than 1 hour until precipitation observed. The product slurry was further cooled to 20° C. Water (80 mL) was slowly charged over no less than 1 hour, and the mixture cooled to 10° C. and agitated for no less than 2 hours before collected by filtration. The wet cake was washed with 1:1 mix of acetonitrile: water (40 mL). The wet cake was rinsed with water (80 mL) at 40° C. for no less than 1 hour before collected by filtration. The wet cake was rinsed with water (20 mL), and dried at 75° C. under vacuum to give the 3-nitro-4-(((tetrahydro-2H-pyran-4-yl)methyl)amino)benzenesulfonamide (24.5 g, 78%) as an orange solid. $^1$H NMR (400 MHz, DMSO) δ 8.60 (t, J=5.9 Hz, 1H), 8.48 (d, J=2.2 Hz, 1H), 7.84 (dd, J=9.2, 2.0 Hz, 1H), 7.54-7.18 (m, 3H), 3.86 (dd, J=11.3, 3.2 Hz, 2H), 3.35 (s, 2H), 3.27 (t, J=10.9 Hz, 2H), 1.92 (ddd, J=11.2, 7.4, 3.9 Hz, 1H), 1.62 (d, J=11.4 Hz, 2H), 1.27 (qd, J=12.3, 4.4 Hz, 2H).

Example 1-3: Preparation of 3-nitro-4-(((tetrahydro-2H-pyran-4-yl)methyl)amino)benzenesulfonamide Into a 50-mL round-bottom flask, was placed (4-fluorooxan-4-yl)methanamine hydrochloride (500 mg, 2.95 mmol, 1.00 equiv), 4-fluoro-3-nitrobenzene-1-sulfonamide (650 mg, 2.95 mmol, 1.00 equiv), tetrahydrofuran (15 mL), $Cs_2CO_3$ (2.8 g, 8.59 mmol, 3.00 equiv). The resulting solution was stirred for 14 h at 50° C. in an oil bath. The reaction mixture was cooled to room temperature. The resulting mixture was filtered and concentrated under vacuum. The residue was applied onto a silica gel column with ethyl acetate/petroleum ether (4:1). This resulted in 650 mg (66%) of 4-[[(4-fluorooxan-4-yl)methyl]amino]-3-nitrobenzene-1-sulfonamide as a yellow solid. LCMS (ES, m/z): M+1: 334. H-NMR: (300 MHz, DMSO, ppm): δ 8.58 (t, J=6.3 Hz, 1H), 8.49 (d, J=2.1 Hz, 1H), 7.90-7.80 (m, 1H), 7.44 (d, J=9.3 Hz, 1H), 7.34 (s, 2H), 3.87-3.70 (m, 4H), 3.61-3.50 (m, 2H), 1.95-1.70 (m, 4H).

Example 1-4: Improved method for the synthesis of 64(2-(trimethylsilyl)ethoxy)methyl)-1,2,3,6-tetrahydropyrrolo[3',2':5,6]pyrido[2,3-b][1,4]oxazine Into a 250-mL 3-necked round-bottom flask, was placed 6-fluoropyridin-2-amine (11.2 g, 99.91 mmol, 1.00 equiv), $CH_3CN$ (100 mL), NBS (21.4 g, 120.24 mmol, 1.20 equiv). The resulting solution was stirred for overnight at room temperature. The reaction was then quenched by the addition of 200 mL of water. The resulting solution was extracted with 3×100 mL of ethyl acetate and the organic layers combined. The resulting mixture was washed with 3×100 mL of brine. The mixture was dried over anhydrous sodium sulfate, then filtered and concentrated under vacuum. The residue was applied onto a silica gel column with ethyl acetate/petroleum ether (0:1-1:5). This resulted in 12 g (63%) of 5-bromo-6-fluoropyridin-2-amine as a white solid. LCMS (ES, m/z): M+1: 191, 193.

Into a 2000-mL 4-necked round-bottom flask, was placed 5-bromo-6-fluoropyridin-2-amine (110 g, 575.91 mmol, 1.00 equiv) in, AcOH (1000 mL), iodo(sulfanyl)amine (142.5 g, 633.35 mmol, 1.10 equiv). The resulting solution was stirred for overnight at room temperature. The reaction was then quenched by the addition of 3000 mL of water. The solids were collected by filtration. This resulted in 170 g (93%) of 5-bromo-6-fluoro-3-iodopyridin-2-amine as a white solid. H-NMR: (CDCl$_3$, 300 MHz) 5: 7.98 (d, J=14.4 Hz, 1H), 4.94-5.00 (bs, 2H).

Into a 3000-mL 3-necked round-bottom flask, was placed a solution of 5-bromo-6-fluoro-3-iodopyridin-2-amine (170 g, 536.45 mmol, 1.00 equiv) in tetrahydrofuran (1500 mL), CuI (10.2 g, 53.56 mmol, 0.10 equiv), TEA (500 mL), dichloropalladium; bis(triphenylphosphane) (11.2 g, 15.96 mmol, 0.03 equiv), ethyl(ethynyl)dimethylsilane (63 g, 561.27 mmol, 1.20 equiv). The resulting solution was stirred for 1 overnight at room temperature. The reaction was then quenched by the addition of 2000 mL of water. The resulting solution was extracted with 3×1000 mL of ethyl acetate and the organic layers combined. The resulting mixture was washed with 3×1000 mL of brine. The mixture was dried over anhydrous sodium sulfate, then filtered and concentrated under vacuum. The residue was applied onto a silica gel column with ethyl acetate/petroleum ether (0:1-1:1). This resulted in 120 g (78%) of 5-bromo-6-fluoro-3-[2-(trimethylsilyl)ethynyl]pyridin-2-amine as yellow oil. LCMS (ES, m/z): M+1: 289, 287

Into a 2000-mL 4-necked round-bottom flask, was placed a solution of 5-bromo-6-fluoro-3-[2-(trimethylsilyl)ethynyl] pyridin-2-amine (84 g, 292.48 mmol, 1.00 equiv) in dichloromethane (1000 mL), pyridine (57.8 g, 730.72 mmol, 2.50 equiv). This was followed by the addition of acetyl chloride (50.2 g, 639.51 mmol, 2.20 equiv) dropwise with stirring at 0 degree. The resulting solution was stirred for overnight at room temperature. The reaction was then quenched by the addition of 1000 L of water. The resulting mixture was washed with 2×1000 mL of water. The mixture was dried over anhydrous sodium sulfate and concentrated under vacuum. The residue was applied onto a silica gel column with ethyl acetate/petroleum ether (0:1-1:10). This resulted in 80 g (83%) of N-[5-bromo-6-fluoro-3-[2-(trimethylsilyl)ethynyl]pyridin-2-yl]acetamide as a white solid. LC-MS: (ES, m/z): M+1=331, R,T=1.669 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient Into a 2000-mL round-bottom flask, was placed a solution of N-[5-bromo-6-fluoro-3-[2-(trimethylsilyl)ethynyl]pyridin-2-yl]acetamide (80 g, 242.98 mmol, 1.00 equiv) in tetrahydrofuran (300 mL), TBAF (1M in tetrahydrofuran) (729 mL, 3.00 equiv). The resulting solution was stirred for 12 h at 70 degree. The reaction mixture was cooled to room temperature. The resulting mixture was concentrated under vacuum. The reaction was then quenched by the addition of 500 mL of water. The resulting solution was extracted with 3×300 mL of ethyl acetate and the organic layers combined. The resulting mixture was washed with 3×300 mL of brine. The mixture was dried over anhydrous sodium sulfate and concentrated under vacuum. The residue was applied onto a silica gel column with ethyl acetate/petroleum ether (0:1-4: 1). This resulted in 15 g (29%) of 5-bromo-6-fluoro-1H-pyrrolo[2,3-b]pyridine as a white solid. LC-MS: (ES, m/z): M+1=213, R,T=1.451 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient Into a 250-mL 3-necked round-bottom flask purged and maintained with an inert atmosphere of nitrogen, was placed a solution of 5-bromo-6-fluoro-1H-pyrrolo[2,3-b]pyridine (15 g, 69.76 mmol, 1.00 equiv) in N,N-dimethylformamide (150 mL). This was followed by the addition of sodium hydride (4.2 g, 175.00 mmol, 1.50 equiv), in portions at 0 degree. After 0.5 h stirring, to this was added SEMCl (14 g, 84.34 mmol, 1.20 equiv) dropwise with stirring at 0 degree. The resulting solution was allowed to react, with stirring, for an additional 3 h at room temperature. The reaction was then quenched by the addition of 300 mL of water. The resulting solution was extracted with 3×200 mL of ethyl acetate and the organic layers combined. The resulting mixture was washed with 3×200 mL of brine. The mixture was dried over anhydrous sodium sulfate and concentrated under vacuum. The residue was applied onto a silica gel column with ethyl acetate/petroleum ether (0:1-1:10). This resulted in 15 g (62%) of 5-bromo-6-fluoro-1-[[2-(trimethylsilyl)ethoxy]methyl]-1H-pyrrolo[2,3-b]pyridine as yellow oil. H-NMR–: (CDCl$_3$, 300 MHz) δ: 8.19 (d, J=8.7 Hz, 1H), 7.37 (d, J=3.6 Hz, 1H), 6.54 (d, J=3.6 Hz, 1H), 5.64 (s, 2H), 3.58 (t, J=8.1 Hz, 2H), 0.98-0.93 (t, J=8.1 Hz, 2H), 0.00 (s, 9H). The measurements of the NMR spectra were done with BrukerAvanceIII HD 300 MHz with a probe head of BBOF Into a 250-mL round-bottom flask, was placed a solution of 5-bromo-6-fluoro-1-[[2-(trimethylsilyl)ethoxy]methyl]-1H-pyrrolo[2,3-b]pyridine (6.9 g, 19.98 mmol, 1.00 equiv) in dioxane (70 mL), t-BuOK (6.84 g, 60.96 mmol, 3.00 equiv), x-antphos (2.3 g, 3.98 mmol, 0.20 equiv), Pd$_2$(dba)$_3$.CHCl$_3$ (1.9 g, 0.10 equiv), diphenylmethanimine (4.32 g, 23.84 mmol, 1.20 equiv). The resulting solution was stirred for overnight at 100° C. The resulting mixture was concentrated under vacuum. The residue was applied onto a silica gel column with ethyl acetate/petroleum ether (0:1-1:20). This resulted in 3.6 g (crude) of 6-(tert-butoxy)-N-(diphenylmethylidene)-1-[[2-(trimethylsilyl)ethoxy]methyl]-1H-pyrrolo[2,3-b]pyridin-5-amine as white oil. LC-MS–: (ES, m/z): M+1=500.

Into a 50-mL round-bottom flask, was placed a solution of 6-(tert-butoxy)-N-(diphenylmethylidene)-1-[[2-(trimethylsilyl)ethoxy]methyl]-1H-pyrrolo[2,3-b]pyridin-5-amine (3.6 g, 7.20 mmol, 1.00 equiv) in dioxane (15 mL), 4M HCl in dioxane (20 mL). The resulting solution was stirred for 2 h at room temperature. The reaction was then quenched by the addition of 50 mL of satu. sodium bicarbonate. The solids were collected by filtration. This resulted in 1 g (50%) of 5-amino-1-[[2-(trimethylsilyl)ethoxy]methyl]-1H-pyrrolo[2,3-b]pyridin-6-ol as a white solid. LC-MS: (ES, m/z): M+1=280, R,T=0.811 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient Into a 100-mL round-bottom flask, was placed a solution of 5-amino-1-[[2-(trimethylsilyl)ethoxy]methyl]-1H-pyrrolo[2,3-b]pyridin-6-ol (1 g, 3.58 mmol, 1.00 equiv) in CH$_3$CN (50 mL), Cs$_2$CO$_3$ (1.75 g, 5.37 mmol, 1.50 equiv), ethyl 2-chloroacetate (438 mg, 3.57 mmol, 1.00 equiv). The resulting solution was stirred for 2 h at 70 degree. The reaction mixture was cooled to room temperature. The reaction was then quenched by the addition of 50 mL of water. The resulting solution was extracted with 3×50 mL of ethyl acetate and the organic layers combined. The resulting mixture was washed with 3×50 mL of brine. The mixture was dried over anhydrous sodium sulfate, then filtered and concentrated under vacuum. The residue was applied onto a silica gel column with ethyl acetate/petroleum ether (0:1-1:1). This resulted in 1 g (76%) of ethyl 2-[(5-amino-1-[[2-(trimethylsilyl)ethoxy]methyl]-1H-pyrrolo[2,3-b]pyridin-6-yl)oxy]acetate as a white solid. LC-MS: (ES, m/z): M+1=366.

Into a 100-mL round-bottom flask, was placed a solution of ethyl 2-[(5-amino-1-[[2-(trimethylsilyl)ethoxy]methyl]-1H-pyrrolo[2,3-b]pyridin-6-yl)oxy]acetate (1 g, 2.74 mmol, 1.00 equiv) in ethanol (20 mL), Cs$_2$CO$_3$ (1.78 g, 5.46 mmol, 2.00 equiv). The resulting solution was stirred for overnight at reflux. The reaction mixture was cooled to room temperature. The resulting mixture was filtered and concentrated under vacuum. The residue was applied onto a silica gel column with ethyl acetate/petroleum ether (0:1-1:2). This resulted in 400 mg (46%) of 4-[[2-(trimethylsilyl)ethoxy]methyl]-13-oxa-2,4,10-triazatricyclo[7.4.0.0ˆ[3,7]]trideca-1(9),2,5,7-tetraen-11-one as a white solid. LC-MS: (ES, m/z): M+1=320.

Into a 25-mL round-bottom flask purged and maintained with an inert atmosphere of nitrogen, was placed a solution of 4-[[2-(trimethylsilyl)ethoxy]methyl]-13-oxa-2,4,10-triazatricyclo[7.4.0.0ˆ[3,7]]trideca-1(9),2,5,7-tetraen-11-one (400 mg, 1.25 mmol, 1.00 equiv) in tetrahydrofuran (mL). This was followed by the addition of LiAlH$_4$ (95 mg, 2.50 mmol, 2.00 equiv), in portions at −78 degree. The resulting solution was stirred for 4 h at room temperature. The reaction was then quenched by the addition of 20 mL of water. The solids were filtered out. The resulting solution was extracted with 3×20 mL of ethyl acetate and the organic layers combined. The resulting mixture was washed with 3×20 mL of brine. The mixture was dried over anhydrous sodium sulfate and concentrated under vacuum. The residue was applied onto a silica gel column with ethyl acetate/petroleum ether (0:1-1:1). This resulted in 180 mg (47%) of 4-[[2-(trimethylsilyl)ethoxy]methyl]-13-oxa-2,4,10-triazatricyclo[7.4.0.0ˆ[3,7]]trideca-1(9),2,5,7-tetraene as brown oil. H-NMR: (CDCl$_3$, 300 MHz) δ: 7.36 (s, 1H), 7.28 (s, 1H), 7.25 (d, J=3.3 Hz, 1H), 6.31 (d, J=3.3 Hz, 1H), 5.58 (s, 2H), 4.48-4.52 (m, 2H), 3.72-3.60 (m, 2H), 3.60-3.52 (m, 2H), 0.92-0.87 (m, 2H), 0.00 (s, 9H).

Example 2: Preparation of NW-4-8 which was Disclosed in Our Previous Application WO/2017/132474, by Using the Intermediate of Example 1-4 Above Into a 250-mL round-bottom flask, was placed a solution of 1-[[2-(4-chlorophenyl)-4,4-dimethylcyclohex-1-en-1-yl]methyl]piperazine (15.09 g, 47.32 mmol, 1.00 equiv) in DMA (150 mL), DIEA (12.9 g, 99.81 mmol, 2.00 equiv), methyl 2-bromo-4-fluorobenzoate (11.6 g, 49.78 mmol, 1.00 equiv). The resulting solution was stirred for 12 h at 100 degree. The reaction mixture was cooled to room temperature. The reaction was then quenched by the addition of 50 mL of water. The resulting solution was extracted with 3×100 mL of ethyl acetate and the organic layers combined. The resulting mixture was washed with 3×100 mL of brine. The mixture was dried over anhydrous sodium sulfate, then filtered and concentrated under vacuum. The residue was applied onto a silica gel column with ethyl acetate/petroleum ether (0:1-1:5). This resulted in 7 g (crude) of methyl 2-bromo-4-(4-[[2-(4-chlorophenyl)-4,4-dimethylcyclohex-1-en-1-yl]methyl]piperazin-1-yl)benzoate as yellow oil. LC-MS (ES, m/z): M+1=533, 531.

Into a 40-mL round-bottom flask, was placed a solution of 4-[[2-(trimethylsilyl)ethoxy]methyl]-13-oxa-2,4,10-triazatricyclo[7.4.0.0ˆ[3,7]]trideca-1,3(7),5,8-tetraene (175 mg, 0.57 mmol, 1.00 equiv) in dioxane (10 mL), Cs$_2$CO$_3$ (560 mg, 1.72 mmol, 3.00 equiv), XantPhos Pd G2 (CAS: 1375325-77-1) (53 mg, 0.06 mmol, 0.10 equiv), methyl 2-bromo-4-(4-[2-(4-chlorophenyl)-4,4-dimethylcyclohex-1-en-1-yl]methylpiperazin-1-yl)benzoate (334.7 mg, 0.63 mmol, 1.10 equiv). The resulting solution was stirred for 2 h at 110 degree. The reaction mixture was cooled to room temperature. The solids were filtered out. The resulting mixture was concentrated under vacuum. The residue was applied onto a silica gel column with ethyl acetate/petroleum ether (0:1-1:3). This resulted in 200 mg (46%) of methyl 4-(4-[2-(4-chlorophenyl)-4,4-dimethylcyclohex-1-en-1-yl]methylpiperazin-1-yl)-2-(4-[[2-(trimethylsilyl)ethoxy]methyl]-13-oxa-2,4,10-triazatricyclo[7.4.0.0^[3,7]]trideca-1,3(7),5,8-tetraen-10-yl)benzoate as yellow oil. LC-MS: (ES, m/z): M+1=756, R,T=1.252 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient.

Into a 50-mL round-bottom flask, was placed a solution of methyl 4-(4-[[2-(4-chlorophenyl)-4,4-dimethylcyclohex-1-en-1-yl]methyl]piperazin-1-yl)-2-(4-[[2-(trimethylsilyl)ethoxy]methyl]-13-oxa-2,4,10-triazatricyclo[7.4.0.0^[3,7]]trideca-1,3(7),5,8-tetraen-10-yl)benzoate (200 mg, 0.26 mmol, 1.00 equiv) in tetrahydrofuran (20 mL), TBAF (3 mg, 0.01 mmol), ethane-1,2-diamine (3 mL). The resulting solution was stirred for 24 h at 60 degree. The reaction mixture was cooled to room temperature. The reaction was then quenched by the addition of 30 mL of water. The resulting solution was extracted with 2×30 mL of ethyl acetate and the organic layers combined. The resulting mixture was washed with 2×30 mL of brine. The mixture was dried over anhydrous sodium sulfate and concentrated under vacuum. The residue was applied onto a silica gel column with ethyl acetate/petroleum ether (0:1-1:2). This resulted in 90 mg (54%) of methyl 4-(4-[[2-(4-chlorophenyl)-4,4-dimethylcyclohex-1-en-1-yl]methyl]piperazin-1-yl)-2-[13-oxa-2,4,10-triazatricyclo[7.4.0.0^[3,7]]trideca-1,3(7),5,8-tetraen-10-yl]benzoate as a yellow solid. LC-MS (ES, m/z): M+1=626, R,T=1.052 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient.

Into a 8-mL round-bottom flask, was placed a solution of methyl 4-(4-[[2-(4-chlorophenyl)-4,4-dimethylcyclohex-1-en-1-yl]methyl]piperazin-1-yl)-2-[13-oxa-2,4,10-triazatricyclo[7.4.0.0^[3,7]]trideca-1,3(7),5,8-tetraen-10-yl]benzoate (90 mg, 0.14 mmol, 1.00 equiv) in tetrahydrofuran/MeOH/H$_2$O (2/2/2 mL), sodium hydroxide (23 mg, 0.57 mmol, 4.00 equiv). The resulting solution was stirred for overnight at 60 degree. The reaction mixture was cooled to room temperature. The reaction was then quenched by the addition of 5 mL of water. The pH value of the solution was adjusted to 6 with hydrogen chloride (1 mol/L). The resulting solution was extracted with 2×10 mL of ethyl acetate and the organic layers combined. The resulting mixture was washed with 3×10 mL of brine. The mixture was dried over anhydrous sodium sulfate and concentrated under vacuum. The residue was applied onto a silica gel column with ethyl acetate/petroleum ether (0:1-1:1). This resulted in 70 mg (80%) of 4-(4-[[2-(4-chlorophenyl)-4,4-dimethylcyclohex-1-en-1-yl]methyl]piperazin-1-yl)-2-[13-oxa-2,4,10-triazatricyclo[7.4.0.0^[3,7]]trideca-1,3(7),5,8-tetraen-10-yl]benzoic acid as a yellow solid.

LC-MS (ES, m/z): M+1=612, R,T=1.005 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient.

Into a 8-mL round-bottom flask, was placed a solution of 4-(4-[[2-(4-chlorophenyl)-4,4-dimethylcyclohex-1-en-1-yl]methyl]piperazin-1-yl)-2-[13-oxa-2,4,10-triazatricyclo[7.4.0.0^[3,7]]trideca-1,3(7),5,8-tetraen-10-yl]benzoic acid (35 mg, 0.06 mmol, 1.00 equiv) in dichloromethane (5 mL), 4-dimethylaminopyridine (27.8 mg, 0.23 mmol, 4.00 equiv), 3-nitro-4-[(oxan-4-ylmethyl)amino]benzene-1-sulfonamide (21.7 mg, 0.07 mmol, 1.20 equiv), EDCI (22 mg, 0.11 mmol, 2.00 equiv). The resulting solution was stirred for overnight at room temperature. The resulting mixture was concentrated under vacuum. The crude product was purified by Prep-HPLC with the following conditions (Waters-2767): Column, X-bridge RP18, 5um, 19*100 mm; mobile phase, 0.03% ammonia in water (0.03% NH4HCO3 & NH$_4$OH) and CH3CN (32% CH3CN up to 52% in 6 min); Detector, UV 254 nm. This resulted in 28.3 mg (54%) of 4-(4-[[2-(4-chlorophenyl)-4,4-dimethylcyclohex-1-en-1-yl]methyl]piperazin-1-yl)-N-([3-nitro-4-[(oxan-4-ylmethyl)amino]benzene]sulfonyl)-2-[13-oxa-2,4,10-triazatricyclo[7.4.0.0^[3,7]]trideca-1,3(7),5,8-tetraen-10-yl]benzamide as a yellow solid. LC-MS–: (ES, m/z): (ES, m/z): M+1=909, R.T=1.52 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient. H-NMR: (CDCl$_3$, 300 MHz) δ: 8.70 (s, 1H), 8.46 (m, 2H), 8.10-8.06 (m, 1H), 7.89-7.60 (m, 1H), 7.10 (s, 1H), 6.94-6.71 (m, 5H), 6.49 (s, 1H), 6.16 (s, 1H), 4.70-4.65 (m, 2H), 4.00-4.10 (m, 2H), 3.67-3.19 (m, 7H), 3.20-3.00 (m, 4H), 2.78 (s, 1H), 2.58-2.52 (m, 2H), 2.27-2.17 (m, 3H), 2.05-1.98 (m, 4H), 1.74-1.70 (m, 3H), 1.55-1.40 (m, 3H), 0.98 (s, 6H). The measurements of the NMR spectra were done with BrukerAvanceIII HD 300 MHz with a probe head of BBOF.

Example 3: Preparation of 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide Into a 8-mL round-bottom flask, was placed a solution of 4-(4-[[2-(4-chlorophenyl)-4,4-dimethylcyclohex-1-en-1-yl]methyl]piperazin-1-yl)-2-[13-oxa-2,4,10-triazatricyclo[7.4.0.0^[3,7]]trideca-1,3(7),5,8-tetraen-10-yl]benzoic acid (35 mg, 0.06 mmol, 1.00 equiv) in dichloromethane (5 mL), 4-dimethylaminopyridine (27.8 mg, 0.23 mmol, 4.00 equiv), EDCI (22 mg, 0.11 mmol, 2.00 equiv), 4-[(4-fluorooxan-4-yl)methyl]amino-3-nitrobenzene-1-sulfonamide (22.7 mg, 0.07 mmol, 1.20 equiv). The resulting solution was stirred for overnight at room temperature. The resulting mixture was concentrated under vacuum. The crude product was purified by Prep-HPLC with the following conditions (Waters-2767): Column, X-bridge RP18, 5 um, 19*100 mm; mobile phase, 0.03% ammonia in water (0.03% NH$_4$HCO$_3$ & NH$_4$OH) and CH$_3$CN (32% CH$_3$CN up to 52% in 6 min); Detector, UV 254 nm. This resulted in 26.2 mg (50%) of 4-(4-[[2-(4-chlorophenyl)-4,4-dimethylcyclohex-1-en-1-yl]methyl]piperazin-1-yl)-N-[(4-[[(4-fluorooxan-4-yl)methyl]aminol-3-nitrobenzene)sulfonyl]-2-[13-oxa-2,4,10-triazatricyclo[7.4.0.0^[3,7]]trideca-1,3(7),5,8-tetraen-10-yl]benzamide as a yellow solid. LC-MS: (ES, m/z): (ES, m/z): M+1=927, R,T=1.27 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min. H-NMR: (CDCl$_3$, 300 MHz) δ: 12.38 (bs, 1H), 8.69 (d, J=2.1 Hz, 1H), 8.58 (t, J=6.3 Hz, 1H), 8.44 (s, 1H), 8.07 (d, J=9.0 Hz, 1H), 7.90-7.87 (m, 1H), 7.24-7.22 (m, 2H), 7.08 (s, 1H), 6.94 (m, 2H), 6.85 (s, 1H), 6.80-6.77 (m, 2H), 6.49 (s, 1H), 6.14 (s, 1H), 4.74-4.67 (m, 2H), 3.91-3.80 (m, 2H), 3.80-3.44 (m, 6H), 3.17 (m, 4H), 2.77 (s, 1H), 2.22-2.10 (m, 6H), 2.00 (s, 2H), 1.98-1.75 (m, 3H), 1.80-1.60 (m, 2H), 1.55-1.40 (m, 2H), 0.94 (s, 6H). The measurements of the NMR spectra were done with BrukerAvanceIII HD 300 MHz with a probe head of BBOF.

Example 4: Preparation of 4-(4-((4'-chloro-5,5-dimethyl-3,4,5,6-tetrahydro-[1,1'-biphenyl]-2-yl)methyl) piperazin-1-yl)-2-(2,3-dihydropyrrolo[3',2':5,6] pyrido[2,3-b][1,4]oxazin-1(6H)-yl-2,2,3,3-d4)-N-((4-(((4-fluorotetrahydro-2H-pyran-4-yl)methyl) amino)-3-nitrophenyl)sulfonyl)benzamide Synthesis of 4-[[2-(trimethylsilyl)ethoxy]methyl](12,12-2H2)-13-oxa-2,4,10-triazatricyclo[7.4.0.0^[3,7]]trideca-1(9),2,5,7-tetraen-11-one: Into a 8-mL vial, was placed 4-[[2-(trimethylsilyl)ethoxy]methyl]-13-oxa-2,4,10-triazatricyclo[7.4.0.0^[3,7]]trideca-1(9),2,5,7-tetraen-11-one (90 mg, 0.28 mmol, 1 equiv), D$_2$O (1 mL), MeOD (1 mL), Na$_2$CO$_3$ (89.6 mg, 0.85 mmol, 3.00 equiv). The resulting solution was stirred for 48 h at 60° C. in an oil bath. The resulting solution was extracted with 3×3 mL of dichloromethane. The organic layer was dried over anhydrous sodium sulfate and concentrated under vacuum. This resulted in 60 mg (66%) of 4-[[2-(trimethylsilyl)ethoxy]methyl](12,12-2H2)-13-oxa-2,4,10-triazatricyclo[7.4.0.0^[3,7]]trideca-1(9),2,5,7-tetraen-11-one as a yellow solid. LC-MS-PH-PHNW-4-34-1: (ES, m/z): M+1=322. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min. H-NMR-PH-PHNW-4-34-2: (d-DMSO, 300 ppm): 7.44-7.41 (m, 2H), 6.43-6.42 (d, J=6 Hz, 1H), 5.46-5.41 (m, 2H), 3.51-3.46 (m, 2H), 1.24 (s, 1H), 0.86-0.79 (m, 4H), −0.04-0.05 (m, 9H).

Synthesis of 4-[[2-(trimethylsilyl)ethoxy]methyl](11,11,12,12-2H4)-13-oxa-2,4,10-triazatricyclo[7.4.0.0^[3,7]]trideca-1(9),2,5,7-tetraene: Into a 8-mL vial, was placed 4-[[2-(trimethylsilyl)ethoxy]methyl](12,12-2H2)-13-oxa-2,4,10-triazatricyclo[7.4.0.0^[3,7]]trideca-1(9),2,5,7-tetraen-11-one (60 mg, 0.19 mmol, 1 equiv), THF (3 mL). This was followed by the addition of LiAlD$_4$ (31.3 mg, 0.75 mmol, 3.99 equiv) in portions at 0° C. The resulting solution was stirred for overnight at room temperature. The reaction was then quenched by the addition of 1 mL of D$_2$O. The resulting solution was extracted with 3×5 mL of ethyl acetate. The organic layer was dried over anhydrous sodium sulfate and concentrated under vacuum. This resulted in 25 mg (43.28%) of 4-[[2-(trimethylsilyl)ethoxy]methyl](11,11,12,12-2H4)-13-oxa-2,4,10-triazatricyclo[7.4.0.0^[3,7]]trideca-1(9),2,5,7-tetraene as a yellow solid. LC-MS-PH-PHNW-4-34-2: (ES, m/z): M+1=931. H-NMR-PH-PHNW-4-34-2: (CDCl$_3$, 300 ppm): 7.35 (s, 1H), 7.17-7.15 (d, J=6 Hz, 1H), 6.35-6.34 (d, J=3 Hz, 1H), 5.56-5.53 (m, 2H), 3.58-3.52 (m, 2H), 2.08 (s, 1H), 1.28 (s, 1H), 0.93-0.88 (m, 3H), −0.04-0.05 (m, 9H).

Synthesis of methyl 4-(4-[[2-(4-chlorophenyl)-4,4-dimethylcyclohex-1-en-1-yl]methyl]piperazin-1-yl)-2-(4-[[2-(trimethylsilyl)ethoxy]methyl](11,11,12,12-2H4)-13-oxa-2,4,10-triazatricyclo[7.4.0.0^[3,7]]trideca-1(9),2,5,7-tetraen-10-yl)benzoate: Into a 8-mL vial, was placed 4-[[2-(trimethylsilyl)ethoxy]methyl](11,11,12,12-2H4)-13-oxa-2,4,10-triazatricyclo[7.4.0.0^[3,7]]trideca-1(9),2,5,7-tetraene (25 mg, 0.08 mmol, 1 equiv), methyl 2-bromo-4-(4-[[2-(4-chlorophenyl)-4,4-dimethylcyclohex-1-en-1-yl]methyl]piperazin-1-yl)benzoate (55.9 mg, 0.11 mmol, 1.3 equiv), Dioxane (5 mL), Cs$_2$CO$_3$ (52.6 mg, 0.16 mmol, 2 equiv), Chloro[9,9-dimethyl-4,5-bis(diphenylphosphino)xanthene][2-amino-1,1-biphenyl-2-yl]palladium(II) (5 mg). The resulting solution was stirred for 2 h at 100° C. in an oil bath. After the reaction completed, the crude solution is concentrated and the residue was applied onto a silica gel column with ethyl acetate/petroleum ether (0:1-1:1). This resulted in 20 mg (32.56%) of methyl 4-(4-[[2-(4-chlorophenyl)-4,4-dimethylcyclohex-1-en-1-yl]methyl]piperazin-1-yl)-2-(4-[[2-(trimethylsilyl)ethoxy]methyl](11,11,12,12-2H4)-13-oxa-2,4,10-triazatricyclo[7.4.0.0^[3,7]]trideca-1(9),2,5,7-tetraen-10-yl)benzoate as a yellow solid. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min.

Synthesis of methyl 4-(4-[[2-(4-chlorophenyl)-4,4-dimethylcyclohex-1-en-1-yl]methyl]piperazin-1-yl)-2-[(11,11,12,12-2H4)-13-oxa-2,4,10-triazatricyclo[7.4.0.0^[3,7]]trideca-1(9),2,5,7-tetraen-10-yl]benzoate. Into a 8-mL vial, was placed methyl 4-(4-[[2-(4-chlorophenyl)-4,4-dimethylcyclohex-1-en-1-yl]methyl]piperazin-1-yl)-2-(4-[[2-(trimethylsilyl)ethoxy]methyl](11,11,12,12-2H4)-13-oxa-2,4,10-triazatricyclo[7.4.0.0^[3,7]]trideca-1(9), (20 mg, 0.03 mmol, 1 equiv), THF (2 mL), TBAF (100 mg, 0.38 mmol, 14.54 equiv), ethane-1,2-diamine (1 mL, 0.02 mmol, 0.63 equiv). The resulting solution was stirred for overnight at 70° C. The resulting mixture was concentrated under vacuum. The residue was applied onto a silica gel column with ethyl acetate/petroleum ether (0:1-1:1). This resulted in 12 mg (72.40%) of methyl 4-(4-[[2-(4-chlorophenyl)-4,4-dimethylcyclohex-1-en-1-yl]methyl]piperazin-1-yl)-2-[(11,11,12,12-2H4)-13-oxa-2,4,10-triazatricyclo[7.4.0.0^[3,7]]trideca-1(9),2,5,7-tetraen-10-yl]benzoate as a yellow solid. LC-MS-PH-PHNW-4-34-4: (ES, m/z): M+1=630. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min.

Synthesis of 4-(4-[[2-(4-chlorophenyl)-4,4-dimethylcyclohex-1-en-1-yl]methyl]piperazin-1-yl)-2-[(11,11,12,12-2H4)-13-oxa-2,4,10-triazatricyclo[7.4.0.0^[3,7]]trideca-1(9),2,5,7-tetraen-10-yl]benzoic acid: Into a 8-mL vial, was placed methyl 4-(4-[[2-(4-chlorophenyl)-4,4-dimethylcyclohex-1-en-1-yl]methyl]piperazin-1-yl)-2-[(11,11,12,12-2H4)-13-oxa-2,4,10-triazatricyclo[7.4.0.0^[3,7]]trideca-1(9),2,5,7-tetraen-10-yl]benzoate (12 mg, 0.02 mmol, 1 equiv), MeOH (1 mL), H$_2$O (1 mL), THF (1 mL), NaOH (3.0 mg, 0.08 mmol, 3.94 equiv). The resulting solution was stirred for overnight at 60° C. in an oil bath. The pH value of the solution was adjusted to 5 with HCl (1 mol/L). The reaction mixture was concentrated under vacuum. The residue was applied on a silica gel column and eluted with PE/EA (1:0-2:3). This resulted in 9 mg (76.71%) of 4-(4-[[2-(4-chlorophenyl)-4,4-dimethylcyclohex-1-en-1-yl] methyl]piperazin-1-yl)-2-[(11,11,12,12-2H4)-13-oxa-2,4,10-triazatricyclo[7.4.0.0^[3,7]]trideca-1(9),2,5,7-tetraen-10-yl]benzoic acid as an off-white solid. LC-MS-PH-PHNW-4-34-5: (ES, m/z): M+1=616. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min.

Synthesis of 4-(4-[[2-(4-chlorophenyl)-4,4-dimethylcyclohex-1-en-1-yl]methyl]piperazin-1-yl)-N-(4-[[(4-fluorooxan-4-yl)methyl]amino]-3-nitrobenzenesulfonyl)-2-[(11,11,12,12-2H4)-13-oxa-2,4,10-triazatricyclo[7.4.0.0.0ˆ[3,7]]trideca-1(9),2,5,7-tetraen-10-yl]benzamide: Into a 8-mL vial, was placed 4-(4-[[2-(4-chlorophenyl)-4,4-dimethylcyclohex-1-en-1-yl]methyl]piperazin-1-yl)-2-[(11,11,12,12-2H4)-13-oxa-2,4,10-triazatricyclo[7.4.0.0ˆ[3,7]]trideca-1,3(7),5,8-tetraen-10-yl]benzoic acid (9 mg, 0.01 mmol, 1 equiv), 4-[[(4-fluorooxan-4-yl)methyl]amino]-3-nitrobenzene-1-sulfonamide (6.3 mg, 0.02 mmol, 1.3 equiv), DCM (2 mL), DMAP (7.1 mg, 0.06 mmol, 3.98 equiv), EDCI (5.6 mg, 0.03 mmol, 2 equiv). The resulting solution was stirred for overnight at room temperature. The resulting mixture was concentrated under vacuum. The residue was applied onto a silica gel column with dichloromethane/methanol (10:1). This resulted in 6 mg (44.10%) of 4-(4-[[2-(4-chlorophenyl)-4,4-dimethylcyclohex-1-en-1-yl]methyl]piperazin-1-yl)-N-(4-[[(4-fluorooxan-4-yl)methyl]amino]-3-nitrobenzenesulfonyl)-2-[(11,11,12,12-2H4)-13-oxa-2,4,10-triazatricyclo[7.4.0.0.0ˆ[3,7]]trideca-1(9),2,5,7-tetraen-10-yl]benzamide as a yellow solid. LC-MS-PH-PHNW-4-34-0: (ES, m/z): M+1=931. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min. H-NMR-PH-PHNW-4-34-0: (d-DMSO, 300 ppm): 8.57 (s, 1H), 8.37 (s, 1H), 7.58-7.55 (m, 1H), 7.37-7.35 (m, 3H), 7.08-7.05 (m, 3H), 6.87-6.76 (m, 3H), 3.76-3.73 (m, 6H), 3.57-3.53 (m, 6H), 3.33 (m, 3H), 2.76-2.73 (m, 2H), 2.26-2.20 (m, 6H), 1.98 (m, 2H), 1.81-1.76 (m, 5H), 1.41-1.39 (m, 5H), 1.39 (m, 4H), 0.91-0.88 (m, 6H).

Example 5: Preparation of 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(2-methyl-2,3-dihydropyrrolo[3',2':5,6]pyrido[2,3-b][1,4]oxazin-1(6H)-yl)benzamide Synthesis of tert-butyl 1-(5-bromo-14(2-(trimethylsilyl)ethoxy)methyl)-1H-pyrrolo[2,3-b]pyridin-6-yloxy)propan-2-ylcarbamate. Into a 250 mL round-bottom flask was placed tert-butyl 1-hydroxypropan-2-ylcarbamate (2.28 g, 13.05 mmol, 1.50 equiv), DMF (30 mL), NaH (0.87 g, 21.75 mmol, 2.50 equiv) at 0° C. for 10 min. 5-bromo-6-fluoro-1-((2-(trimethylsilyl)ethoxy)methyl)-1H-pyrrolo[2,3-b]pyridine (3.0 g, 8.70 mmol, 1.00 equiv) was added. The resulting solution was stirred overnight at room temperature. The resulting solution was diluted with 200 mL of H$_2$O. The resulting solution was extracted with 3×300 mL of ethyl acetate and the organic layers combined. The resulting mixture was washed with 1×200 mL of H$_2$O and 1×200 mL sodium chloride(aq). The resulting mixture was concentrated under vacuum. The residue was applied onto a silica gel column with PE/EA (5:1). This resulted in 2.2g (50%) of tert-butyl 1-(5-bromo-1-((2-(trimethylsilyl)ethoxy)methyl)-1H-pyrrolo[2,3-b]pyridin-6-yloxy)propan-2-ylcarbamate as a yellow oil. LC-MS-PH-PHNW-4-35-1(ES, m/z): LC-MS (M+1): 502; RT=1.50 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 2.0 minutes; Oven temperature 40° C.; flow: 1.5 mL/min.

Synthesis of tert-butyl 2-methyl-64(2-(trimethylsilyl)ethoxy)methyl)-2,3-dihydropyrrolo[3',2':5,6]pyrido[2,3-b][1,4]oxazine-1(6H)-carboxylate. Into a 100 mL round-bottom flask was placed tert-butyl 1-(5-bromo-14(2-(trimethylsilyl)ethoxy)methyl)-1H-pyrrolo[2,3-b]pyridin-6-yloxy)propan-2-ylcarbamate (2.2 g, 4.39 mmol, 1.00 equiv), dioxane (25 mL), Cs$_2$CO$_3$ (4.30 g, 13.17 mmol, 3.00 equiv), X-phosPd 3G (1.04 g, 1.317 mmol, 0.30 equiv). The resulting solution was stirred overnight at 100° C. under N$_2$. The resulting mixture was concentrated under vacuum. The residue was applied onto a silica gel column with PE/EA (3:1). This resulted in 1.26 g (68%) of tert-butyl 2-methyl-64(2-(trimethylsilyl)ethoxy)methyl)-2,3-dihydropyrrolo[3',2':5,6]pyrido[2,3-b][1,4]oxazine-1(6H)-carboxylate as a yellow oil. LC-MS-PH-PHNW-4-35-2(ES, m/z): LC-MS (M+1): 420; RT=1.84 min. The measurements of the retention were done with a reversed phase column (C18). Shimadzu LCMS 2020; 50*3.0 Kinetex 2.6u XB-ODS, 2.6 microm; Eluent A: water (0.05% TFA); Eluent B: Acetonitrile; linear gradient from 5% acetonitrile to 100% acetonitrile in 2.6 minutes; Oven temperature 40° C.; flow: 1.0 mL/min.

Synthesis of 2-methyl-64(2-(trimethylsilyl)ethoxy)methyl)-1,2,3,6-tetrahydropyrrolo[3',2':5,6]pyrido[2,3-b][1,4]oxazine: Into a 250 mL round-bottom flask was placed tert-butyl 2-methyl-6-((2-(trimethylsilyl)ethoxyl)methyl)-2,3-dihydropyrrolo[3',2':5,6]pyrido[2,3-b][1,4]oxazine-1(6H)-carboxylate (1.26 g, 3.00 mmol, 1.00 equiv), DCM (15 mL), ZnBr$_2$ (10.0 g, 30 mmol, 10.0 equiv). The resulting solution was stirred at room temperature for 3 h. The resulting solution was diluted with 50 mL of NaHCO$_3$. The resulting solution was extracted with 3×50 mL of DCM and the organic layers combined. The resulting mixture was washed with 1×50 mL of H$_2$O and 1×50 mL sodium chloride(aq). The resulting mixture was concentrated under vacuum. The residue was applied onto a silica gel column with PE/EA (1:1). This resulted in 800 mg (83%) of 2-methyl-64(2-(trimethylsilyl)ethoxy)methyl)-1,2,3,6-tetrahydropyrrolo[3',2':5,6]pyrido[2,3-b][1,4]oxazine as a yellow oil. LC-MS-PH-PHNW-4-35-3(ES, m/z): LC-MS (M+1): 320; RT=1.54 min. The measurements of the retention were done with a reversed phase column (C18). Shimadzu LCMS 2020; 50*3.0 Kinetex 2.6u XB-ODS, 2.6 microm; Eluent A: water (0.05% TFA); Eluent B: Acetonitrile; linear gradient from 5% acetonitrile to 100% acetonitrile in 2.6 minutes; Oven temperature 40° C.; flow: 1.0 mL/min.

Synthesis of methyl 4-(4-((4'-chloro-5,5-dimethyl-3,4,5,6-tetrahydro-[1,1'-biphenyl]-2-yl)methyl) piperazin-1-yl)-2-(2-methyl-6-((2-(trimethylsilyl)ethoxy)methyl)-2,3-dihydropyrrolo[3',2':5,6]pyrido[2,3-b][1,4]oxazin-1(6H)-yl)benzoate: Into a 100 mL round-bottom flask was placed tert-butyl 1-(5-bromo-14(2-(trimethylsilyl)ethoxy)methyl)-1H-pyrrolo[2,3-b]pyridin-6-yloxy)propan-2-ylcarbamate (300 mg, 0.94 mmol, 1.00 equiv), dioxane (15 mL), Cs$_2$CO$_3$ (920 mg, 2.82 mmol, 3.00 equiv), XantphosPd 2G (83 mg, 0.094 mmol, 0.10 equiv), methyl 2-bromo-4-(4-((4'-chloro-5,5-dimethyl-3,4,5,6-tetrahydro-[1,1'-biphenyl]-2-yl) methyl)piperazin-1-yl)benzoate (1.0 g, 1.88 mmol, 2.00 equiv). The resulting solution was stirred overnight at 110°

C. under N₂. The resulting mixture was concentrated under vacuum. The residue was applied onto a silica gel column with PE/EA (5:1). This resulted in 360 mg (50%) of methyl 4-(4-((4'-chloro-5,5-dimethyl-3,4,5,6-tetrahydro-[1,1'-biphenyl]-2-yl)methyl)piperazin-1-yl)-2-(2-methyl-6-((2-(trimethylsilyl)ethoxy)methyl)-2,3-dihydropyrrolo[3',2':5,6]pyrido[2,3-b][1,4]oxazin-1(6H)-yl)benzoate as a yellow oil. LC-MS-PH-PHNW-4-35-4(ES, m/z): LC-MS (M+1): 770; RT=1.56 min. The measurements of the retention were done with a reversed phase column (C18). Shimadzu LCMS 2020; 50*3.0 Kinetex 2.6u XB-ODS, 2.6 microm; Eluent A: water (0.05% TFA); Eluent B: Acetonitrile; linear gradient from 5% acetonitrile to 100% acetonitrile in 2.6 minutes; Oven temperature 40° C.; flow: 1.0 mL/min Synthesis of methyl 4-(4-((4'-chloro-5,5-dimethyl-3,4,5,6-tetrahydro-[1,1'-biphenyl]-2-yl)methyl) piperazin-1-yl)-2-(2-methyl-2,3-dihydropyrrolo[3',2':5,6]pyrido[2,3-b][1,4]oxazin-1(6H)-yl) benzoate Into a 100 mL round-bottom flask was placed tert-butyl methyl 4-(4-((4'-chloro-5,5-dimethyl-3,4,5,6-tetrahydro-[1,1'-biphenyl]-2-yl)methyl)piperazin-1-yl)-2-(2-methyl-6-((2-(trimethylsilyl)ethoxy)methyl)-2,3-dihydropyrrolo[3',2':5,6]pyrido[2,3-b][1,4]oxazin-1(6H)-yl)benzoate (300 mg, 0.39 mmol, 1.00 equiv), THF (10 mL), TBAF (3.0 g), ethane-1,2-diamine (5 mL). The resulting solution was stirred overnight at 60° C. The resulting mixture was concentrated under vacuum. The mixture was adjust PH<7 by 2N HCl. The resulting solution was extracted with 3×200 mL of EA and the organic layers combined. The resulting mixture was washed with 1×10 mL of H₂O and 1×10 mL sodium chloride(aq). The resulting mixture was concentrated under vacuum. This resulted in 120 mg (48%) of methyl 4-(4-((4'-chloro-5,5-dimethyl-3,4,5,6-tetrahydro-[1,1'-biphenyl]-2-yl)methyl)piperazin-1-yl)-2-(2-methyl-2,3-dihydropyrrolo[3',2':5,6]pyrido[2,3-b][1,4]oxazin-1(6H)-yl)benzoate as a yellow oil. LC-MS-PH-PHNW-4-35-5(ES, m/z): LC-MS (M+1): 640; RT=2.82 min. The measurements of the retention were done with a reversed phase column (C18). Shimadzu LCMS 2020; 50*3.0 Kinetex 2.6u HPH-C18, 2.6 microm; Eluent A: water (0.05% NH₄HCO₃); Eluent B: Methanol; linear gradient from 10% acetonitrile to 98% acetonitrile in 3.5 minutes; Oven temperature 40° C.; flow: 0.8 mL/min.

Synthesis of 4-(4-((4'-chloro-5,5-dimethyl-3,4,5,6-tetrahydro-[1,1'-biphenyl]-2-yl)methyl)piperazin-1-yl)-2-(2-methyl-2,3-dihydropyrrolo[3',2':5,6]pyrido[2,3-b][1,4]oxazin-1(6H)-yl)benzoic acid. Into a 50 mL round-bottom flask was methyl 4-(4-((4'-chloro-5,5-dimethyl-3,4,5,6-tetrahydro-[1,1'-biphenyl]-2-yl)methyl)piperazin-1-yl)-2-(2-methyl-2,3-dihydropyrrolo[3',2':5,6]pyrido[2,3-b][1,4]oxazin-1(6H)-yl)benzoate (70 mg, 0.11 mmol, 1.00 equiv), MeOH/H₂O (5/5 mL), NaOH (44 mg, 1.10 mmol, 10 equiv). The resulting solution was stirred at 60° C. for 3h. The resulting mixture was concentrated under vacuum. The residue was applied onto a silica gel column with dichloromethane/methanol (10:1). This resulted in 50 mg (73%) of 4-(4-((4'-chloro-5,5-dimethyl-3,4,5,6-tetrahydro-[1,1'-biphenyl]-2-yl)methyl)piperazin-1-yl)-2-(2-methyl-2,3-dihydropyrrolo[3',2':5,6]pyrido[2,3-b][1,4]oxazin-1(6H)-yl)benzoic acid as a white solid. LC-MS-PH-PHNW-4-35-6(ES, m/z): LC-MS (M+1): 626; RT=2.45 min. The measurements of the retention were done with a reversed phase column (C18). Shimadzu LCMS 2020; 50*3.0 Kinetex 2.6u HPH-C18, 2.6 microm; Eluent A: water (0.05% NH₄HCO₃); Eluent B: Methanol; linear gradient from 10% acetonitrile to 98% acetonitrile in 3.5 minutes; Oven temperature 40° C.; flow: 0.8 mL/min.

Synthesis of 4-(4-((4'-chloro-5,5-dimethyl-3,4,5,6-tetrahydro-[1,1'-biphenyl]-2-yl) methyl)piperazin-1-yl)-N-((4-(((4-fluorotetrahydro-2H-pyran-4-yl)methyl)amino)-3-nitrophenyl)sulfonyl)-2-(2-methyl-2,3-dihydropyrrolo[3',2':5,6]pyrido[2,3-b][1,4]oxazin-1(6H)-yl)benzamide: Into a 50-mL 1-necked round-bottom flask was placed 4-(4-((4'-chloro-5,5-dimethyl-3,4,5,6-tetrahydro-[1,1'-biphenyl]-2-yl)methyl)piperazin-1-yl)-2-(2-methyl-2,3-dihydropyrrolo[3',2':5,6]pyrido[2,3-b][1,4]oxazin-1(6H)-yl)benzoic acid (40 mg, 0.064 mol, 1.00 equiv), DCM (4 mL), EDCI (49 mg, 0.256 mmol, 4.00 equiv), DMAP (16 mg, 0.128 mmol, 2.00 equiv), 4-(((4-fluorotetrahydro-2H-pyran-4-yl)methyl)amino)-3-nitrobenzenesulfonamide (28 mg, 0.0832 mol, 1.30 equiv). The resulting solution was stirred overnight at 40° C. The resulting mixture was concentrated under vacuum. This resulted in 2.9 mg (70%) of 4-(4-((4'-chloro-5,5-dimethyl-3,4,5,6-tetrahydro-[1,1'-biphenyl]-2-yl) methyl)piperazin-1-yl)-N-((4-(((4-fluorotetrahydro-2H-pyran-4-yl)methyl)amino)-3-nitrophenyl)sulfonyl)-2-(2-methyl-2,3-dihydropyrrolo[3',2':5,6]pyrido[2,3-b][1,4]oxazin-1(6H)-yl)benzamide as a yellow solid. LC-MS-PH-PHNW-4-35-0A (ES, m/z): LC-MS (M+1):941; RT=5.02 min. The measurements of the retention were done with a reversed phase column (C18). Shimadzu LCMS 2020; 50*3.0 Kinetex 2.6u Ascentis Express C18, 2.6 microm; Eluent A: water (0.05% TFA); Eluent B: Methanol; linear gradient from 5% acetonitrile to 95% acetonitrile in 7.0 minutes; Oven temperature 40° C.; flow: 1.0 mL/min.

Example 6: Preparation of (S)-4-(4-((4'-chloro-5,5-dimethyl-3,4,5,6-tetrahydro-[1,1'-biphenyl]-2-yl) methyl)piperazin-1-yl)-N-((4-(((4-fluorotetrahydro-2H-pyran-4-yl)methyl)amino)-3-nitrophenyl) sulfonyl)-2-(3-methyl-2,3-dihydropyrrolo[3',2':5,6] pyrido[2,3-b][1,4]oxazin-1(6H)-yl)benzamide and (R)-4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(3-methyl-2,3-dihydropyrrolo[3',2':5,6]pyrido[2,3-b][1,4]oxazin-1(6H)-yl)benzamide Synthesis of 12-methyl-4-[[2-(trimethylsilyl)ethoxy]methyl]-13-oxa-2,4,10-triazatricyclo[7.4.0.0ˆ[3,7]]trideca-1(9),2,5,7-tetraen-11-one: Into a 100-mL round-bottom flask, was placed 5-amino-1-[[2-(trimethylsilyl)ethoxy]methyl]-1H-pyrrolo[2,3-b]pyridin-6-ol (1.5 g, 5.37 mmol, 1 equiv), DMF (50 mL), K₂CO₃ (2.2 g, 16.11 mmol, 3 equiv). This was followed by the addition of 2-chloropropanoyl chloride (1.4 g, 10.74 mmol, 2 equiv) dropwise with stirring at 0° C. The resulting solution was stirred for overnight at room temperature. The reaction was then quenched by the addition of 50 mL of water. The resulting solution was extracted with 2×50 mL of ethyl acetate. The resulting mixture was washed with 2×50 mL of brine. The mixture was dried over anhydrous sodium sulfate and filtrate and concentrated under vacuum. The residue was applied onto a silica gel column with ethyl acetate/petroleum ether (0:1-1:3). This resulted in 500 mg (27.93%) of 12-methyl-4-[[2-(trimethylsilyl)ethoxy]methyl]-13-oxa-2,4,10-triazatricyclo[7.4.0.0ˆ[3,7]]trideca-1(9),2,5,7-tetraen-11-one as a yellow solid. LC-MS-PH-PHNW-4-37-1: (ES, m/z): M+1=334, R,T=1.123 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min. H-NMR-PH-PHNW-4-37-1: (CDCl3, 300 ppm): 8.34 (s, 1H), 7.63 (d, J=3 Hz, 1H), 7.42-7.28 (m, 1H), 6.46 (d, J=3 Hz, 1H), 5.68 (s, 2H), 4.92-4.85 (m, 1H), 3.63-3.53 (m, 2H), 1.85-1.81 (d, J=12 Hz, 3H), 0.94-0.89 (m, 2H), −0.154 (s, 9H). The measurements of the NMR spectra were done with BrukerAvanceIII HD 300 MHz with a probe head of BBOF.

Synthesis of 12-methyl-4-[[2-(trimethylsilyl)ethoxy]methyl]-13-oxa-2,4,10-triazatricyclo[7.4.0.0ˆ[3,7]]trideca-1(9),2,5,7-tetraene & (12R or S)-12-methyl-4-[[2-(trimethylsilyl)ethoxy]methyl]-13-oxa-2,4,10-triazatricyclo[7.4.0.0ˆ[3,7]]trideca-1(9),2,5,7-tetraene(Assumed) & (12S or R)-12-methyl-4-[[2-(trimethylsilyl)ethoxy]methyl]-13-oxa-2,4,10-triazatricyclo[7.4.0.0ˆ[3,7]]trideca-1(9),2,5,7-tetraene(Assumed): Into a 100-mL 3-necked round-bottom flask, was placed 12-methyl-4-[[2-(trimethylsilyl)ethoxy]methyl]-13-oxa-2,4,10-triazatricyclo[7.4.0.0ˆ[3,7]]trideca-1(9),2,5,7-tetraen-11-one (500 mg, 1.50 mmol, 1 equiv), THF (20 mL). This was followed by the addition of LiAlH$_4$ (113.8 mg, 3.00 mmol, 2 equiv), in portions at 0° C. The resulting solution was stirred for 1 overnight at room temperature. The reaction was then quenched by the addition of 20 mL of water. The solids were filtered out. The resulting solution was extracted with 2×20 mL of ethyl acetate. The resulting mixture was washed with 2×20 mL of brine. The mixture was dried over anhydrous sodium sulfate and filtrate and concentrated under vacuum. The residue was applied onto a silica gel column with ethyl acetate/petroleum ether (0:1-1:3). This resulted in 450 mg (93%) of 12-methyl-4-[[2-(trimethylsilyl)ethoxy]methyl]-13-oxa-2,4,10-triazatricyclo[7.4.0.0ˆ[3,7]]trideca-1(9),2,5,7-tetraene as a yellow solid.

The crude 12-methyl-4-[[2-(trimethylsilyl)ethoxy]methyl]-13-oxa-2,4,10-triazatricyclo[7.4.0.0ˆ[3,7]]trideca-1(9),2,5,7-tetraene (450 mg) was purified by Chiral-Prep-HPLC with the following conditions: (SHIMADZU LC-20AT): Column, CHIRALPAK IC; mobile phase A:n-hexane, Phase B:ethanol; Detector, 220 nm. This resulted in 200 mg (44%) of (12R or S)-12-methyl-4-[[2-(trimethylsilyl)ethoxy]methyl]-13-oxa-2,4,10-triazatricyclo[7.4.0.0ˆ[3,7]]trideca-1(9),2,5,7-tetraene as a yellow solid (Assumed).

This resulted in 200 mg (44%) of (12S or R)-12-methyl-4-[[2-(trimethylsilyl)ethoxy]methyl]-13-oxa-2,4,10-triazatricyclo[7.4.0.0ˆ[3,7]]trideca-1(9),2,5,7-tetraene as a yellow solid (Assumed).

LC-MS-PH-PHNW-4-37-2: (ES, m/z): M+1=320, R,T=1.107 min.

The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min.

H-NMR-PH-PHNW-4-37-2: (CDCl3, 300 ppm): 7.63 (s, 1H), 7.17 (s, 1H), 6.36-6.35 (d, J=3 Hz, 1H), 5.57-5.52 (m, 2H), 4.59-4.55 (m, 1H), 3.62-3.46 (m, 3H), 3.18-3.14 (m, 1H), 1.62-1.44 (m, 3H), 0.93-0.88 (m, 2H), −0.17 (s, 9H).

Synthesis of methyl 4-(4-[[2-(4-chlorophenyl)-4,4-dimethylcyclohex-1-en-1-yl]methyl]piperazin-1-yl)-2-[(12R or S)-12-methyl-4-[[2-(trimethylsilyl)ethoxy]methyl]-13-oxa-2,4,10-triazatricyclo[7.4.0.0ˆ[3,7]]trideca-1(9),2,4,10-triazatricyclo[7.4.0.0ˆ3,7]trideca-1(9),2,5,7-tetraen-10-yl]benzoate (Assumed): Into a 8-mL vial, was placed (12R)-12-methyl-4-[[2-(trimethylsilyl)ethoxy]methyl]-13-oxa-2,4,10-triazatricyclo[7.4.0.0ˆ[3,7]]trideca-1(9),2,5,7-tetraene (200 mg, 0.63 mmol, 1 equiv), methyl 2-bromo-4-(4-[[2-(4-chlorophenyl)-4,4-dimethylcyclohex-1-en-1-yl]methyl]piperazin-1-yl)benzoate (399.6 mg, 0.75 mmol, 1.2 equiv), Cs$_2$CO$_3$ (611.9 mg, 1.88 mmol, 3 equiv), Dioxane (5 mL), Chloro[9,9-dimethyl-4,5-bis(diphenylphosphino)xanthene][2-amino-1,1-biphenyl-2-yl]palladium(II) (120 mg). The resulting solution was stirred for 2 hr at 110° C. in an oil bath. The resulting mixture was concentrated under vacuum. The residue was applied onto a silica gel column with ethyl acetate/petroleum ether (0:1-1:10). This resulted in 250 mg (51.83%) of methyl 4-(4-[[2-(4-chlorophenyl)-4,4-dimethylcyclohex-1-en-1-yl]methyl]piperazin-1-yl)-2-[(12R or S)-12-methyl-4-[[2-(trimethylsilyl)ethoxy]methyl]-13-oxa-2,4,10-triazatricyclo[7.4.0.0ˆ[3,7]]trideca-1(9),2,4,10-triazatricyclo[7.4.0.0ˆ3,7]trideca-1(9),2,5,7-tetraen-10-yl]benzoate as a yellow solid (Assumed).

Synthesis of methyl 4-(4-[[2-(4-chlorophenyl)-4,4-dimethylcyclohex-1-en-1-yl]methyl]piperazin-1-yl)-2-[(12R or S)-12-methyl-13-oxa-2,4,10-triazatricyclo[7.4.0.0ˆ[3,7]]trideca-1(9),2,5,7-tetraen-10-yl]benzoate (Assumed) Into a 100-mL round-bottom flask, was placed methyl 4-(4-[[2-(4-chlorophenyl)-4,4-dimethylcyclohex-1-en-1-yl]methyl]piperazin-1-yl)-2-[(12R or S)-12-methyl-4-[[2-(trimethylsilyl)ethoxy]methyl]-13-oxa-2,4,10-triazatricyclo[7.4.0.0ˆ3,7]]trideca-1(9),2 (250 mg, 0.32 mmol, 1 equiv), TBAF (3 g, 11.47 mmol, 35.36 equiv), THF (30 mL), ethane-1,2-diamine (2 g, 33.28 mmol, 102.56 equiv). The resulting solution was stirred for 12 h at 70° C. in an oil bath. The reaction was then quenched by the addition of 50 mL of water. The resulting solution was extracted with 2×50 mL of ethyl acetate. The resulting mixture was washed with 3×50 mL of brine. The mixture was dried over anhydrous sodium sulfate and filtrate and concentrated under vacuum. The residue was applied onto a silica gel column with ethyl acetate/petroleum ether (0:1-1:3). This resulted in 90 mg (43%) of methyl 4-(4-[[2-(4-chlorophenyl)-4,4-dimethylcyclohex-1-en-1-yl]methyl]piperazin-1-yl)-2-[(12R or S)-12-methyl-13-oxa-2,4,10-triazatricyclo[7.4.0.0ˆ[3,7]]trideca-1(9),2,5,7-tetraen-10-yl]benzoate as a yellow solid (Assumed). H-NMR-PH-PHNW-4-37-50: (CDCl3, 300 ppm): 8.24 (s, 1H), 7.89-7.86 (d, J=9 Hz, 1H), 7.32-7.24 (m, 6H), 7.14-7.01 (m, 1H), 6.97-6.94 (m, 2H), 6.73-6.65 (m, 2H), 6.18 (s, 1H), 3.67-3.53 (m, 3H), 3.32-3.18 (m, 3H), 2.98-2.80 (m, 1H), 2.30-2.04 (m, 6H), 1.99 (s, 2H), 1.56-1.50 (m, 5H), 0.91-0.88 (m, 6H).

Synthesis of 4-(4-[[2-(4-chlorophenyl)-4,4-dimethylcyclohex-1-en-1-yl]methyl]piperazin-1-yl)-2-[(12R or S)-12-methyl-13-oxa-2,4,10-triazatricyclo[7.4.0.0ˆ[3,7]]trideca-1(9),2,5,7-tetraen-10-yl]benzoic acid(Assumed). Into a 8-mL vial, was placed methyl 4-(4-[[2-(4-chlorophenyl)-4,4-dimethylcyclohex-1-en-1-yl]methyl]piperazin-1-yl)-2-[(12R or S)-12-methyl-13-oxa-2,4,10-triazatricyclo[7.4.0.0ˆ[3,7]]trideca-1(9),2,5,7-tetraen-10-yl]benzoate (90 mg, 0.14 mmol, 1 equiv), MeOH (1 mL), H$_2$O (1 mL), THF (1 mL), NaOH (22.5 mg, 0.56 mmol, 4 equiv). The resulting solution was stirred for overnight at 60° C. in an oil bath. The pH value of the solution was adjusted to 5 with HCl (1 mol/L). The resulting mixture was concentrated under vacuum. The residue was applied onto a silica gel column with dichloromethane/methanol (1:0-10:1). This resulted in 80 mg (90%) of 4-(4-[[2-(4-chlorophenyl)-4,4-dimethylcyclohex-1-en-1-yl]methyl]piperazin-1-yl)-2-[(12R or S)-12-methyl-13-oxa-2,4,10-triazatricyclo[7.4.0.0ˆ[3,7]]trideca-1(9),2,5,7-tetraen-10-yl]benzoic acid as a yellow solid (Assumed). LC-MS-PH-PHNW-4-37-60: (ES, m/z): M+1=626, R,T=1.035 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min.

Synthesis of 4-(4-[[2-(4-chlorophenyl)-4,4-dimethylcyclohex-1-en-1-yl]methyl]piperazin-1-yl)-N-(4-[[(4-fluorooxan-4-yl)methyl]amino]-3-nitrobenzenesulfonyl)-2-[(12R or S)-12-methyl-13-oxa-2,4,10-triazatricyclo[7.4.0.0ˆ[3,7]]trideca-1(9),2,5,7-tetraen-10-yl]benzamide (Assumed): Into a 8-mL vial, was placed 4-(4-[[2-(4-chlorophenyl)-4,4-dimethylcyclohex-1-en-1-yl]methyl]piperazin-1-yl)-2-[(12R or S)-12-methyl-13-oxa-2,4,10-triazatricyclo[7.4.0.0ˆ[3,7]]trideca-1(9),2,5,7-tetraen-10-yl]benzoic acid (90 mg, 0.14 mmol, 1 equiv), 4-[[(4-fluorooxan-4-yl)methyl]amino]-3-nitrobenzene-1-sulfonamide (57.5 mg, 0.17 mmol, 1.2 equiv), DCM (5 mL), DMAP (70.2 mg, 0.57 mmol, 4 equiv), EDCI (55.1 mg, 0.29 mmol, 2.00 equiv). The resulting solution was stirred for overnight at room temperature. The resulting mixture was concentrated. The crude product was purified by Flash-Prep-HPLC with the following conditions (IntelFlash-1): Column, C18 silica gel; mobile phase, Water (0.1% FA) and ACN (48.0% ACN up to 53.0% in 7 min, hold 95.0% in 1 min, down to 48.0% in 1 min, hold 48.0% in 1 min) within 5 min; Detector, UV 254 nm. This resulted in 28 mg (20%) of 4-(4-[[2-(4-chlorophenyl)-4,4-dimethylcyclohex-1-en-1-yl]methyl]piperazin-1-yl)-N-(4-[[(4-fluorooxan-4-yl)methyl]amino]-3-nitrobenzenesulfonyl)-2-[(12R or S)-12-methyl-13-oxa-2,4,10-triazatricyclo[7.4.0.0ˆ[3,7]]trideca-1(9),2,5,7-tetraen-10-yl]benzamide as a yellow solid (Assumed). 19.8 mg product was submitted (Assumed). LC-MS-PH-PHNW-4-37-0: (ES, m/z): M+1=941, R,T=3.04 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min. H-NMR-PH-PHNW-4-37-0: (d-DMSO, 300 ppm): 8.59 (s, 1H), 8.54 (s, 1H), 7.55-7.53 (m, 1H), 7.36-7.29 (d, J=6 Hz, 3H), 7.12-7.06 (m, 3H), 6.80-6.72 (m, 3H), 5.95 (m, 1H), 4.53-4.51 (m, 1H), 3.78-3.43 (m, 7H), 3.21-3.00 (m, 5H), 2.22-2.17 (m, 5H), 1.96-1.75 (m, 6H), 1.58-1.56 (m, 5H), 0.93-0.88 (m, 6H).

Synthesis of methyl 4-(4-[[2-(4-chlorophenyl)-4,4-dimethylcyclohex-1-en-1-yl]methyl]piperazin-1-yl)-2-[(12S or R)-12-methyl-4-[[2-(trimethylsilyl)ethoxy]methyl]-13-oxa-2,4,10-triazatricyclo[7.4.0.0ˆ[3,7]]trideca-1(9),2,2,5,7-tetraen-10-yl]benzoate (Assumed): Into a 8-mL vial, was placed (12S or R)-12-methyl-4-[[2-(trimethylsilyl)ethoxy]methyl]-13-oxa-2,4,10-triazatricyclo[7.4.0.0ˆ[3,7]]trideca-1(9),2,5,7-tetraene (200 mg, 0.63 mmol, 1 equiv), methyl 2-bromo-4-(4-[[2-(4-chlorophenyl)-4,4-dimethylcyclohex-1-en-1-yl]methyl]piperazin-1-yl)benzoate (399.6 mg, 0.75 mmol, 1.2 equiv), $Cs_2CO_3$ (611.9 mg, 1.88 mmol, 3 equiv), Dioxane (5 mL), Chloro[9,9-dimethyl-4,5-bis(diphenylphosphino)xanthene][2-amino-1,1-biphenyl-2-yl]palladium(II) (120 mg). The resulting solution was stirred for 2 h at 110° C. in an oil bath. The resulting mixture was concentrated under vacuum. The residue was applied onto a silica gel column with ethyl acetate/petroleum ether (0:1-1:10). This resulted in 250 mg (51%) of methyl 4-(4-[[2-(4-chlorophenyl)-4,4-dimethylcyclohex-1-en-1-yl]methyl]piperazin-1-yl)-2-[(12S or R)-12-methyl-4-[[2-(trimethylsilyl)ethoxy]methyl]-13-oxa-2,4,10-triazatricyclo[7.4.0.0ˆ[3,7]]trideca-1(9),2,2,5,7-tetraen-10-yl]benzoate as a yellow solid (Assumed).

Synthesis of methyl 4-(4-[[2-(4-chlorophenyl)-4,4-dimethylcyclohex-1-en-1-yl]methyl]piperazin-1-yl)-2-[(12S or R)-12-methyl-13-oxa-2,4,10-triazatricyclo[7.4.0.0ˆ[3,7]]trideca-1(9),2,5,7-tetraen-10-yl]benzoate (Assumed): into a 100-mL round-bottom flask, was placed methyl 4-(4-[[2-(4-chlorophenyl)-4,4-dimethylcyclohex-1-en-1-yl]methyl]piperazin-1-yl)-2-[(12S or R)-12-methyl-4-[[2-(trimethylsilyl)ethoxy]methyl]-13-oxa-2,4,10-triazatricyclo[7.4.0.0ˆ[3,7]]trideca-1(9),2 (250 mg, 0.32 mmol, 1 equiv), TBAF (3 g, 11.47 mmol, 35.36 equiv), THF (30 mL), ethane-1,2-diamine (2 g, 33.28 mmol, 102.56 equiv). The resulting solution was stirred for 12 h at 70° C. in an oil bath. The reaction was then quenched by the addition of 50 mL of water. The resulting solution was extracted with 2×50 mL of ethyl acetate. The resulting mixture was washed with 3×50 mL of brine. The mixture was dried over anhydrous sodium sulfate and filtrate and concentrated under vacuum. The residue was applied onto a silica gel column with ethyl acetate/petroleum ether (0:1-1:3). This resulted in 90 mg (43%) of methyl 4-(4-[[2-(4-chlorophenyl)-4,4-dimethylcyclohex-1-en-1-yl]methyl]piperazin-1-yl)-2-[(12S or R)-12-methyl-13-oxa-2,4,10-triazatricyclo[7.4.0.0ˆ[3,7]]trideca-1(9),2,5,7-tetraen-10-yl]benzoate as a yellow solid (Assumed).

LC-MS-PH-PHNW-4-38-50: (ES, m/z): M+1=640, R,T=1.424 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min. H-NMR-PH-PHNW-4-38-50: (CDCl3, 300 ppm): 8.24 (s, 1H), 7.89-7.86 (d, J=9 Hz, 1H), 7.32-7.24 (m, 6H), 7.14-7.01 (m, 1H), 6.97-6.94 (m, 2H), 6.73-6.65 (m, 2H), 6.18 (s, 1H), 3.67-3.53 (m, 3H), 3.32-3.18 (m, 3H), 2.98-2.80 (m, 1H), 2.30-2.04 (m, 6H), 1.99 (s, 2H), 1.56-1.50 (m, 5H), 0.91-0.88 (m, 6H).

Synthesis of 4-(4-[[2-(4-chlorophenyl)-4,4-dimethylcyclohex-1-en-1-yl]methyl]piperazin-1-yl)-2-[(12S or R)-12-methyl-13-oxa-2,4,10-triazatricyclo[7.4.0.0ˆ[3,7]]trideca-1(9),2,5,7-tetraen-10-yl]benzoic acid (Assumed): Into a 8-mL vial, was placed methyl 4-(4-[[2-(4-chlorophenyl)-4,4-dimethylcyclohex-1-en-1-yl]methyl]piperazin-1-yl)-2-[(12S or R)-12-methyl-13-oxa-2,4,10-triazatricyclo[7.4.0.0ˆ[3,7]]trideca-1(9),2,5,7-tetraen-10-yl]benzoate (90 mg, 0.14 mmol, 1 equiv), MeOH (1 mL), $H_2O$ (1 mL), THF (1 mL), NaOH (22.5 mg, 0.56 mmol, 4.00 equiv). The resulting solution was stirred for overnight at 60° C. in an oil bath. The pH value of the solution was adjusted to 5 with HCl (1 mol/L). The resulting mixture was concentrated under vacuum. The residue was applied onto a silica gel column with chloroform/methanol (1:0-10:1). This resulted in 80 mg (90%) of 4-(4-[[2-(4-chlorophenyl)-4,4-dimethylcyclohex-1-en-1-yl]methyl]piperazin-1-yl)-2-[(12S or R)-12-methyl-13-oxa-2,4,10-triazatricyclo[7.4.0.0ˆ[3,7]]trideca-1(9),2,5,7-tetraen-10-yl]benzoic acid as a solid (Assumed): LC-MS-PH-PHNW-4-38-60: (ES, m/z): M+1=626, R,T=1.039 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min.

Synthesis of 4-(4-[[2-(4-chlorophenyl)-4,4-dimethylcyclohex-1-en-1-yl]methyl]piperazin-1-yl)-N-(4-[[(4-fluorooxan-4-yl)methyl]amino]-3-nitrobenzenesulfonyl)-2-[(12S or R)-12-methyl-13-oxa-2,4,10-triazatricyclo[7.4.0.0ˆ[3,7]]trideca-1(9),2,5,7-tetraen-10-yl]benzamide (Assumed): Into a 8-mL vial, was placed 4-(4-[[2-(4-chlorophenyl)-4,4-dimethylcyclohex-1-en-1-yl]methyl]

piperazin-1-yl)-2-[(12S or R)-12-methyl-13-oxa-2,4,10-triazatricyclo[7.4.0.0ˆ[3,7]]trideca-1(9),2,5,7-tetraen-10-yl]benzoic acid (90 mg, 0.14 mmol, 1 equiv), 4-[[(4-fluorooxan-4-yl)methyl]amino]-3-nitrobenzene-1-sulfonamide (57.5 mg, 0.17 mmol, 1.2 equiv), DCM (5 mL), DMAP (70.2 mg, 0.57 mmol, 4 equiv), EDCI (55.1 mg, 0.29 mmol, 2 equiv). The resulting solution was stirred for overnight at room temperature. The resulting mixture was concentrated. The crude product was purified by Flash-Prep-HPLC with the following conditions (IntelFlash-1): Column, C18 silica gel; mobile phase, Water (0.1% FA) and ACN (48.0% ACN up to 53.0% in 7 min, hold 95.0% in 1 min, down to 48.0% in 1 min, hold 48.0% in 1 min) within 5 min; Detector, UV 254 nm. This resulted in 26 mg (19%) of 4-(4-[[2-(4-chlorophenyl)-4,4-dimethylcyclohex-1-en-1-yl]methyl]piperazin-1-yl)-N-(4-[[(4-fluorooxan-4-yl)methyl]amino]-3-nitrobenzenesulfonyl)-2-[(12S or R)-12-methyl-13-oxa-2,4,10-triazatricyclo[7.4.0.0ˆ[3,7]]trideca-1(9),2,5,7-tetraen-10-yl]benzamide as a yellow solid. 19.6 mg product was submitted(Assumed). LC-MS-PH-PHNW-4-38-0: (ES, m/z): M+1=941, R,T=3.036 min. The measurements of the retention were done with a reversed phase column (C18). Shimadzu LCMS 2020; 50*3.0 Kinetex 2.6u XB-C18, 2.6 microm; Eluent A: water (0.05 TFA); Eluent B: Acetonitrile; linear gradient from 5% acetonitrile to 100% acetonitrile in 3.5 minutes; Oven temperature 40° C.; flow: 1.5 mL/min. H-NMR-PH-PHNW-4-38-0: (d-DMSO, 300 ppm): 8.56 (s, 1H), 8.36 (s, 1H), 7.62-7.54 (m, 1H), 7.37-7.30 (m, 3H), 7.14-7.04 (m, 3H), 6.98-6.92 (m, 3H), 5.94 (m, 1H), 4.53 (m, 1H), 3.79-3.71 (m, 4H), 3.65-3.54 (m, 3H), 3.44 (m, 4H), 2.78-2.73 (m, 2H), 2.23-2.18 (m, 6H), 1.97-1.91 (m, 2H), 1.87-1.81 (m, 4H), 1.50-1.20 (m, 5H), 0.91-0.88 (m, 6H).

Example 7: Preparation of 4-(4-((4'-chloro-5,5-dimethyl-3,4,5,6-tetrahydro-[1,1'-biphenyl]-2-yl)methyl)piperazin-1-yl)-2-(3,3-dimethyl-2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide Synthesis of 12,12-dimethyl-4-[[2-(trimethylsilyl)ethoxy]methyl]-13-oxa-2,4,10-triazatricyclo[7.4.0.0ˆ[3,7]]trideca-1,3(7),5,8-tetraen-11-one: Into a 100-mL round-bottom flask, was placed 5-amino-1-[[2-(trimethylsilyl)ethoxy]methyl]-1H-pyrrolo[2,3-b]pyridin-6-ol (1 g, 3.58 mmol, 1 equiv), CH₃CN (20 mL), methyl 2-bromo-2-methylpropanoate (647.9 mg, 3.58 mmol, 1.0 equiv), Cs₂CO₃ (1.7 g, 5.37 mmol, 1.5 equiv). The resulting solution was stirred for 2 h at 80° C. in an oil bath. The resulting mixture was concentrated under vacuum. The residue was applied onto a silica gel column with ethyl acetate/petroleum ether (1:3). This resulted in 270 mg (21%) of 12,12-dimethyl-4-[[2-(trimethylsilyl)ethoxy]methyl]-13-oxa-2,4,10-triazatricyclo[7.4.0.0ˆ[3,7]]trideca-1,3(7),5,8-tetraen-11-one as a light yellow solid. LC-MS-PH-PHNW-4-40-2: (ES, m/z): M+1=348, R,T=1.164 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min.

Synthesis of 12,12-dimethyl-4-[[2-(trimethylsilyl)ethoxy]methyl]-13-oxa-2,4,10-triazatricyclo[7.4.0.0ˆ[3,7]]trideca-1,3(7),5,8-tetraene: Into a 8-mL vial, was placed 12,12-dimethyl-4-[[2-(trimethylsilyl)ethoxy]methyl]-13-oxa-2,4,10-triazatricyclo[7.4.0.0ˆ[3,7]]trideca-1,3(7),5,8-tetraen-11-one (250 mg, 0.72 mmol, 1 equiv), THF (3 mL). This was followed by the addition of LiAlH₄ (54.6 mg, 1.44 mmol, 2 equiv), in portions at 0° C. The resulting solution was stirred for overnight at room temperature. The reaction was then quenched by the addition of 5 mL of water. The solids were filtered out. The resulting solution was extracted with 2×10 mL of ethyl acetate. The organic layer was dried over anhydrous sodium sulfate and concentrated under vacuum. The residue was applied onto a silica gel column with ethyl acetate/petroleum ether (0:1-1:5). This resulted in 140 mg (58%) of 12,12-dimethyl-4-[[2-(trimethylsilyl)ethoxy]methyl]-13-oxa-2,4,10-triazatricyclo[7.4.0.0ˆ[3,7]]trideca-1,3(7),5,8-tetraene as a yellow solid.

Synthesis of 4-(4-[[2-(4-chlorophenyl)-4,4-dimethylcyclohex-1-en-1-yl]methyl]piperazin-1-yl)-2-(12,12-dimethyl-4-[[2-(trimethylsilyl)ethoxy]methyl]-13-oxa-2,4,10-triazatricyclo[7.4.0.0ˆ[3,7]]trideca-1,3(7), 5,8-tetraen-10-yl)benzoate: Into a 8-mL vial, was placed 12,12-dimethyl-4-[[2-(trimethylsilyl)ethoxy]methyl]-13-oxa-2,4,10-triazatricyclo[7.4.0.0ˆ[3,7]]trideca-1,3(7),5,8-tetraene (140 mg, 0.42 mmol, 1 equiv), methyl 2-bromo-4-(4-[[2-(4-chlorophenyl)-4,4-dimethylcyclohex-1-en-1-yl]methyl]piperazin-1-yl)benzoate (267.9 mg, 0.50 mmol, 1.2 equiv), Cs₂CO₃ (410.3 mg, 1.26 mmol, 3 equiv), Dioxane (2 mL), Chloro[9,9-dimethyl-4,5-bis(diphenylphosphino)xanthene][2-amino-1,1-biphenyl-2-yl]palladium(II) (80 mg). The resulting solution was stirred for 2 h at 110° C. in an oil bath. The resulting mixture was concentrated under vacuum. The residue was applied onto a silica gel column with ethyl acetate/petroleum ether (0:1-1:3). This resulted in 130 mg (39%) of methyl 4-(4-[[2-(4-chlorophenyl)-4,4-dimethylcyclohex-1-en-1-yl]methyl]piperazin-1-yl)-2-(12,12-dimethyl-4-[[2-(trimethylsilyl)ethoxy]methyl]-13-oxa-2,4,10-triazatricyclo[7.4.0.0ˆ[3,7]]trideca-1,3(7), 5,8-tetraen-10-yl)benzoate as a yellow solid. LC-MS-PH-PHNW-4-40-4: (ES, m/z): M+1=784, R,T=1.331 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min.

Synthesis of methyl 4-(4-[[2-(4-chlorophenyl)-4,4-dimethylcyclohex-1-en-1-yl]methyl]piperazin-1-yl)-2-[12,12-dimethyl-13-oxa-2,4,10-triazatricyclo[7.4.0.0ˆ[3,7]]trideca-1,3(7),5,8-tetraen-10-yl]benzoate: Into a 40-mL vial, was placed methyl 4-(4-[[2-(4-chlorophenyl)-4,4-dimethylcyclohex-1-en-1-yl]methyl]piperazin-1-yl)-2-(12,12-dimethyl-4-[[2-(trimethylsilyl)ethoxy]methyl]-13-oxa-2,4,10-triazatricyclo[7.4.0.0ˆ[3,7]]trideca-1,3(7), (130 mg, 0.17 mmol, 1 equiv), TBAF (3 g), THF (10 mL), ethane-1,2-diamine (2 g). The resulting solution was stirred for overnight at 60° C. in an oil bath. The reaction was then quenched by the addition of 10 mL of water. The resulting solution was extracted with 2×10 mL of ethyl acetate. The resulting mixture was washed with 3×10 mL of brine. The mixture was dried over anhydrous sodium sulfate and filtrate and concentrated under vacuum. The residue was applied onto a silica gel column with ethyl acetate/petroleum ether (0:1-1:3). This resulted in 110 mg (crude) of methyl 4-(4-[[2-(4-chlorophenyl)-4,4-dimethylcyclohex-1-en-1-yl]methyl]piperazin-1-yl)-2-[12,12-dimethyl-13-oxa-2,4,10-triazatricyclo[7.4.0.0ˆ[3,7]]trideca-1,3(7),5,8-tetraen-10-yl]benzoate as a yellow solid. LC-MS-PH-PHNW-4-40-5: (ES, m/z): M+1=654, R,T=1.107 min. The measurements of the retention were done with a reversed phase column (C18).

Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min.

Synthesis of 4-(4-[[2-(4-chlorophenyl)-4,4-dimethylcyclohex-1-en-1-yl]methyl]piperazin-1-yl)-2-[12,12-dimethyl-13-oxa-2,4,10-triazatricyclo[7.4.0.0ˆ[3,7]]trideca-1,3(7),5,8-tetraen-10-yl]benzoic acid: Into a 8-mL vial, was placed methyl 4-(4-[[2-(4-chlorophenyl)-4,4-dimethylcyclohex-1-en-1-yl]methyl]piperazin-1-yl)-2-[12,12-dimethyl-13-oxa-2,4,10-triazatricyclo[7.4.0.0ˆ[3,7]]trideca-1,3(7),5,8-tetraen-10-yl]benzoate (80 mg, 0.12 mmol, 1 equiv), MeOH (1 mL), THF (1 mL), $H_2O$ (1 mL), NaOH (19.6 mg, 0.49 mmol, 4 equiv). The resulting solution was stirred for overnight at 60° C. in an oil bath. The pH value of the solution was adjusted to 5 with HCl (1 mol/L). The resulting mixture was concentrated under vacuum. The residue was applied onto a silica gel column with dichloromethane/methanol (1:0-10:1). This resulted in 60 mg (76.64%) of 4-(4-[[2-(4-chlorophenyl)-4,4-dimethylcyclohex-1-en-1-yl]methyl]piperazin-1-yl)-2-[12,12-dimethyl-13-oxa-2,4,10-triazatricyclo[7.4.0.0ˆ[3,7]]trideca-1,3(7),5,8-tetraen-10-yl] benzoic acid as a yellow solid. LC-MS-PH-PHNW-4-40-6: (ES, m/z): M+1=640, R,T=1.359 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min.

Synthesis of 4-(4-[[2-(4-chlorophenyl)-4,4-dimethylcyclohex-1-en-1-yl]methyl]piperazin-1-yl)-2-[12,12-dimethyl-13-oxa-2,4,10-triazatricyclo[7.4.0.0ˆ[3,7]]trideca-1(9),2,5,7-tetraen-10-yl]-N-(4-[[(4-fluorooxan-4-yl)methyl]amino]-3-nitrobenzenesulfonyl)benzamide: Into a 8-mL vial, was placed 4-[[(4-fluorooxan-4-yl)methyl]amino]-3-nitrobenzene-1-sulfonamide (37.5 mg, 0.11 mmol, 1.2 equiv), DCM (5 mL), 4-(4-[[2-(4-chlorophenyl)-4,4-dimethylcyclohex-1-en-1-yl]methyl]piperazin-1-yl)-2-[12,12-dimethyl-13-oxa-2,4,10-triazatricyclo[7.4.0.0ˆ[3,7]]trideca-1,3(7),5,8-tetraen-10-yl]benzoic acid (60 mg, 0.09 mmol, 1 equiv), EDCI (35.9 mg, 0.19 mmol, 2 equiv), DMAP (45.8 mg, 0.37 mmol, 4 equiv). The resulting solution was stirred for overnight at room temperature. The resulting mixture was concentrated under vacuum. The crude product was purified by Flash-Prep-HPLC with the following conditions (IntelFlash-1): Column, C18 silica gel; mobile phase, Water (0.1% FA) and ACN (48.0% ACN up to 53.0% in 7 min, hold 95.0% in 1 min, down to 48.0% in 1 min within 5; Detector, UV 254 nm. This resulted in 25 mg (27%) of 4-(4-[[2-(4-chlorophenyl)-4,4-dimethylcyclohex-1-en-1-yl]methyl]piperazin-1-yl)-2-[12,12-dimethyl-13-oxa-2,4,10-triazatricyclo[7.4.0.0ˆ[3,7]]trideca-1(9),2,5,7-tetraen-10-yl]-N-(4-[[(4-fluorooxan-4-yl)methyl]aminol-3-nitrobenzenesulfonyl)benzamide as a yellow solid. 20.6 mg product was submitted. LC-MS-PH-PHNW-4-40-0: (ES, m/z): M+1=955, R,T=2.655 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min. H-NMR-PH-PHNW-4-40-0: (d-DMSO, 300 ppm): 8.56 (s, 1H), 8.36 (s, 1H), 7.56-7.49 (m, 2H), 7.36-7.33 (m, 2H), 7.06-7.00 (m, 3H), 6.93-6.90 (m, 1H), 6.88-6.74 (M, 2H), 5.99 (m, 1H), 3.78-3.74 (m, 4H), 3.67-3.50 (m, 2H), 3.23 (m, 4H), 2.76-2.72 (m, 2H), 2.22-2.16 (m, 6H), 1.96-1.75 (m, 6H), 1.41-1.39 (m, 8H), 0.91-0.88 (m, 6H).

Example 8: Preparation of 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((tetrahydro-2H-pyran-3-yl)methyl)amino)phenyl)sulfonyl)benzamide Synthesis of 3-nitro-4-(((tetrahydro-2H-pyran-3-yl)methyl)amino)benzenesulfonamide: Into a 50-mL round-bottom flask, was placed (tetrahydro-2H-pyran-3-yl)methanamine (200 mg, 1.74 mmol, 1.00 equiv), THF (5 mL), 4-fluoro-3-nitrobenzene-1-sulfonamide (383 mg, 1.74 mmol, 1.00 equiv), $Cs_2CO_3$ (1.134 g, 3.48 mmol, 2.00 equiv). The resulting solution was stirred for 3h at 50 degrees C. in an oil bath. The resulting mixture was concentrated under vacuum. The residue was applied onto a silica gel column with ethyl acetate/petroleum ether (1/1). This resulted in 270 mg (49.3%) of 3-nitro-4-(((tetrahydro-2H-pyran-3-yl)methyl)amino) benzenesulfonamide as a yellow solid. LC-MS-PH-PHNW-4-41-1: (ES, m/z): M+1=316, R,T=1.25 min. The measurements of the retention were done with a reversed phase column (C18). Shimadzu LCMS 2020; 50*3.0 Kinetex 2.6u XB-ODS, 2.6 microm; Eluent A: water (0.5% FA); Eluent B: Acetonitrile (0.05% TFA); linear gradient from 5% acetonitrile to 100% acetonitrile in 2.6 minutes; Oven temperature 40° C.; flow: 1.0 mL/min.

Synthesis of 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((tetrahydro-2H-pyran-3-yl)methyl)amino)phenyl)sulfonyl)benzamide: Into a 100-mL round-bottom flask, was placed 4-(4-[[2-(4-chlorophenyl)-4,4-dimethylcyclohex-1-en-1-yl]methyl]piperazin-1-yl)-2-[13-oxa-2,4,10-triazatricyclo[7.4.0.0ˆ[3,7]]trideca-1,3(7),5,8-tetraen-10-yl]benzoic acid (50 mg, 0.082 mmol, 1.00 equiv) in dichloromethane (5 mL), EDCI (63 mg, 0.328 mmol, 4.00 equiv), 4-dimethylaminopyridine (20 mg, 0.164 mmol, 2.00 equiv), 3-nitro-4-(((tetrahydro-2H-pyran-4-yl)methyl)amino)benzenesulfonamide (26 mg, 0.082 mmol, 1.00 equiv). The resulting solution was stirred for overnight at 40° C. The resulting mixture was concentrated under vacuum. The crude product was purified by Prep-HPLC with the following conditions (Waters-2767): Column, X-bridge RP18, 5 um, 19*100 mm; mobile phase, 0.03% ammonia in water (0.03% $NH_4HCO_3$ & $NH_4OH$) and $CH_3CN$ (32% $CH_3CN$ up to 52% in 6 min); Detector, UV 254 nm. This resulted in 12.8 mg (17%) of 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide as a yellow solid. LC-MS-PH-PHNW-4-41-0: (ES, m/z): M+1=909, R,T=1.60 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.0 minutes; Oven temperature 40° C.; flow: 1.5 mL/min. 1H NMR (300 MHz, Chloroform-d) δ 12.40 (s, 1H), 8.72 (s, 1H), 8.63 (s, 1H), 8.44 (t, J=5.5 Hz, 1H), 8.10 (d, J=9.0 Hz, 1H), 7.93-7.82 (m, 1H), 7.25 (s, 4H), 7.13 (t, J=2.9 Hz, 1H), 7.00-6.68 (m, 6H), 6.52 (s, 1H), 6.17 (d, J=3.3 Hz, 1H), 4.71 (dd, J=23.6, 10.7 Hz, 2H), 3.99-3.79 (m, 3H), 3.70 (s, 1H), 3.57 (dd, J=18.5, 10.9 Hz, 3H), 3.46-3.17 (m, 7H), 2.80 (s, 2H), 2.29 (s, 3H), 2.21 (s, 2H), 2.03 (d, J=12.3 Hz, 5H), 1.75-1.60 (m, 4H), 1.44 (d, J=8.7 Hz, 3H), 1.28 (s, 1H), 0.97 (s, 6H), 0.87 (s, 1H). The measurements of the NMR spectra were done with BrukerAvanceIII HD 300 MHz with a probe head of BBOF.

Example 9: Preparation of (S)-4-(4-((4'-chloro-5,5-dimethyl-3,4,5,6-tetrahydro-[1,1'-biphenyl]-2-yl)methyl)piperazin-1-yl)-2-(3-methyl-2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide Synthesis of 6-(tert-butoxy)-N-(diphenylmethylidene)-1-[[2-(trimethylsilyl)ethoxy]methyl]-1H-pyrrolo[2,3-b]pyridin-5-amine: Into a 250-mL round-bottom flask, was placed a solution of 5-bromo-6-fluoro-1-[[2-(trimethylsilyl)ethoxy]methyl]-1H-pyrrolo[2,3-b]pyridine (20.7 g, 60 mmol, 1.00 equiv) in dioxane (300 mL), t-BuOK (20.5 g, 180 mmol, 3.00 equiv), xantphos (6.9 g, 12 mmol, 0.20 equiv), $Pd_2(dba)_3 \cdot CHCl_3$ (5.7 g, 0.10 equiv), diphenylmethanimine (14.04 g, 78 mmol, 1.20 equiv). The resulting solution was stirred for overnight at 100° C. The resulting mixture was concentrated under vacuum. The residue was applied onto a silica gel column with ethyl acetate/petroleum ether (0:1-1:20). This resulted in 15 g (crude) of 6-(tert-butoxy)-N-(diphenylmethylidene)-1-[[2-(trimethylsilyl)ethoxy]methyl]-1H-pyrrolo[2,3-b]pyridin-5-amine as white oil. LC-MS-PH-PHNW-4-7-9: (ES, m/z): M+1=500.

Synthesis of 5-amino-1-[[2-(trimethylsilyl)ethoxy]methyl]-1H-pyrrolo[2,3-b]pyridin-6-ol hydrogen chloride salt: Into a 500-mL round-bottom flask, was placed 6-(tert-butoxy)-N-(diphenylmethylidene)-1-[[2-(trimethylsilyl)ethoxy]methyl]-1H-pyrrolo[2,3-b]pyridin-5-amine (15 g, 30.02 mmol, 1.00 equiv) in dioxane (120 mL), HCl/dioxane (4M, 30 mL). The resulting solution was stirred for 5 h at room temperature. The resulting solution was diluted with 500 mL of ether. The solids were collected by filtration. This resulted in 5 g (crude) of 5-amino-1-[[2-(trimethylsilyl)ethoxy]methyl]-1H-pyrrolo[2,3-b]pyridin-6-ol hydrogen chloride salt as a red solid, Q-NMR show it might converted into 3 hydrogen chloride salt. LC-MS-PH-PHNW-4-10-1: (ES, m/z): M+1=280, R,T=0.811 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient.

Synthesis of 12-methyl-4-[[2-(trimethylsilyl)ethoxy]methyl]-13-oxa-2,4,10-triazatricyclo[7.4.0.0ˆ[3,7]]trideca-1(9),2,5,7-tetraen-11-one: Into a 100-mL round-bottom flask, was placed 5-amino-1-[[2-(trimethylsilyl)ethoxy]methyl]-1H-pyrrolo[2,3-b]pyridin-6-ol (1.5 g, 5.37 mmol, 1 equiv), DMF (50 mL), $K_2CO_3$ (2.2 g, 16.11 mmol, 3 equiv). This was followed by the addition of 2-chloropropanoyl chloride (1.4 g, 10.74 mmol, 2 equiv) dropwise with stirring at 0° C. The resulting solution was stirred for overnight at room temperature. The reaction was then quenched by the addition of 50 mL of water. The resulting solution was extracted with 2×50 mL of ethyl acetate. The resulting mixture was washed with 2×50 mL of brine. The mixture was dried over anhydrous sodium sulfate and filtrate and concentrated under vacuum. The residue was applied onto a silica gel column with ethyl acetate/petroleum ether (0:1-1:3). This resulted in 500 mg (27.93%) of 12-methyl-4-[[2-(trimethylsilyl)ethoxy]methyl]-13-oxa-2,4,10-triazatricyclo[7.4.0.0ˆ[3,7]]trideca-1(9),2,5,7-tetraen-11-one as a yellow solid. LC-MS-PH-PHNW-4-37-1: (ES, m/z): M+1=334, R,T=1.123 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min. H-NMR-PH-PHNW-4-37-1: (CDCl3, 300 ppm): 8.34 (s, 1H), 7.63 (d, J=3 Hz, 1H), 7.42-7.28 (m, 1H), 6.46 (d, J=3 Hz, 1H), 5.68 (s, 2H), 4.92-4.85 (m, 1H), 3.63-3.53 (m, 2H), 1.85-1.81 (d, J=12 Hz, 3H), 0.94-0.89 (m, 2H), −0.154 (s, 9H).

Synthesis of 12-methyl-4-[[2-(trimethylsilyl)ethoxy]methyl]-13-oxa-2,4,10-triazatricyclo[7.4.0.0ˆ[3,7]]trideca-1(9),2,5,7-tetraene & (12 S)-12-methyl-4-[[2-(trimethylsilyl)ethoxy]methyl]-13-oxa-2,4,10-triazatricyclo[7.4.0.0ˆ[3,7]]trideca-1(9),2,5,7-tetraene & (12 R)-12-methyl-4-[[2-(trimethylsilyl)ethoxy]methyl]-13-oxa-2,4,10-triazatricyclo[7.4.0.0ˆ[3,7]]trideca-1(9),2,5,7-tetraene: Into a 100-mL 3-necked round-bottom flask, was placed 12-methyl-4-[[2-(trimethylsilyl)ethoxy]methyl]-13-oxa-2,4,10-triazatricyclo[7.4.0.0ˆ[3,7]]trideca-1(9),2,5,7-tetraen-11-one (500 mg, 1.50 mmol, 1 equiv), THF (20 mL). This was followed by the addition of $LiAlH_4$ (113.8 mg, 3.00 mmol, 2 equiv), in portions at 0° C. The resulting solution was stirred for 1 overnight at room temperature. The reaction was then quenched by the addition of 20 mL of water. The solids were filtered out. The resulting solution was extracted with 2×20 mL of ethyl acetate. The resulting mixture was washed with 2×20 mL of brine. The mixture was dried over anhydrous sodium sulfate and filtrate and concentrated under vacuum. The residue was applied onto a silica gel column with ethyl acetate/petroleum ether (0:1-1:3). This resulted in 450 mg (93%) of 12-methyl-4-[[2-(trimethylsilyl)ethoxy]methyl]-13-oxa-2,4,10-triazatricyclo[7.4.0.0ˆ[3,7]]trideca-1(9),2,5,7-tetraene as a yellow solid.

The crude 12-methyl-4-[[2-(trimethylsilyl)ethoxy]methyl]-13-oxa-2,4,10-triazatricyclo[7.4.0.0ˆ[3,7]]trideca-1(9),2,5,7-tetraene (450 mg) was purified by Chiral-Prep-HPLC with the following conditions: (SHIMADZU LC-20AT): Column, CHIRALPAK IC; mobile phase A:n-hexane, Phase B:ethanol; Detector, 220 nm. This resulted in 200 mg (44%) of (12S)-12-methyl-4-[[2-(trimethylsilyl)ethoxy]methyl]-13-oxa-2,4,10-triazatricyclo[7.4.0.0ˆ[3,7]]trideca-1(9),2,5,7-tetraene as a yellow solid.

This resulted in 200 mg (44%) of (12R)-12-methyl-4-[[2-(trimethylsilyl)ethoxy]methyl]-13-oxa-2,4,10-triazatricyclo[7.4.0.0ˆ[3,7]]trideca-1(9),2,5,7-tetraene as a yellow solid. LC-MS-PH-PHNW-4-37-2: (ES, m/z): M+1=320, R,T=1.107 min.

The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min. H-NMR-PH-PHNW-4-37-2: (CDCl3, 300 ppm): 7.63 (s, 1H), 7.17 (s, 1H), 6.36-6.35 (d, J=3 Hz, 1H), 5.57-5.52 (m, 2H), 4.59-4.55 (m, 1H), 3.62-3.46 (m, 3H), 3.18-3.14 (m, 1H), 1.62-1.44 (m, 3H), 0.93-0.88 (m, 2H), −0.17 (s, 9H).

Synthesis of methyl 4-(4-[[2-(4-chlorophenyl)-4,4-dimethylcyclohex-1-en-1-yl]methyl]piperazin-1-yl)-2-[(12 S)-12-methyl-4-[[2-(trimethylsilyl)ethoxy]methyl]-13-oxa-2,4,10-triazatricyclo[7.4.0.0ˆ[3,7]]trideca-1(9),2,4,10-triazatricyclo[7.4.0.0ˆ3,7]trideca-1(9),2,5,7-tetraen-10-yl]benzoate: Into a 8-mL vial, was placed (12S)-12-methyl-4-[[2-(trimethylsilyl)ethoxy]methyl]-13-oxa-2,4,10-triazatricyclo[7.4.0.0ˆ[3,7]]trideca-1(9),2,5,7-tetraene (200 mg, 0.63 mmol, 1 equiv), methyl 2-bromo-4-(4-[[2-(4-chlorophenyl)-

4,4-dimethylcyclohex-1-en-1-yl]methyl]piperazin-1-yl) benzoate (399.6 mg, 0.75 mmol, 1.2 equiv), $Cs_2CO_3$ (611.9 mg, 1.88 mmol, 3 equiv), Dioxane (5 mL), Chloro[9,9-dimethyl-4,5-bis(diphenylphosphino)xanthene][2-amino-1,1-biphenyl-2-yl]palladium(II) (120 mg). The resulting solution was stirred for 2 hr at 110° C. in an oil bath. The resulting mixture was concentrated under vacuum. The residue was applied onto a silica gel column with ethyl acetate/petroleum ether (0:1-1:10). This resulted in 250 mg (51.83%) of methyl 4-(4-[[2-(4-chlorophenyl)-4,4-dimethylcyclohex-1-en-1-yl]methyl]piperazin-1-yl)-2-[(12S)-12-methyl-4-[[2-(trimethylsilyl)ethoxy]methyl]-13-oxa-2,4,10-triazatricyclo[7.4.0.0ˆ[3,7]]trideca-1(9),2,4,10-triazatricyclo[7.4.0.0ˆ[3,7]]trideca-1(9),2,5,7-tetraen-10-yl] benzoate as a yellow solid.

Synthesis of methyl 4-(4-[[2-(4-chlorophenyl)-4,4-dimethylcyclohex-1-en-1-yl]methyl]piperazin-1-yl)-2-[(12S)-12-methyl-13-oxa-2,4,10-triazatricyclo[7.4.0.0ˆ[3,7]]trideca-1(9),2,5,7-tetraen-10-yl]benzoate. Into a 100-mL round-bottom flask, was placed methyl 4-(4-[[2-(4-chlorophenyl)-4,4-dimethylcyclohex-1-en-1-yl]methyl]piperazin-1-yl)-2-[(12S)-12-methyl-4-[[2-(trimethylsilyl)ethoxy]methyl]-13-oxa-2,4,10-triazatricyclo[7.4.0.0ˆ[3,7]]trideca-1(9),2 (250 mg, 0.32 mmol, 1 equiv), TBAF (3 g, 11.47 mmol, 35.36 equiv), THF (30 mL), ethane-1,2-diamine (2 g, 33.28 mmol, 102.56 equiv). The resulting solution was stirred for 12 h at 70° C. in an oil bath. The reaction was then quenched by the addition of 50 mL of water. The resulting solution was extracted with 2×50 mL of ethyl acetate. The resulting mixture was washed with 3×50 mL of brine. The mixture was dried over anhydrous sodium sulfate and filtrate and concentrated under vacuum. The residue was applied onto a silica gel column with ethyl acetate/petroleum ether (0:1-1:3). This resulted in 90 mg (43%) of methyl 4-(4-[[2-(4-chlorophenyl)-4,4-dimethylcyclohex-1-en-1-yl]methyl]piperazin-1-yl)-2-[(12S)-12-methyl-13-oxa-2,4,10-triazatricyclo[7.4.0.0ˆ[3,7]]trideca-1(9),2,5,7-tetraen-10-yl]benzoate as a yellow solid. H-NMR-PH-PHNW-4-37-50: (CDCl3, 300 ppm): 8.24 (s, 1H), 7.89-7.86 (d, J=9 Hz, 1H), 7.32-7.24 (m, 6H), 7.14-7.01 (m, 1H), 6.97-6.94 (m, 2H), 6.73-6.65 (m, 2H), 6.18 (s, 1H), 3.67-3.53 (m, 3H), 3.32-3.18 (m, 3H), 2.98-2.80 (m, 1H), 2.30-2.04 (m, 6H), 1.99 (s, 2H), 1.56-1.50 (m, 5H), 0.91-0.88 (m, 6H).

Synthesis of 4-(4-[[2-(4-chlorophenyl)-4,4-dimethylcyclohex-1-en-1-yl]methyl]piperazin-1-yl)-2-[(12 S)-12-methyl-13-oxa-2,4,10-triazatricyclo[7.4.0.0ˆ[3,7]]trideca-1(9),2,5,7-tetraen-10-yl]benzoic acid. Into a 8-mL vial, was placed methyl 4-(4-[[2-(4-chlorophenyl)-4,4-dimethylcyclohex-1-en-1-yl]methyl]piperazin-1-yl)-2-[(12S)-12-methyl-13-oxa-2,4,10-triazatricyclo[7.4.0.0ˆ[3,7]]trideca-1(9),2,5,7-tetraen-10-yl]benzoate (90 mg, 0.14 mmol, 1 equiv), MeOH (1 mL), $H_2O$ (1 mL), THF (1 mL), NaOH (22.5 mg, 0.56 mmol, 4 equiv). The resulting solution was stirred for overnight at 60° C. in an oil bath. The pH value of the solution was adjusted to 5 with HCl (1 mol/L). The resulting mixture was concentrated under vacuum. The residue was applied onto a silica gel column with dichloromethane/methanol (1:0-10:1). This resulted in 80 mg (90%) of 4-(4-[[2-(4-chlorophenyl)-4,4-dimethylcyclohex-1-en-1-yl]methyl]piperazin-1-yl)-2-[(12S)-12-methyl-13-oxa-2,4,10-triazatricyclo[7.4.0.0ˆ[3,7]]trideca-1(9),2,5,7-tetraen-10-yl]benzoic acid as a yellow solid. LC-MS: (ES, m/z): M+1=626, R,T=1.035 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min.

Synthesis of (S)-4-(4-((4'-chloro-5,5-dimethyl-3,4,5,6-tetrahydro-[1,1'-biphenyl]-2-yl)methyl)piperazin-1-yl)-2-(3-methyl-2,3-dihydropyrrolo[3',2':5,6]pyrido[2,3-b][1,4]oxazin-1(6H)-yl)-N-((3-nitro-4-(tetrahydro-2H-pyran-4-yl)methyl)amino)phenyl)sulfonyl)benzamide. Into a 8-mL vial, was placed 4-(4-[[2-(4-chlorophenyl)-4,4-dimethylcyclohex-1-en-1-yl]methyl]piperazin-1-yl)-2-[(12R or S)-12-methyl-13-oxa-2,4,10-triazatricyclo[7.4.0.0ˆ[3,7]]trideca-1(9),2,5,7-tetraen-10-yl]benzoic acid (90 mg, 0.14 mmol, 1 equiv), 4-[[(4-fluorooxan-4-yl)methyl]amino]-3-nitrobenzene-1-sulfonamide (57.5 mg, 0.17 mmol, 1.2 equiv), DCM (5 mL), DMAP (70.2 mg, 0.57 mmol, 4 equiv), EDCI (55.1 mg, 0.29 mmol, 2.00 equiv). The resulting solution was stirred for overnight at room temperature. The resulting mixture was concentrated. The crude product was purified by Flash-Prep-HPLC with the following conditions (IntelFlash-1): Column, C18 silica gel; mobile phase, Water (0.1% FA) and ACN (48.0% ACN up to 53.0% in 7 min, hold 95.0% in 1 min, down to 48.0% in 1 min, hold 48.0% in 1 min) within 5 min; Detector, UV 254 nm. This resulted in 22 mg (20%) of (S)-4-(4-((4'-chloro-5,5-dimethyl-3,4,5,6-tetrahydro-[1,1'-biphenyl]-2-yl)methyl)piperazin-1-yl)-2-(3-methyl-2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide. LC-MS: (ES, m/z): M+1=923, R,T=2.653 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min. H-NMR: (d-$CDCl_3$, 300 ppm): 8.62 (s, 1H), 8.44-8.42 (m, 2H), 8.09-8.06 (m, 1H), 7.85-7.70 (m, 1H), 7.28-7.22 (m, 2H), 6.94-6.80 (m, 3H), 6.72-6.62 (m, 2H), 6.10 (s, 1H), 4.05-4.00 (m, 2H), 3.50-3.17 (m, 10H), 2.95-2.35 (m, 2H), 2.27-2.19 (m, 4H), 1.98-1.70 (m, 5H), 1.60-1.26 (m, 11H), 0.95 (s, 6H).

Example 10: Preparation of (R)-4-(4-((4'-chloro-5,5-dimethyl-3,4,5,6-tetrahydro-[1,1'-biphenyl]-2-yl)methyl)piperazin-1-yl)-2-(3-methyl-2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide Synthesis of N-[(2R)-2-hydroxypropyl]-4-methylbenzene-1-sulfonamide: Into a 250-mL round-bottom flask, was placed (2R)-1-aminopropan-2-ol (5 g, 1 equiv), DCM (70 mL), TsCl (12.67 g, 1 equiv). This was followed by the addition of TEA (7.41 g, 1.1 equiv) at 0° C. The resulting solution was stirred for 3 hr at 0° C. The resulting mixture was concentrated. The residue was applied onto a silica gel column with ethyl acetate/petroleum ether (1/1). This resulted in 8 g of N-(2R)-2-hydroxypropyl]-4-methylbenzene-1-sulfonamide as a white solid. $^1$H NMR ((300 MHz, DMSO-d6, ppm): δ 7.74-7.63 (m, 2H), 7.52-7.34 (m, 3H), 4.66 (d, J=4.7 Hz, 1H), 3.58 (qd, J=6.3, 4.8 Hz, 1H), 2.73-2.50 (m, 2H), 2.39 (s, 3H), 0.99 (d, J=6.2 Hz, 3H).

Synthesis of methyl 2-bromo-4-(4-[[2-(4-chlorophenyl)-4,4-dimethylcyclohex-1-en-1-yl]methyl]piperazin-1-yl) benzoate: Into a 250-mL round-bottom flask, was placed a solution of 1-[[2-(4-chlorophenyl)-4,4-dimethylcyclohex-1-en-1-yl]methyl]piperazine (15.09 g, 47.32 mmol, 1.00 equiv) in DMA (150 mL), DIEA (12.9 g, 99.81 mmol, 2.00 equiv), methyl 2-bromo-4-fluorobenzoate (11.6 g, 49.78 mmol, 1.00 equiv). The resulting solution was stirred for 12 h at 100 degree. The reaction mixture was cooled to room temperature. The reaction was then quenched by the addition of 50 mL of water. The resulting solution was extracted with 3×100 mL of ethyl acetate and the organic layers combined. The resulting mixture was washed with 3×100 mL of brine. The mixture was dried over anhydrous sodium sulfate, then filtered and concentrated under vacuum. The residue was applied onto a silica gel column with ethyl acetate/petroleum ether (0:1-1:5). This resulted in 7 g (crude) of methyl 2-bromo-4-(4-[[2-(4-chlorophenyl)-4,4-dimethylcyclohex-1-en-1-yl]methyl]piperazin-1-yl)benzoate as yellow oil. LC-MS: (ES, m/z): M+1=533, 531.

Synthesis of N-[(2R)-2-[(5-bromo-1-[[2-(trimethylsilyl)ethoxy]methyl]-1H-pyrrolo[2,3-b]pyridin-6-yl]oxy]propyl]-4-methylbenzene-1-sulfonamide: Into a 100-mL round-bottom flask, was placed N-[(2R)-2-hydroxypropyl]-4-methylbenzene-1-sulfonamide (1 g, 1.5 equiv), DMF (3 mL). This was followed by the addition of NaH (0.35 g, 3 equiv) at 0° C. in 10 min. To this was added 5-bromo-6-fluoro-1-[[2-(trimethylsilyl)ethoxy]methyl]-1H-pyrrolo[2,3-b]pyridine (1 g, 1 equiv) at 0° C. The resulting solution was stirred for 4 hr at room temperature. The reaction was then quenched by the addition of 20 mL of water. The resulting solution was extracted with 3×50 mL of ethyl acetate and the organic layers combined and concentrated. The residue was applied onto a silica gel column with ethyl acetate/petroleum ether (1/3). This resulted in 400 mg of N-[(2R)-2-[(5-bromo-1-[[2-(trimethylsilyl)ethoxy]methyl]-1H-pyrrolo[2,3-b]pyridin-6-yl]oxy]propyl]-4-methylbenzene-1-sulfonamide as a yellow solid. $^1$H NMR (300 MHz, DMSO-d6, ppm): δ 8.18 (s, 1H), 7.72-7.62 (m, 2H), 7.41 (d, J=3.5 Hz, 1H), 7.28 (d, J=8.0 Hz, 2H), 6.42 (d, J=3.6 Hz, 1H), 5.50 (q, J=10.8 Hz, 2H), 5.16 (q, J=6.1 Hz, 1H), 3.53-3.38 (m, 2H), 3.13 (dd, J=13.4, 6.0 Hz, 1H), 2.98 (dd, J=13.4, 5.8 Hz, 1H), 2.29 (s, 3H), 1.28 (d, J=6.2 Hz, 3H), 0.80 (ddt, J=16.1, 14.1, 7.1 Hz, 2H), 0.13 (s, 9H).

Synthesis of (12R)-12-methyl-10-(4-methylbenzenesulfonyl)-4-[[2-(trimethylsilyl)ethoxy]methyl]-13-oxa-2,4,10-triazatricyclo[7.4.0.0ˆ[3,7]]trideca-1(9),2,5,7-tetraene: Into a 100-mL round-bottom flask purged and maintained with an inert atmosphere of nitrogen, was placed N-[(2R)-2-[(5-bromo-1-[[2-(trimethylsilyl)ethoxy]methyl]-1H-pyrrolo[2,3-b]pyridin-6-yl]oxy]propyl]-4-methylbenzene-1-sulfonamide (3.9 g, 1 equiv), dioxane (50 mL), t-BuXPhos 3G (560 mg, 0.1 equiv), Cs$_2$O$_3$ (6.9 g, 3 equiv). The resulting solution was stirred for 4 hr at 90° C. The resulting mixture was concentrated. The residue was applied onto a silica gel column with ethyl acetate/petroleum ether (1/3). This resulted in 3.3 g of (12R)-12-methyl-10-(4-methylbenzenesulfonyl)-4-[[2-(trimethylsilyl)ethoxy]methyl]-13-oxa-2,4,10-triazatricyclo[7.4.0.0ˆ[3,7]]trideca-1(9),2,5,7-tetraene as colorless oil. $^1$H-NMR (300 MHz, DMSO-d6, ppm): δ 8.28 (s, 1H), 7.56-7.39 (m, 3H), 7.39-7.30 (m, 2H), 6.52 (d, J=3.6 Hz, 1H), 5.43 (s, 2H), 4.28 (dd, J=14.6, 2.6 Hz, 1H), 3.61-3.41 (m, 3H), 3.26-3.11 (m, 1H), 2.35 (s, 3H), 1.32-1.11 (m, 3H), 0.89-0.74 (m, 2H), 0.11 (s, 9H).

Synthesis of (12R)-12-methyl-4-[[2-(trimethylsilyl)ethoxy]methyl]-13-oxa-2,4,10-triazatricyclo[7.4.0.0ˆ[3,7]]trideca-1(9),2,5,7-tetraene: Into a 100-mL 3-necked round-bottom flask, was placed Na (1.31 g, 9.4 equiv), naphthalene (0.76 g, 6 equiv). This was followed by the addition of DME (15 mL) for 30 min at room temperature. To this was added the solution (12R)-12-methyl-10-(4-methylbenzenesulfonyl)-4-[[2-(trimethylsilyl)ethoxy]methyl]-13-oxa-2,4,10-triazatricyclo[7.4.0.0ˆ[3,7]]trideca-1(9),2,5,7-tetraene (2.8 g, 1 equiv) in THF (15 mL) at −78° C. The resulting solution was stirred for 3 hr at room temperature. The reaction was then quenched by the addition of 30 mL of NH$_4$Cl. The resulting solution was extracted with 3×100 mL of ethyl acetate and the organic layers combined and concentrated. The residue was applied onto a silica gel column with ethyl acetate/petroleum ether (1/3). This resulted in 1.4 g of (12R)-12-methyl-4-[[2-(trimethylsilyl)ethoxy]methyl]-13-oxa-2,4,10-triazatricyclo[7.4.0.0ˆ[3,7]]trideca-1(9),2,5,7-tetraene as a colorless oil. LC-MS (ES, m/z): 320 [M+1]$^+$; RT=1.61 min.

Synthesis of methyl 4-(4-[[2-(4-chlorophenyl)-4,4-dimethylcyclohex-1-en-1-yl]methyl]piperazin-1-yl)-2-[(12S)-12-methyl-4-[[2-(trimethylsilyl)ethoxy]methyl]-13-oxa-2,4,10-triazatricyclo[7.4.0.0ˆ[3,7]]trideca-1(9),2,5,7-tetraen-10-yl]benzoate: Into a 250-mL round-bottom flask purged and maintained with an inert atmosphere of nitrogen, was placed (12R)-12-methyl-4-[[2-(trimethylsilyl)ethoxy]methyl]-13-oxa-2,4,10-triazatricyclo[7.4.0.0ˆ[3,7]]trideca-1(9),2,5,7-tetraene (1.178 g, 1 equiv), methyl 2-bromo-4-(4-[[2-(4-chlorophenyl)-4,4-dimethylcyclohex-1-en-1-yl]methyl]piperazin-1-yl)benzoate (2.35 g, 1.2 equiv), dioxane (15 mg, 15 equiv), Cs$_2$CO$_3$ (3.62 g, 3 equiv), XantPhos (328 mg, 0.1 equiv). The resulting solution was stirred for 2 hr at 110° C. The resulting mixture was concentrated. The residue was applied onto a silica gel column with ethyl acetate/petroleum ether (1/3). This resulted in 3.2 g of methyl 4-(4-[[2-(4-chlorophenyl)-4,4-dimethylcyclohex-1-en-1-yl]methyl]piperazin-1-yl)-2-[(12S)-12-methyl-4-[[2-(trimethylsilyl)ethoxy]methyl]-13-oxa-2,4,10-triazatricyclo[7.4.0.0ˆ[3,7]]trideca-1(9),2,5,7-tetraen-10-yl]benzoate as a yellow solid. LC-MS (ES, m/z): 770 [M+1]$^+$; RT=1.33 min.

Synthesis of methyl 4-(4-[[2-(4-chlorophenyl)-4,4-dimethylcyclohex-1-en-1-yl]methyl]piperazin-1-yl)-2-[(12R)-12-methyl-13-oxa-2,4,10-triazatricyclo[7.4.0.0ˆ[3,7]]trideca-1(9),2,5,7-tetraen-10-yl]benzoate: Into a 250-mL round-bottom flask, was placed methyl 4-(4-[[2-(4-chlorophenyl)-4,4-dimethylcyclohex-1-en-1-yl]methyl]piperazin-1-yl)-2-[(12R)-12-methyl-4-[[2-(trimethylsilyl)ethoxy]methyl]-13-oxa-2,4,10-triazatricyclo[7.4.0.0ˆ[3,7]]trideca-1(9),2,5,7-tetraen-10-yl]benzoate (3.2 g, 1 equiv), THF (50 mL), TBAF (20 g), ethane-1,2-diamine (33 g). The resulting solution was stirred for 5 hr at 70° C. The reaction was then quenched by the addition of 50 mL of water. The resulting solution was extracted with 3×100 mL of ethyl acetate and the organic layers combined and concentrated. The residue was applied onto a silica gel column with dichloromethane/methanol (10/1). This resulted in 2.2 g of methyl 4-(4-[[2-(4-chlorophenyl)-4,4-dimethylcyclohex-1-en-1-yl]methyl]piperazin-1-yl)-2-[(12R)-12-methyl-13-oxa-2,4,10-triazatricyclo[7.4.0.0ˆ[3,7]]trideca-1(9),2,5,7-tetraen-10-yl]benzoate as a yellow solid. LC-MS-(ES, m/z): 640 [M+1]$^+$; RT=2.51 min Synthesis of 4-(4-[[2-(4-chlorophenyl)-4,4-dimethylcyclohex-1-en-1-yl]methyl]piperazin-1-yl)-2-[(12R)-12-methyl-13-oxa-2,4,10-triazatricyclo[7.4.0.0ˆ[3,7]]trideca-1(9),2,5,7-tetraen-10-yl]benzoic acid: Into a 250-mL round-bottom flask, was placed methyl 4-(4-[[2-(4-chlorophenyl)-4,4-dimethylcyclohex-1-en-1-yl]methyl]piperazin-1-yl)-2-[(12R)-12-methyl-13-oxa-2,4,10-triazatricyclo[7.4.0.0ˆ[3,7]]trideca-1(9),2,5,7-tetraen-10-yl]benzoate (2.2 g, 1 equiv), MEOH/H$_2$O/THF (10 mL/10 ml/10 mL). The resulting solution was stirred for 5 hr at 60° C. The resulting mixture was concentrated. The resulting solution was extracted with 3×100 mL of dichloromethane and the organic layers combined and concentrated. The residue was applied onto a silica gel column with dichloromethane/methanol (10/1). This resulted in 1.6 g of 4-(4-[[2-(4-chlorophenyl)-4,4- dimethylcyclohex-1-en-1-yl]methyl]piperazin-1-yl)-2-[(12R)-12-methyl-13-oxa-2,4,10-triazatricyclo[7.4.0.0^[3,7]]trideca-1(9),2,5,7-tetraen-10-yl]benzoic acid as yellow oil. LC-MS (ES, m/z): 626 [M+1]$^+$; RT=2.47 min Synthesis of (R)-4-(4-((4'-chloro-5,5-dimethyl-3,4,5,6-tetrahydro-[1,1'-biphenyl]-2-yl)methyl)piperazin-1-yl)-2-(3-methyl-2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide: Into a 250-mL round-bottom flask, was placed 4-(4-[[2-(4-chlorophenyl)-4,4-dimethylcyclohex-1-en-1-yl]methyl]piperazin-1-yl)-2-[(12R)-12-methyl-13-oxa-2,4,10-triazatricyclo[7.4.0.0^[3,7]]trideca-1(9),2,5,7-tetraen-10-yl]benzoic acid (1.6 g, 1 equiv), DCM (20 mL), 3-nitro-4-[[(oxan-4-yl)methyl]amino]benzene-1-sulfonamide (890 mg, 1.2 equiv), DMAP (1.25 g, 4 equiv), EDCI (980 mg, 2 equiv). The resulting solution was stirred for 14 hr at room temperature. The resulting mixture was concentrated. The residue was applied onto a silica gel column with EA/DCM (1/10). This resulted in 0.82 g of (R)-4-(4-((4'-chloro-5,5-dimethyl-3,4,5,6-tetrahydro-[1,1'-biphenyl]-2-yl)methyl)piperazin-1-yl)-2-(3-methyl-2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide as a yellow solid. LC-MS (ES, m/z): 923 [M+1]$^+$; RT=3.50 min. [a]=+17.8 (C=0.105 g/100 mL in CH$_2$Cl$_2$, T=27.0° C.) $^1$H NMR (300 MHz, CDCl$_3$, ppm): δ 12.48 (s, 1H), 8.62 (d, J=2.4 Hz, 2H), 8.54-8.38 (m, 1H), 8.16-7.95 (m, 1H), 7.81-7.71 (m, 1H), 7.32-7.12 (m, 6H), 7.07 (t, J=2.9 Hz, 1H), 6.97-6.77 (m, 3H), 6.76-6.60 (m, 2H), 6.52 (s, 1H), 6.09 (d, J=3.0 Hz, 1H), 4.88 (d, J=7.7 Hz, 1H), 4.02 (dd, J=11.8, 4.2 Hz, 2H), 3.55-3.34 (m, 4H), 3.32-3.14 (m, 5H), 3.08 (s, 1H), 2.77 (d, J=9.6 Hz, 2H), 2.28 (s, 3H), 2.19 (s, 2H), 1.99 (d, J=7.6 Hz, 4H), 1.72 (d, J=12.7 Hz, 2H), 1.45 (ddd, J=24.5, 12.3, 5.8 Hz, 6H), 0.94 (d, J=2.1 Hz, 6H).

The compounds below were/are being prepared by methods substantially identical, similar, or analogous to those disclosed in above Schemes and Examples:

| Example | Chemical Name | m/z(MH$^+$) |
|---|---|---|
| Cpd-1 | (R)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(3-(trifluoromethyl)-2,3-dihydropyrrolo[3',2':5,6]pyrido[2,3-b][1,4]oxazin-1(6H)-yl)benzamide | 977 |
| Cpd-2 | (S)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(3-(trifluoromethyl)-2,3-dihydropyrrolo[3',2':5,6]pyrido[2,3-b][1,4]oxazin-1(6H)-yl)benzamide | 977 |
| Cpd-3 | 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]thiazin-1(6H)-yl)-N-((3-nitro-4-(((tetrahydro-2H-pyran-4-yl)methyl)amino)phenyl)sulfonyl)benzamide | 925 |
| Cpd-4 | (R)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(3-(trifluoromethyl)-2,3-dihydropyrrolo[3',2':5,6]pyrido[2,3-b][1,4]thiazin-1(6H)-yl)benzamide | 993 |
| Cpd-5 | (S)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(3-(trifluoromethyl)-2,3-dihydropyrrolo[3',2':5,6]pyrido[2,3-b][1,4]thiazin-1(6H)-yl)benzamide | 993 |
| Cpd-6 | 4-(4-((4'-chloro-5,5-dimethyl-3,4,5,6-tetrahydro-[1,1'-biphenyl]-2-yl)methyl)piperazin-1-yl)-2-(4,4-dioxido-2,3-dihydropyrrolo[3',2':5,6]pyrido[2,3-b][1,4]thiazin-1(6H)-yl)-N-((3-nitro-4-(((tetrahydro-2H-pyran-4-yl)methyl)amino)phenyl)sulfonyl)benzamide | 957 |
| Cpd-7 | N-((4-((((R)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-((S)-3-methyl-2,3-dihydropyrrolo[3',2':5,6]pyrido[2,3-b][1,4]oxazin-1(6H)-yl)benzamide | 925 |
| Cpd-8 | N-((4-((((S)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-((S)-3-methyl-2,3-dihydropyrrolo[3',2':5,6]pyrido[2,3-b][1,4]oxazin-1(6H)-yl)benzamide | 925 |
| Cpd-9 | 4-(4-((4'-chloro-5,5-dimethyl-3,4,5,6-tetrahydro-[1,1'-biphenyl]-2-yl)methyl)piperazin-1-yl)-N-((4-((((S)-2-fluoro-1,4-dioxan-2-yl)methyl)amino)-3-nitrophenyl)sulfonyl)-2-((S)-3-methyl-2,3-dihydropyrrolo[3',2':5,6]pyrido[2,3-b][1,4]oxazin-1(6H)-yl)benzamide | 943 |
| Cpd-10 | 4-(4-((4'-chloro-5,5-dimethyl-3,4,5,6-tetrahydro-[1,1'-biphenyl]-2-yl)methyl)piperazin-1-yl)-N-((4-((((R)-2-fluoro-1,4-dioxan-2-yl)methyl)amino)-3-nitrophenyl)sulfonyl)-2-((S)-3-methyl-2,3- | 943 |

| Example | Chemical Name | m/z(MH⁺) |
|---|---|---|
| | dihydropyrrolo[3',2':5,6]pyrido[2,3-b][1,4]oxazin-1(6H)-yl)benzamide | |
| Cpd-11 | (R)-N-((4-(((1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzamide | 911 |
| Cpd-12 | (S)-N-((4-(((1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzamide | 911 |
| Cpd-13 | (S)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((2-fluoro-1,4-dioxan-2-yl)methyl)amino)-3-nitrophenyl)sulfonyl)benzamide | 929 |
| Cpd-14 | (R)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((2-fluoro-1,4-dioxan-2-yl)methyl)amino)-3-nitrophenyl)sulfonyl)benzamide | 929 |
| Cpd-15 | (R)-N-((4-(((1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(3,3-difluoro-2,3-dihydropyrrolo[3',2':5,6]pyrido[2,3-b][1,4]oxazin-1(6H)-yl)benzamide | 947 |
| Cpd-16 | (S)-N-((4-(((1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(3,3-difluoro-2,3-dihydropyrrolo[3',2':5,6]pyrido[2,3-b][1,4]oxazin-1(6H)-yl)benzamide | 947 |
| Cpd-17 | (S)-4-(4-((4'-chloro-5,5-dimethyl-3,4,5,6-tetrahydro-[1,1'-biphenyl]-2-yl)methyl)piperazin-1-yl)-2-(3,3-difluoro-2,3-dihydropyrrolo[3',2':5,6]pyrido[2,3-b][1,4]oxazin-1(6H)-yl)-N-((4-(((2-fluoro-1,4-dioxan-2-yl)methyl)amino)-3-nitrophenyl)sulfonyl)benzamide | 965 |
| Cpd-18 | (R)-4-(4-((4'-chloro-5,5-dimethyl-3,4,5,6-tetrahydro-[1,1'-biphenyl]-2-yl)methyl)piperazin-1-yl)-2-(3,3-difluoro-2,3-dihydropyrrolo[3',2':5,6]pyrido[2,3-b][1,4]oxazin-1(6H)-yl)-N-((4-(((2-fluoro-1,4-dioxan-2-yl)methyl)amino)-3-nitrophenyl)sulfonyl)benzamide | 965 |
| Cpd-19 | 4-(4-((4'-chloro-5,5-dimethyl-3,4,5,6-tetrahydro-[1,1'-biphenyl]-2-yl)methyl)piperazin-1-yl)-2-(3,3-difluoro-2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide | 945 |
| Cpd-20 | 4-(4-((4'-chloro-5,5-dimethyl-3,4,5,6-tetrahydro-[1,1'-biphenyl]-2-yl)methyl)piperazin-1-yl)-2-(3,3-difluoro-2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide | 945 |

Biological Example 1: Bcl-2 Competition Binding (Fluorescence Polarization) Assay The fluorescence-labeled 23 amino acid peptide BH3 was purchased from CalBiochem (NLWAAQRYGRELRRMSDKFVD). An unbound Fluorescein labeled BH3 peptide emits random light with respect to the plane of polarization plane of excited light, resulting in a lower polarization degree (mP) value. When the peptide is bound to Bcl-2, the complex tumble slower and the emitted light can have a higher level of polarization, resulting in a higher mP value. This binding assay was performed in 96-well plate and with each assay contained 15 and 30 nM of labeled peptide and purified Bcl-2 protein (purchased from R&D Systems, Inc). The assay buffer contained 20 mM Hepes (pH 7.0), 50 mM KCl, 5 mM $MgCl_2$, 20 mM $Na_2MoO_4$, 0.1 mg/ml Bovine Gamma Globulin and 0.01% NP40. Compounds were diluted in DMSO and added to the final assay with concentration range from 20 µM to 2 nM. The polarization degree (mP) value was determined by BioTek Synergy II with background subtraction after 3 hours of incubation at room temperature. $IC_{50}$ was calculated using Prism software with sigmoidal dose-response curve fitting. ABT-737 was used as reference compound. Such assays, carried out with a range of doses of test compounds, allowed the determination of an approximate $IC_{50}$ value. Although the inhibitory properties of the compounds of the present invention vary with structural change as expected, the activity generally exhibited by these agents was in the range of $IC_{50}$=0.1 1000 nM.

Biological Example 2: In Vitro Anti-Proliferation Assay in BCL-2-Dependent Acute Lymphoblastic Leukemia (ALL) Cell Line RS4;11

Cell antiproliferation was assayed by PerkinElmer ATPlite™ Luminescence Assay System. Briefly, the various test cancer cell lines were plated at a density of about $1 \times 10^4$ cells per well in Costar 96-well plates, and were incubated with different concentrations of compounds for about 72 hours in medium supplemented with 5% FBS or 10% normal human serum (NHS). One lyophilized substrate solution vial was then reconstituted by adding 5 mL of substrate buffer solution, and was agitated gently until the solution is homogeneous. About 50 μL of mammalian cell lysis solution was added to 100 μL of cell suspension per well of a microplate, and the plate was shaken for about five minutes in an orbital shaker at 700 rpm. This procedure was used to lyse the cells and to stabilize the ATP. Next, 50 μL substrate solution was added to the wells and microplate was shaken for five minutes in an orbital shaker at 700 rpm. Finally, the luminescence was measured by a PerkinElmer TopCount® Microplate Scintillation Counter. Such assays, carried out with a range of doses of test compounds, allowed the determination of the cellular anti-antiproliferative $IC_{50}$ of the compounds of the present invention. The following table lists the IC50 values of certain compounds of the invention. As shown below, Example 3 is significantly more potent than both NW-4-8 (Example 2) as well as ABT-199.

| Compound | IC50, RS4; 11 5% FBS |
| --- | --- |
| ABT-199 | 5.5 nM |
| Example 12 in WO/2017/132474 | 15.8 nM |
| Example 2 (NW-4-8) | 4.8 nM |
| Example 3 | 2.6 nM |

The following table lists the $IC_{50}$ values of another study for certain compounds of the invention.

| Compound | IC50, RS4; 11 5% FBS |
| --- | --- |
| ABT-199 | 9.2 nM |
| Example 3 | 1.4 nM |
| Example 6 (S, assumed) | 3.2 nM |
| Example 6 (R, assumed) | 1.3 nM |
| Example 7 | 5.6 nM |

The following table lists the $IC_{50}$ values of another study for certain compounds of the invention.

| Compound | IC50, RS4; 11 5% FBS |
| --- | --- |
| ABT-199 | 4.7 nM |
| Example 10 | 3.1 nM |

Biological Example 3: In Vitro Anti-Proliferation Assay in BCL-XL-Dependent Lines Small Cell Lung Cancer (SCLC) Cell Line H146

Cell antiproliferation was assayed by PerkinElmer ATPlite™ Luminescence Assay System. Briefly, the various test cancer cell lines were plated at a density of about $1\times10^4$ cells per well in Costar 96-well plates, and were incubated with different concentrations of compounds for about 72 hours in medium supplemented with 5% FBS. One lyophilized substrate solution vial was then reconstituted by adding 5 mL of substrate buffer solution, and was agitated gently until the solution was homogeneous. About 50 μL of mammalian cell lysis solution was added to 100 μL of cell suspension per well of a microplate, and the plate was shaken for about five minutes in an orbital shaker at 700 rpm. This procedure is used to lyse the cells and to stabilize the ATP. Next, 50 μL substrate solution was added to the wells and microplate was shaken for five minutes in an orbital shaker at 700 rpm. Finally, the luminescence was measured by a PerkinElmer TopCount® Microplate Scintillation Counter. Such assays, carried out with a range of doses of test compounds, allow the determination of the cellular anti-antiproliferative $IC_{50}$ of the compounds of the present invention.

Biological Example 4: Mice PK Study

The pharmacokinetics of compounds were evaluated in CD-1 mouse via Intravenous and Oral Administration. The IV dose was administered as a slow bolus in the Jugular vein, and oral doses were administered by gavage. The formulation for IV dosing is 5% DMSO in 20% HPBCD in water, and the PO formulation is 2.5% DMSO, 10% EtOH, 20% Cremphor EL, 67.5% D5W. The PK time point for the IV arm was 5, 15, 30 min, 1, 2, 4, 6, 8, 12, 24 hours post dose, and for PO arm was 15, 30 min, 1, 2, 4, 6, 8, 12, 24 hours post dose. Approximately 0.03 mL blood was collected at each time point. Blood of each sample was transferred into plastic micro centrifuge tubes containing EDTA-K2 and plasma was collected within 15 min by centrifugation at 4000 g for 5 minutes in a 4° C. centrifuge. Plasma samples were stored in polypropylene tubes. The samples were stored in a freezer at −75±15° C. prior to analysis. Concentrations of compounds in the plasma samples were analyzed using a LC-MS/MS method. WinNonlin (Phoenix™, version 6.1) or other similar software was used for pharmacokinetic calculations. The following pharmacokinetic parameters were calculated, whenever possible from the plasma concentration versus time data: IV administration: $C_0$, CL, $V_d$, $T_{1/2}$, $AUC_{inf}$, $AUC_{last}$, MRT, Number of Points for Regression; PO administration: $C_{max}$, $T_{max}$, $T_{1/2}$, $AUC_{inf}$, $AUC_{last}$, F %, Number of Points for Regression. The pharmacokinetic data was described using descriptive statistics such as mean, standard deviation. Additional pharmacokinetic or statistical analysis was performed at the discretion of the contributing scientist, and was documented in the data summary. The PK results of oral dosing of po, 10 mg/kg is shown in the Table below. As shown below, many compounds have significantly better PK than NW-4-8 (Example 2), see AUC and/or bioavailability values.

| Compound | AUC(h*ng/mL) | t½ (hour) | Bioavailabilty |
| --- | --- | --- | --- |
| Example 2 (NW-4-8) | 10,365 | 2.7 | 68% |
| Example 6 (S) | 12,068 | | 74% |
| Example 6 (R) | 16,114 | 3.2 | |
| Example 7 | 10,972 | 3.2 | 90% |
| Example 9 | 19,922 | 4.1 | |
| Example 10 | 34,982 | 4.1 | 78% |

For comparison purpose, the PK results of oral dosing of po, 10 mg/kg of certain compounds in WO/2017/132474 were obtained using the same methods and shown in the Table below.

| Compound | AUC(h*ng/mL) |
| --- | --- |
| Example 12 in WO/2017/132474 | 1,088 |
| Example 16 in WO/2017/132474 | 849 |
| Example 18 in WO/2017/132474 | 1,890 |

Biological Example 5: In Vivo Xenograft Studies

Compound of Example 3 was selected for in vivo studies in the BCL-2-dependent acute lymphoblastic leukemia RS4; 11 xenograft model. The CB.17 SCID mice were obtained at age 6-8 weeks from vendors and acclimated for a minimum 7-day period. The cancer cells were then implanted into the nude mice. Depending on the specific tumor type, tumors were typically detectable about two weeks following implantation. When tumor sizes reached 100-200 mm³, the animals with appreciable tumor size and shape were randomly assigned into groups of 8 mice each, including one vehicle control group and treatment groups. Dosing varies depending on the purpose and length of each study, which typically proceeded for about 3-4 weeks. Tumor sizes and body weight were typically measured three times per week. In addition to the determination of tumor size changes, the last tumor measurement was used to generate the tumor size change ratio (T/C value), a standard metric developed by the National Cancer Institute for xenograft tumor evaluation. In most cases, % T/C values were calculated using the following formula: % T/C=100×ΔT/ΔC if ΔT>0. When tumor regression occurred (ΔT<0), however, the following formula was used: % T/T0=100×ΔT/T0. Values of <42% were considered significant.

As shown below, 7 doses of Example 3 compound produced dose-dependent reduction of tumor growth. At 100 mg/kg, Example 3 compound led to complete regression of the tumor at day 18.

| Group | mice | Agent | mg/kg | Route | Schedule | BW Nadir | Tumor volume |
|---|---|---|---|---|---|---|---|
| 1 | 8 | vehicle | Vehicle | po | qd x 7 | −2.10% | 1124 mm³ |
| 2 | 8 | Example 3 | 25 | po | qd x 7 | −3.60% | 368 mm³ |
| 3 | 8 | Example 3 | 50 | po | qd x 7 | −2.90% | 26 mm³ |
| 4 | 8 | Example 3 | 100 | po | qd x 7 | −2.10% | 0 mm³ |
| 5 | 8 | ABT-199 | 50 | po | qd x 7 | −3.60% | 0 mm³ |

As shown below, Example 10 compound also produced dose-dependent reduction of tumor growth. At 50 mg/kg, Example 10 compound led to regression of the tumor at day 19.

| Group | mice | Agent | mg/kg | Route | Schedule | Tumor volume |
|---|---|---|---|---|---|---|
| 1 | 8 | vehicle | Vehicle | po | qd x 21 | 983.6 mm³ |
| 2 | 8 | Example 10 | 12.5 | po | qd x 21 | 295 mm³ |
| 3 | 8 | Example 10 | 25 | po | qd x 21 | 47.4 mm³ |
| 4 | 8 | Example 10 | 50 | po | qd x 21 | 32.0 mm³ |
| 5 | 8 | ABT-199 | 50 | po | qd x 21 | 17.4 mm³ |

What is claimed is:

1. A compound of Formula (A), or an N-oxide thereof, or a pharmaceutically acceptable salt, solvate, polymorph, tautomer, stereoisomer, an isotopic form, or a prodrug of said compound of Formula (A) or N-oxide thereof:

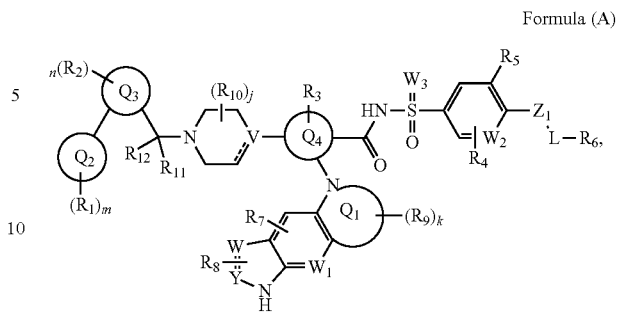

Formula (A)

wherein $Q_1$ is a 6-membered heterocycloalkyl, 6-membered heterocycloalkenyl, or 6-membered heteroaryl;

$Q_2$ is an aryl or heteroaryl;

$Q_3$ is a cycloalkyl, cycloalkenyl, heterocycloalkyl, heterocycloalkenyl, aryl, or heteroaryl;

$Q_4$ is

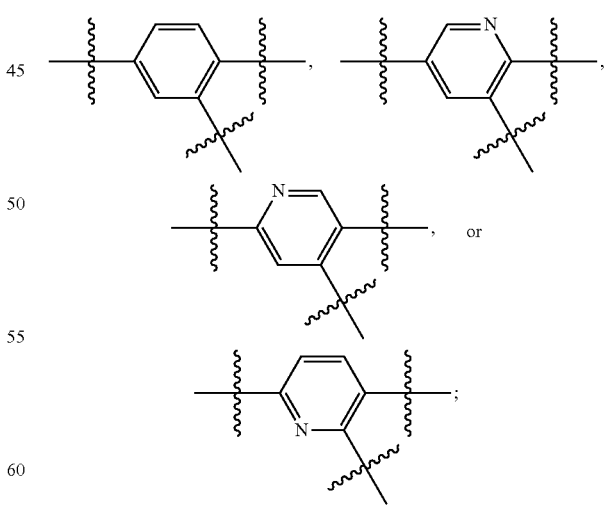

each of $R_1$, $R_2$, $R_3$, $R_4$, $R_5$, $R_6$, $R_7$, $R_8$, $R_9$, $R_{10}$, $R_{11}$, and $R_{12}$, independently, is H, D, alkyl, alkenyl, alkynyl, cycloalkyl, cycloalkenyl, heterocycloalkyl, heterocycloalkenyl, aryl, heteroaryl, halo, nitro, oxo, cyano, OR$_a$, SR$_a$, alkyl-R$_a$, NH(CH$_2$)$_p$R$_a$, C(O)R$_a$, S(O)R$_a$, SO$_2$R$_a$, C(O)OR$_a$, OC(O)R$_a$, NR$_b$R$_c$, P(O)R$_b$R$_c$, alkyl-P(O)R$_b$R$_c$, C(O)N(R$_b$)R$_c$, N(R$_b$)C(O)R$_c$, S(O)(=N(R$_a$))R$_b$, —N=S(O)R$_b$R$_c$, SO$_2$N(R$_b$)R$_c$, or N(R$_b$)SO$_2$R$_c$, in which said cycloalkyl, cycloalkenyl, heterocycloalkyl, heterocycloalkenyl, aryl, heteroaryl is optionally substituted with one or more R$_d$;

R$_a$, R$_b$, R$_c$ and R$_d$, independently, is H, D, alkyl, alkenyl, alkynyl, halo, cyano, amine, nitro, hydroxy, C(O)NHOH, C(O)OH, C(O)NH$_2$, alkoxy, alkoxyalkyl, haloalkyl, hydroxyalkyl, aminoalkyl, alkylcarbonyl, alkoxycarbonyl, alkylcarbonylamino, alkylamino, oxo, haloalkylamino, cycloalkyl, cycloalkenyl, heterocycloalkyl, heterocycloalkenyl, aryl, or heteroaryl, in which said alkyl, cycloalkyl, cycloalkenyl, heterocycloalkyl, heterocycloalkenyl, aryl, heteroaryl is optionally substituted with one or more R$_e$;

R$_e$ is H, D, alkyl, alkenyl, alkynyl, halo, cyano, amine, nitro, hydroxy, C(O)NHOH, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, heterocycloalkenyl, aryl, or heteroaryl;

Z$_1$ is a bond, (CH$_2$)$_p$, N(H), O, S, C(O), S(O$_2$), OC(O), C(O)O, OSO$_2$, S(O$_2$)O, C(O)S, SC(O), C(O)C(O), C(O)N(H), N(H)C(O), S(O$_2$)N(H), N(H)S(O$_2$), OC(O)O, OC(O)S, OC(O)N(H), N(H)C(O)O, N(H)C(O)S, N(H)C(O)N(H), (CH$_2$)$_p$N(H)(CH$_2$)$_q$, (CH$_2$)$_p$N(H)C(O)(CH$_2$)$_q$, (CH$_2$)$_p$C(O)N(H)(CH$_2$)$_q$, OC(O)N(H)(CH$_2$)$_{p+1}$N(H)(CH$_2$)$_q$, a bivalent alkenyl group, or a bivalent alkynyl group;

L is a bond, alkyl, alkenyl, alkynyl, cycloalkyl, cycloalkenyl, heterocycloalkyl, heterocycloalkenyl, aryl, or heteroaryl, in which said alkyl, cycloalkyl, cycloalkenyl, heterocycloalkyl, heterocycloalkenyl, aryl, or heteroaryl is optionally substituted with one or more R$_d$;

each of Y, W, and W$_2$, independently, is CH or N;

W$_1$ is N;

W$_3$ is O or N(R$_a$);

V is N, C, or CH;

two of R$_9$ group, taken together with the atom to which they are attached, may optionally form a cycloalkyl or heterocycloalkyl, in which said cycloalkyl or heterocycloalkyl of R$_9$ is optionally substituted with one or more R$_d$;

two of R$_2$ group, taken together with the atom to which they are attached, may optionally form a cycloalkyl or heterocycloalkyl, in which said cycloalkyl or heterocycloalkyl of R$_2$ is optionally substituted with one or more R$_d$;

two of R$_{10}$ group, taken together with the atom to which they are attached, may optionally form a cycloalkyl or heterocycloalkyl, in which said cycloalkyl or heterocycloalkyl of R$_{10}$ is optionally substituted with one or more R$_d$;

R$_{11}$ and R$_{12}$ group, taken together with the atom to which they are attached, may optionally form a cycloalkyl or heterocycloalkyl, in which said cycloalkyl or heterocycloalkyl of R$_{11}$ or R$_{12}$ is optionally substituted with one or more R$_d$;

R$_{10}$ and R$_2$ group, taken together with the atom to which they are attached, may optionally form a cycloalkyl or heterocycloalkyl, in which said cycloalkyl or heterocycloalkyl of R$_{10}$ or R$_2$ is optionally substituted with one or more R$_d$;

R$_4$ and —Z$_1$-L-R$_6$ group, taken together with the atom to which they are attached, may optionally form a cycloalkyl, cycloalkenyl, heterocycloalkyl, heterocycloalkenyl, aryl, or heteroaryl, in which said cycloalkyl, cycloalkenyl, heterocycloalkyl, heterocycloalkenyl, aryl, or heteroaryl of R$_4$ is optionally substituted with one or more R$_d$;

R$_b$ and R$_c$ group, taken together with the atom to which they are attached, may optionally form a cycloalkyl, or heterocycloalkyl, in which said cycloalkyl or heterocycloalkyl of R$_b$ and R$_c$, is optionally substituted with one or more R$_e$;

two of R$_d$ group, taken together with the atom to which they are attached, may optionally form a cycloalkyl, or heterocycloalkyl, in which said cycloalkyl or heterocycloalkyl of R$_d$ is optionally substituted with one or more R$_e$;

two of R$_e$ group, taken together with the atom to which they are attached, may optionally form a cycloalkyl, or heterocycloalkyl;

each of j and k, independently, is 0, 1, 2, 3, 4, 5, 6, 7, or 8; and each of m, n, p, and q, and independently, is 0, 1, 2, 3, or 4;

optionally, provided that when

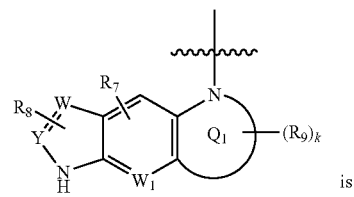

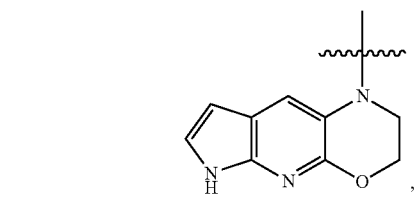

then —Z$_1$-L-R$_6$ is not

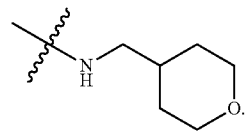 [SMILES: *NCC1CCOCC1]

2. The compound according to claim 1 or an N-oxide thereof, or a pharmaceutically acceptable salt, solvate, polymorph, tautomer, stereoisomer, an isotopic form, or a prodrug thereof, wherein the compound is represented by Formula (B):

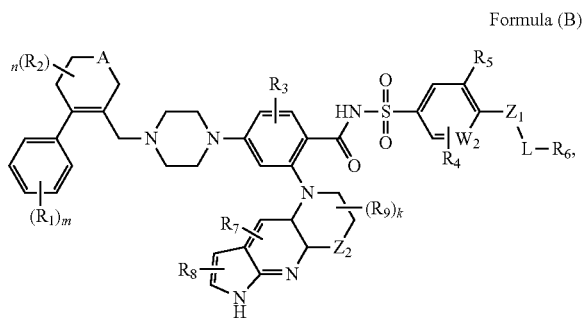

Formula (B)

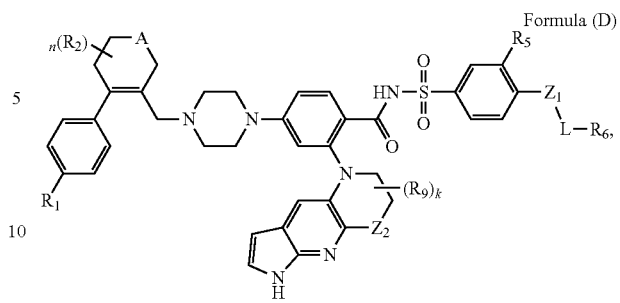

Formula (D)

wherein

Z$_2$ is —O—, —CH$_2$—, —C(O)—, —N(R$_a$)—, —S—, —S(O)—, —S(O$_2$)—, —S(O)(=N(R$_a$))—, —P(O)(R$_a$)—; wherein R$_a$ of Z$_2$, independently, is H, D, C$_1$-C$_6$alkyl, C$_2$-C$_6$alkenyl, C$_1$-C$_6$alkylcarbonyl, C1-C6alkoxycarbonyl, C3-C6cycloalkyl, 5-8 membered monocyclic heterocycloalkyl, C$_6$-C$_{14}$aryl, or 5-8 membered monocyclic heteroaryl, in which said C$_1$-C$_6$alkyl, C$_3$-C$_6$cycloalkyl, 5-8 membered monocyclic heterocycloalkyl, C$_6$-C$_{14}$aryl, 5-8 membered monocyclic heteroaryl is optionally substituted with one or more Re, and A is —(CR$_2$R$_2$)$_r$— or —O—; wherein r is 0, 1, 2, or 3;

each R$_2$ independently is H, —(C$_1$-C$_4$)alkoxy, —(C$_1$-C$_4$)alkyl optionally substituted with —(C$_1$-C$_4$)alkoxy, or two of R$_2$ groups, taken together with the same carbon atom to which they are attached, form —(C$_3$-C$_6$)cycloalkyl or 4-6 membered heterocyclic ring, wherein the —(C$_3$-C$_6$)cycloalkyl or 4-6 membered heterocyclic ring is optionally substituted with —(C$_1$-C$_4$)alkyl, —(C$_1$-C$_4$)haloalkyl or oxetanyl.

3. The compound according to claim 2 or an N-oxide thereof, or a pharmaceutically acceptable salt, solvate, polymorph, tautomer, stereoisomer, an isotopic form, or a prodrug thereof, wherein the compound is represented by Formula (C):

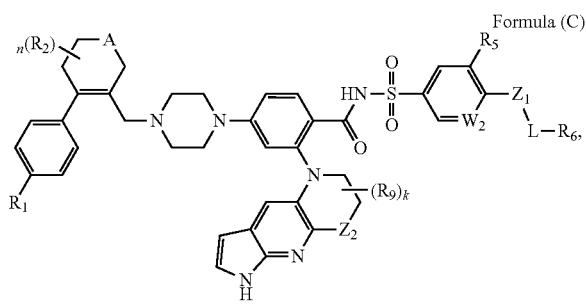

Formula (C)

wherein R$_1$ is H, D, halo or —(C$_1$-C$_4$)alkyl.

4. The compound according to claim 3 or an N-oxide thereof, or a pharmaceutically acceptable salt, solvate, polymorph, tautomer, stereoisomer, an isotopic form, or a prodrug thereof, wherein the compound is represented by Formula (D):

wherein

R$_5$ independently, is nitro, halo, or —SO$_2$R$_a$, wherein R$_a$ of R$_5$ is —(C$_1$-C$_4$)alkyl or —(C$_1$-C$_4$)haloalkyl;

Z$_1$ is absent, NH, N(H)(CH$_2$)$_q$, O, S, or —(C$_1$-C$_4$)alkylene, wherein q is 1, 2, or 3;

L is absent or —(C$_1$-C$_4$)alkylene optionally substituted with —(C$_3$-C$_6$)cycloalkyl; and R$_6$ is H, D, —P(O)(N(CH$_3$)$_2$)(OEt), —(C$_3$-C$_6$)cycloalkyl, phenyl, 5-7 membered heterocyclyl, 8-10 membered bicyclic ring, wherein the —(C$_3$-C$_6$)cycloalkyl, phenyl, 5-7 membered heterocyclyl, or 7-10 membered bicyclic ring is optionally substituted with halo, —OH, —CN, —COOH, —NH$_2$, —N(CH$_3$)$_2$, —(C$_1$-C$_4$)alkyl, —(C$_1$-C$_4$)alkoxy, cyclopropyl, 4-6 membered heterocyclyl, —CH$_2$P(O)(OH)$_2$, —CH$_2$P(O)((C$_1$-C$_4$)alkoxy)$_2$, —P(O)((C$_1$-C$_4$)alkyl)$_2$ or —N=S(O)((C$_1$-C$_4$)alkyl)$_2$.

5. The compound according to claim 4 or an N-oxide thereof, or a pharmaceutically acceptable salt, solvate, polymorph, tautomer, stereoisomer, an isotopic form, or a prodrug thereof, wherein R$_9$ independently, is D, halo, —OH, CN, —NH$_2$, =O, —(C$_1$-C$_4$)alkyl, —(C$_1$-C$_4$)alkoxy, —(C$_1$-C$_4$)haloalkyl, —(C$_1$-C$_4$)hydroxyalkyl, —(C$_3$-C$_6$)cycloalkyl, or 1,3-dithiolanyl; and k is 0, 1, 2, 3, or 4.

6. The compound according to claim 5 or an N-oxide thereof, or a pharmaceutically acceptable salt, solvate, polymorph, tautomer, stereoisomer, an isotopic form, or a prodrug thereof, wherein A is —CH$_2$— or —O—.

7. The compound according to claim 6 or an N-oxide thereof, or a pharmaceutically acceptable salt, solvate, polymorph, tautomer, stereoisomer, an isotopic form, or a prodrug thereof, wherein each R$_2$ independently is —CH$_3$; and n is 0 or 2.

8. The compound according to claim 7 or an N-oxide thereof, or a pharmaceutically acceptable salt, solvate, polymorph, tautomer, stereoisomer, an isotopic form, or a prodrug thereof, wherein Z$_2$ is —O—.

9. The compound according to claim 8 or an N-oxide thereof, or a pharmaceutically acceptable salt, solvate, polymorph, tautomer, stereoisomer, an isotopic form, or a prodrug thereof, wherein R$_1$ is Cl.

10. The compound according to claim 9 or an N-oxide thereof, or a pharmaceutically acceptable salt, solvate, polymorph, tautomer, stereoisomer, an isotopic form, or a prodrug thereof, wherein R$_5$ is nitro.

11. The compound according to claim 10 or an N-oxide thereof, or a pharmaceutically acceptable salt, solvate, polymorph, tautomer, stereoisomer, an isotopic form, or a prodrug thereof, wherein Z$_1$ is absent, NH or O.

12. The compound according to claim 11 or an N-oxide thereof, or a pharmaceutically acceptable salt, solvate, polymorph, tautomer, stereoisomer, an isotopic form, or a prodrug thereof, wherein Z$_2$ is —O—, —CH$_2$—, —C(O)—, —NH—, —N-(oxetanyl)-, —S—, —S(O)—, —S(O$_2$)—, —S(O)(=NH)—, —S(O)(=NCH$_3$)—, or —P(O)(CH$_3$)—.

13. The compound according to claim 12 or an N-oxide thereof, or a pharmaceutically acceptable salt, solvate, polymorph, tautomer, stereoisomer, an isotopic form, or a prodrug thereof, wherein R$_6$ is H, D, —(C$_3$-C$_6$)cycloalkyl, phenyl, tetrahydro-2H-pyranyl, or 1,4-dioxanyl, wherein the —(C$_3$-C$_6$)cycloalkyl, phenyl, tetrahydro-2H-pyranyl or 1,4-dioxanyl is optionally substituted with 1 or 2 groups selected from halogen, —OH, =O, —(C$_1$-C$_4$)alkyl, or —(C$_1$-C$_4$)alkoxy.

14. The compound according to claim 13 or an N-oxide thereof, or a pharmaceutically acceptable salt, solvate, polymorph, tautomer, stereoisomer, an isotopic form, or a prodrug thereof, wherein R$_6$ is tetrahydro-2H-pyranyl or 1,4-dioxanyl, wherein the tetrahydro-2H-pyranyl or 1,4-dioxanyl is optionally substituted with 1 or 2 groups selected from halogen.

15. The compound according to claim 1 or an N-oxide thereof, or a pharmaceutically acceptable salt, solvate, polymorph, tautomer, stereoisomer, an isotopic form, or a prodrug thereof, wherein the compound is (R)-4-(4-((4'-chloro-5,5-dimethyl-3,4,5,6-tetrahydro-[1,1'-biphenyl]-2-yl)methyl)piperazin-1-yl)-2-(3-methyl-2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, (S)-4-(4-((4'-chloro-5,5-dimethyl-3,4,5,6-tetrahydro-[1,1'-biphenyl]-2-yl)methyl)piperazin-1-yl)-2-(3-methyl-2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, (R)-4-(4-((4'-chloro-5,5-dimethyl-3,4,5,6-tetrahydro-[1,1'-biphenyl]-2-yl)methyl)piperazin-1-yl)-2-(2-methyl-2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]thiazin-1(6H)-yl)-N-((3-nitro-4-(((tetrahydro-2H-pyran-4-yl)methyl)amino)phenyl)sulfonyl)benzamide, (R)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(3-(trifluoromethyl)-2,3-dihydropyrrolo[3',2':5,6]pyrido[2,3-b][1,4]oxazin-1(6H)-yl)benzamide, (R)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(3-(trifluoromethyl)-2,3-dihydropyrrolo[3',2':5,6]pyrido[2,3-b][1,4]thiazin-1(6H)-yl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, (R)-4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(2-methyl-2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-2-(2,2-dimethyl-2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, (R)-4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(3-methyl-2,3-dihydropyrrolo[3',2':5,6]pyrido[2,3-b][1,4]oxazin-1(6H)-yl)benzamide, (S)-4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(3-methyl-2,3-dihydropyrrolo[3',2':5,6]pyrido[2,3-b][1,4]oxazin-1(6H)-yl)benzamide, (S)-4-(4-((4'-chloro-5,5-dimethyl-3,4,5,6-tetrahydro-[1,1'-biphenyl]-2-yl)methyl)piperazin-1-yl)-2-(2-methyl-2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(4,4-dioxido-2,3-dihydropyrrolo[3',2':5,6]pyrido[2,3-b][1,4]thiazin-1(6H)-yl)-N-((3-nitro-4-(((tetrahydro-2H-pyran-4-yl)methyl)amino)phenyl)sulfonyl)benzamide, (S)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(3-(trifluoromethyl)-2,3-dihydropyrrolo[3',2':5,6]pyrido[2,3-b][1,4]oxazin-1(6H)-yl)benzamide, (S)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(3-(trifluoromethyl)-2,3-dihydropyrrolo[3',2':5,6]pyrido[2,3-b][1,4]thiazin-1(6H)-yl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl-2,2,3,3-d4)-N-((4-(((4-fluorotetrahydro-2H-pyran-4-yl)methyl)amino)-3-nitrophenyl)sulfonyl)benzamide, (S)-4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(2-methyl-2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-2-(3,3-dimethyl-2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, N-((4-((((R)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-((S)-3-methyl-2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-N-((4-((((S)-2-fluoro-1,4-dioxan-2-yl)methyl)amino)-3-nitrophenyl)sulfonyl)-2-((S)-3-methyl-2,3-dihydropyrrolo[3',2':5,6]pyrido[2,3-b][1,4]oxazin-1(6H)-yl)benzamide, (R)—N-((4-(((1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzamide, (S)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((2-fluoro-1,4-dioxan-2-yl)methyl)amino)-3-nitrophenyl)sulfonyl)benzamide, (R)—N-((4-(((1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(3,3-difluoro-2,3-dihydropyrrolo[3',2':5,6]pyrido[2,3-b][1,4]oxazin-1(6H)-yl)benzamide, (S)-4-(4-((4'-chloro-5,5-dimethyl-3,4,5,6-tetrahydro-[1,1'-biphenyl]-2-yl)methyl)piperazin-1-yl)-2-(3,3-difluoro-2,3-dihydropyrrolo[3',2':5,6]pyrido[2,3-b][1,4]oxazin-1(6H)-yl)-N-((4-(((2-fluoro-1,4-dioxan-2-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,3-difluoro-2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, N-((4-((S)-1,4-dioxan-2-yl)meth 1)amino)-3-nitrophenyl) sulfon 1)-4-(4-((4'-chloro-5,5-dimethyl-3,4,5,6-tetrahydro-[1,1'-biphenyl]-2-yl)methyl)piperazin-1-yl)-2-((S)-3-methyl-2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((((R)-2-fluoro-1,4-dioxan-2-yl)methyl)amino)-3-nitrophenyl)sulfonyl)-2-((S)-3-methyl-2,3-dihydropyrrolo[3',2':5,6]pyrido[2,3-b][1,4]oxazin-1(6H)-yl)benzamide, (S)-N-((4-(((1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzamide, (R)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((2-fluoro-1,4-dioxan-2-yl)methyl)amino)-3-nitrophenyl)sulfonyl)benzamide, (S)-N-((4-(((1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(3,3-difluoro-2,3-dihydropyrrolo[3',2':5,6]pyrido[2,3-b][1,4]oxazin-1(6H)-yl)benzamide, (R)-4-(4-((4'-chloro-5,5-dimethyl-3,4,5,6-tetrahydro-[1,1'-biphenyl]-2-yl)methyl)piperazin-1-yl)-2-(3,3-difluoro-2,3-dihydropyrrolo[3',2':5,6]pyrido[2,3-b][1,4]oxazin-1(6H)-yl)-N-((4-(((2-fluoro-1,4-dioxan-2-yl)methyl)amino)-3-nitrophenyl)sulfonyl)benzamide, or 4-(4-((4'-chloro-5,5-dimethyl-3,4,5,6-tetrahydro-[1,1'-biphenyl]-2-yl)methyl)piperazin-1-yl)-2-(3,3-difluoro-2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide.

16. A pharmaceutical composition comprising a compound of Formula (A) or an N-oxide thereof as defined in claim 1, or a pharmaceutically acceptable salt, solvate, polymorph, tautomer, stereoisomer, an isotopic form, or a prodrug of said compound of Formula (A) or an N-oxide thereof, and a pharmaceutically acceptable diluent or carrier.

17. A method of healing, alleviating, relieving, altering, remedying, ameliorating, improving, or affecting of a neoplastic disease, or the symptoms thereof, comprising administering to a subject in need thereof an effective amount of a compound of Formula (A) or an N-oxide thereof as defined in claim 1, or a pharmaceutically acceptable salt, solvate, polymorph, tautomer, stereoisomer, an isotopic form, or a prodrug of said compound of Formula (A) or an N-oxide thereof.

18. The method of claim 17, wherein the neoplastic disease is characterized by enhanced or increased Bcl-2 activity.

19. The method of claim 17, wherein the neoplastic disease is myeloma, multiple myeloma, lymphoma, follicular lymphoma (FL), non-Hodgkin's lymphoma, leukemia, acute leukemia, acute lymphoblastic leukemia (ALL), chronic lymphoblastic leukemia (CLL), chronic myeloid leukemia (CML), mantle cell lymphoma (MCL), diffuse large B-cell lymphoma, lung cancer, melanoma, breast cancer, or prostate cancer, or drug-resistant cancer thereof.

20. The method of claim 17, further comprising administering one or more further treatment(s) effective to treat the neoplastic disease.

21. The method of claim 20, wherein said one or more further treatment(s) comprise: surgery, radiation therapy, a chemotherapeutic agent, a target therapy, an antibody-drug conjugate (ADC), an immunotherapy, or a CAR-T therapy.

22. The method of claim 21, wherein said chemotherapeutic agent comprises bendamustine, NL-101, cisplatin, carboplatin, etoposide, or topotecan.

23. The method of claim 21, wherein said target therapy comprises rituximab, ibrutinib, ACP-196, or idelalisib.

24. The method of claim 21, wherein said ADC comprises brentuximab vedotin.

25. The method of claim 21, wherein said immunotherapy comprises pembrolizumab, nivolumab, atezolizumab, durvalumab, or avelumab.

26. The method of claim 21, wherein said CAR-T therapy comprises tisagenlecleucel or axicabtagene ciloleucel.

27. The method of claim 19, wherein said ALL is BCL-2-dependent ALL or pediatric ALL.

28. The method of claim 19, wherein said CLL is relapsed/refractory CLL, or del(17p) CLL.

29. The method of claim 19, wherein said CML is blast-crisis CML.

30. The method of claim 19, wherein said lung cancer is small cell lung cancer (SCLC).

* * * * *